US012773432B2

(12) United States Patent
Nagler et al.

(10) Patent No.: US 12,773,432 B2
(45) Date of Patent: Oct. 27, 2026

(54) METHODS AND COMPOSITIONS FOR TREATING AUTOIMMUNE AND ALLERGIC DISORDERS

(71) Applicants: THE UNIVERSITY OF CHICAGO, Chicago, IL (US); THE BOARD OF TRUSTEES OF THE LELAND STANFORD JUNIOR UNIVERSITY, Stanford, CA (US)

(72) Inventors: Cathryn R. Nagler, Chicago, IL (US); Kari Nadeau, Stanford, CA (US); Riyue Bao, Chicago, IL (US); Lauren Anders Hesser, Chicago, IL (US)

(73) Assignees: THE UNIVERSITY OF CHICAGO, Chicago, IL (US); THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 785 days.

(21) Appl. No.: 18/006,385

(22) PCT Filed: Jul. 22, 2021

(86) PCT No.: PCT/US2021/070926

§ 371 (c)(1),
(2) Date: Jan. 21, 2023

(87) PCT Pub. No.: WO2022/020852

PCT Pub. Date: Jan. 27, 2022

(65) Prior Publication Data

US 2023/0256034 A1 Aug. 17, 2023

Related U.S. Application Data

(60) Provisional application No. 63/122,833, filed on Dec. 8, 2020, provisional application No. 63/108,736, filed on Nov. 2, 2020, provisional application No. 63/055,227, filed on Jul. 22, 2020.

(51) Int. Cl.
*A61K 35/741* (2015.01)
*A61K 39/35* (2006.01)
*A61K 47/36* (2006.01)
*A61P 37/08* (2006.01)

(52) U.S. Cl.
CPC ............ *A61K 35/741* (2013.01); *A61K 39/35* (2013.01); *A61K 47/36* (2013.01); *A61P 37/08* (2018.01)

(58) Field of Classification Search
None
See application file for complete search history.

(56) References Cited

U.S. PATENT DOCUMENTS

| | | | |
|---|---|---|---|
| 10,369,176 | B2 | 8/2019 | Goodman et al. |
| 2007/0258953 | A1 | 11/2007 | Duncan et al. |
| 2008/0275141 | A1 | 11/2008 | Whiteford |
| 2014/0341921 | A1 | 11/2014 | Honda et al. |
| 2016/0271189 | A1 | 9/2016 | Cutcliffe et al. |
| 2016/0317653 | A1 | 11/2016 | Cook et al. |
| 2019/0282647 | A1 | 9/2019 | Öckerman |

FOREIGN PATENT DOCUMENTS

| | | |
|---|---|---|
| CN | 108676774 A | 10/2018 |
| JP | 2015 500792 | 1/2015 |
| JP | 2019-511563 | 4/2019 |
| WO | WO 2013/080561 | 6/2013 |
| WO | WO 2015/095241 | 6/2015 |
| WO | WO 2016/070151 | 5/2016 |
| WO | WO 2017/079450 | 5/2017 |
| WO | WO 2017/134240 | 8/2017 |
| WO | WO 2018/057914 | 3/2018 |
| WO | WO 2018/075886 | 4/2018 |
| WO | WO 2018/106844 | 6/2018 |
| WO | WO 2018/107365 | 6/2018 |
| WO | WO 2018/129249 | 7/2018 |
| WO | WO 2018/187272 | 10/2018 |
| WO | WO 2018/195067 | 10/2018 |
| WO | WO 2020/097077 | 5/2020 |
| WO | WO 2020/109646 | 6/2020 |

OTHER PUBLICATIONS

Inoue et al., "A preliminary study of gut dysbiosis in children with food allergy", Bioscience, Biotechnology, and Biochemistry, 81(12):2396-2399, 2017.
Bashir et al., "Toll-like receptor 4 signaling by intestinal microbes influences susceptibility to food allergy" J Immunol 2004, 172, 6978-6987.
Berni Canani et al., "Lactobacillus rhamnosus GG-supplemented formula expands butyrate-producing bacterial strains in food allergic infants" The ISME Journal 2016, 10, 742-750.
Bunyavanich et al., "Early-life gut microbiome composition and milk allergy resolution" J Allergy Clin Immunol 2016, 138, 1122-1130.
Cahenzli et al., "Intestinal microbial diversity during early-life colonization shapes long-term IgE levels" Cell Host Microbe 2013, 14, 559-570.
Chen et al., "Role of lactic acid bacteria on the yogurt flavour: A review," International Journal of Food Properties, 20(S1):S316-S330, 2017.
Dominguez-Bello et al. "Delivery mode shapes the acquisition and structure of the initial microbiota across multiple body habitats in newborns" Proc Natl Acad Sci U S A 2010, 107, 11971-11975.

(Continued)

*Primary Examiner* — Brian Gangle
(74) *Attorney, Agent, or Firm* — Norton Rose Fulbright US LLP

(57) ABSTRACT

The current disclosure provides methods and compositions for treating autoimmune conditions, including allergic conditions such as food allergy. Certain aspects of the disclosure relate to methods for treatment of food allergy comprising administering a composition comprising *Phascolarctobacterium faecium* and/or *Ruminococcus bromii*. In some aspects, disclosed are compositions comprising isolated, lyophilized bacteria such as *Phascolarctobacterium faecium* and/or *Ruminococcus bromii*.

18 Claims, 36 Drawing Sheets

(56) References Cited

OTHER PUBLICATIONS

Duncan et al., "Lactate-utilizing bacteria, isolated from human feces, that produce butyrate as a major fermentation product" Appl Environ Microbiol 2004, 70, 5810-5817.
English translation of Office Communication issued in Chinese Patent Application No. 201980087923.6, dated Aug. 9, 2023.
English translation of Office Communication issued in Japanese Patent Application No. 2021-524290, dated Sep. 4, 2023.
Extended European Search Report issued in Corresponding European Application No. 19882127.4, dated Jul. 22, 2022.
International Search Report and Written Opinion issued in Corresponding PCT Application No. PCT/US2019/059865, dated Feb. 20, 2020.
Ivory et al., "Oral delivery of Lactobacillus casei Shirota modifies allergen-induced immune responses in allergic rhinitis" Clinical and Experimental Allergy 2008, 38, 1282-1289.
Li, "Modern Nutrition and Food Safety", 2nd Edition, Second Military Medical University Press, pp. 56, Feb. 28, 2013 with English Translation.
Mueller et al., "The infant microbiome development: mom matters" Trends Mol Med 2015, 21, 109-117.
Pascal et al., "Microbiome and Allergic Diseases" Frontiers in Immunology 2018, 9(1584), 1-9.
Planer et al., "Development of the gut microbiota and mucosal IgA responses in twins and gnotobiotic mice" Nature 2016, 534, 263-266.
Plunkett et al., "The Influence of the Microbiome on Allergic Sensitization to Food" Immunol 2017, 198, 581-589.
Sato et al., "Isolation of lactate-utilizing butyrate-producing bacteria from human feces and in vivo administration of Anaerostipes caccae strain L2 and galacto-oligosaccharides in a rat model," FEMS Microbiol Ecol., 66(3):528-536, 2008.
Schwiertz et al., "*Anaerostipes caccae* gen. nov., sp. nov., a new saccharolytic, acetate-utilising, butyrate-producing bacterium from human faeces" Systematic and applied microbiology 2002, 25, 46-51.
Van den Abbeele et al., "Arabinoxylans and inulin differentially modulate the mucosal and luminal gut microbiota and mucin-degradation in humanized rats" Environmental Microbiology 2011, 13(10), 2667-2680.
Wesemann et al., "The Microbiome, Timing, and Barrier Function in the Context of Allergic Disease" Immunity 2016, 44, 728-738.
People's Medical Publishing House, "Lecture Series on Antibiotics", Institute of Antibiotics, Chinese Academy of Medical Sciences, Oct. 31, 1959, p. 108 (with English Translation).
Chia et al., "Bacteroides thetaiotaomicron Fosters the Growth of Butyrate-Producing Anaerostipes caccae in the Presence of Lactose and Total Human Milk Carbohydrates," Microorganisms, Oct. 1, 2020, 8(10):1-13.
Li, et al., "Anaerobic Bacteria," Anhui Science and Technology Publishing House, Dec. 31, 1983, p. 165 (with English Translation).
Office Communication issued in Chinese Patent Application No. 201980087923.6, dated Jun. 5, 2024 (with English Translation).
Feehley T, et al. "Healthy infants harbor intestinal bacteria that protect against food allergy", *Nat Med.* 25(3), pp. 448-453, 2019.
International Search Report and Written Opinion issued in corresponding International application PCT/US2021/070926 mailed Dec. 7, 2021.
Stefka AT, et al. "Commensal bacteria protect against food allergen sensitization." *Proc Natl Acad Sci U.S.A.*, 111(36), pp. 13145-13150, 2014.
Belengeur et al., "Two Routes of Metabolic Cross-Feeding between Bifidobacterium adolescentis and Butyrate-Producing Anaerobes from the Human Gut," Applied and Environmental Microbiology, 72(5):3593-3599, 2006.
English translation of Office Communication issued in Japanese Patent Application No. 2021-524290, dated Apr. 15, 2024.
Bircher et al., "Effect of cryopreservation and lyophilization on viability and growth of strict anaerobic human gut microbes," Microbial Biotechnology, 11:721-733, 2018.
Falony et al., "Cross-feeding between Bifidobacterium longum BB536 and acetate-converting, butyrate-producing colon bacteria during growth on oligofructose," Applied and Environmental Microbiology, 72:7835-7841, 2006.
Ose et al., "The ability of human intestinal anaerobes to metabolize different oligosaccharides: Novel means for microbiota modulation?" Anaerobe, 51:110-119, 2018.

METHODS AND COMPOSITIONS FOR TREATING AUTOIMMUNE AND ALLERGIC DISORDERS

CROSS-REFERENCE TO RELATED APPLICATIONS

This application is a national phase under 35 U.S.C. § 371 of International Application No. PCT/US2021/070926, filed Jul. 22, 2021, which claims priority to U.S. Provisional Patent Application No. 63/055,227, filed Jul. 22, 2020, U.S. Provisional Patent Application No. 63/108,736, filed Nov. 2, 2020, and U.S. Provisional Patent Application No. 63/122,833, filed Dec. 8, 2020, the entire contents of each of which are incorporated herein by reference in their entirety.

STATEMENT OF GOVERNMENT SUPPORT

This invention was made with government support under grant number AI134923, awarded by the National Institutes of Health. The government has certain rights in this invention.

BACKGROUND

I. Field

Aspects of this invention relate to the fields of molecular biology, immunology, and medicine.

II. Background

Recent surveys estimate that 32 million children and adults in the United States suffer from food allergies (1, 2). This marked increase in allergic responses to food in industrialized societies worldwide parallels increases in other non-communicable diseases (NCDs) including obesity, diabetes, asthma, autism, and inflammatory bowel disease. These NCDs share an association with dysbiosis of the commensal microbiome, particularly in the gut (3). Early childhood is a particular period of vulnerability for the maturation of the microbiota and the developing immune system, which are intimately intertwined (4, 5).

An association between gut microbial community changes and childhood food allergies has been reported in some epidemiological studies (6-8). A Canadian healthy infant longitudinal development (CHILD) study showed alterations in the gut microbial community in food-sensitized infants, in which Enterobacteriaceae were overrepresented in a less diverse microbial community in infants at 3 months of age, whereas Bacteroidaceae were underrepresented at 1 year (8). A Chinese infant cohort study showed that infants with food allergies had a higher abundance of Firmicutes and lower abundance of Bacteroidetes at 6 months, but no significant difference in the total microbial diversity was found (7).

Oral (OIT) and epicutaneous (EPIT) immunotherapy, allergen-specific desensitization protocols performed by introducing small but gradually increasing doses of allergen, have been shown to safely and effectively desensitize food-allergic patients to their allergens (9-11). However, OIT requires a prolonged period of updosing (usually years) during which gastrointestinal symptoms are common and might contribute to the high withdrawal rate observed in clinical trials (12,13). Although OIT can achieve short-term desensitization, this desensitization is not sustained without daily maintenance dosing, and long-term tolerance is not induced in the majority of the cases (10). Live microbiome-modulating biotherapeutics have shown promise in clinical trials for a variety of diseases (14). Pre-clinical data suggests that microbiome-modulating therapeutics may have the potential for improving both the efficacy and safety of OIT. Mouse model work has shown that preventing an allergic response to food requires the induction of both a food allergen-specific immunoregulatory response and a commensal bacteria-induced intestinal barrier protective response which regulates epithelial permeability to food allergens (15).

Recognized is a need for compositions and methods for effective and sustained treatment of autoimmune conditions, including food allergy.

SUMMARY OF THE INVENTION

The current disclosure fulfills the need in the art by providing methods and compositions for treating allergies, including food allergies, and other autoimmune conditions. Accordingly, aspects of the present disclosure provide methods and compositions useful for preventing or reducing an immune response to an allergen, including a food allergen.

Embodiments of the disclosure include methods for preventing an immune response, methods for reducing an immune response, methods for treating an allergy, methods for treating an autoimmune disorder, methods for reducing inflammation, methods for treating a food allergy, methods for diagnosing a food allergy, methods for determining a risk of developing a food allergy, live bacterial compositions, freeze-dried bacterial compositions, lyophilized bacterial compositions, and bacterial formulations.

Methods of the present disclosure can include at least 1, 2, 3, 4, 5, or more of the following steps: administering a bacterial composition to a subject, administering one or more metabolites to a subject, administering one or more nanoparticles to a subject, administering one or more microparticles to a subject, administering a prebiotic to a subject, determining a subject to have a decreased operational taxonomic unit (OTU) abundance score, determining a subject to have an increased OTU abundance score, determining a subject to have a decreased abundance of metabolites from a metabolic pathway, determining a subject to have an increased abundance of metabolites from a metabolic pathway, providing a food allergy therapy to a subject, diagnosing a food allergy in a subject, identifying a risk of a food allergy in a subject, sensitizing a subject to immunotherapy, treating a subject with immunotherapy, immunizing a subject for a food allergy, generating a bacterial composition, isolating one or more bacteria from a subject, purifying one or more bacteria, lyophilizing a bacterial product, obtaining a biological sample from a subject, obtaining a fecal sample from a subject, comparing a fecal sample from a healthy subject with a fecal sample from an subject having a food allergy, generating a bacterial product, and generating a mixture of two or more bacteria. It is contemplated that any one or more of these steps may be excluded from certain embodiments of the disclosure.

Compositions of the present disclosure can include at least 1, 2, 3, or more of the following components: a live bacterial product, a freeze-dried bacterial product, a lyophilized bacterial product, a prebiotic, *Phascolarctobacterium faecium, Agathobaculum desmolans, Ruminococcus bromii*, one or more nanoparticles, one or more microparticles, and a pharmaceutical excipient. It is contemplated that any one or more of these components may be excluded from certain embodiments of the disclosure.

Aspects of the disclosure are directed to a method for preventing or reducing an immune response to an allergen in a subject, the method comprising administering to the subject a composition comprising a therapeutically effective amount of *Phascolarctobacterium faecium* and/or *Ruminococcus bromii*. In some embodiments, the composition comprises *Phascolarctobacterium faecium*. In some embodiments, the composition comprises between $1\times10^3$ and $1\times10^{15}$ colony forming units (CFU) of *Phascolarctobacterium faecium*. In some embodiments, the *Phascolarctobacterium faecium* makes up at least 75%, 80%, 85%, 90%, 95%, or 99% of the composition, or any value or range derivable therein. In some embodiments, the composition comprises *Ruminococcus bromii*. In some embodiments, the composition comprises between $1\times10^3$ and $1\times10^{15}$ CFU of *Ruminococcus bromii*. In some embodiments, the *Ruminococcus bromii* makes up at least 75%, 80%, 85%, 90%, 95%, or 99% of the composition, or any value or range derivable therein. In some embodiments, the composition comprises *Phascolarctobacterium faecium* and *Ruminococcus bromii*. In some embodiments, the composition comprises at least 75%, 80%, 85%, 90%, 95%, or 99% *Phascolarctobacterium faecium* and *Ruminococcus bromii*, or more, or any value or range derivable therein. In some embodiments, the composition does not comprise more than a contaminating amount of any other bacteria. In some embodiments, the composition does not comprise a detectable amount of any other bacteria. In some embodiments, the composition further comprises one or more microparticles. The bacteria may be encapsulated in the one or more microparticles. Alternatively, the bacteria may not be encapsulated in the one or more microparticles. The bacteria may be associated with one or more nanoparticles.

In some embodiments, the allergen is a food allergen. In some embodiments, the food allergen is peanuts, tree nuts, shellfish, soy, egg, fish, mustard, oats, olives, corn, rice, pineapple, wheat, gluten, milk, sesame, garbanzo beans, bananas, kiwi, avocado, mangos, melons, carrots, cucumber, apples, squash, or crab. In some embodiments, the subject was determined to have symptoms of a food allergy. In some embodiments, the food allergy is an allergy to 1, 2, 3, 4, 5, 6, 7, or 8 different foods, or more. In some embodiments, the subject was diagnosed with a food allergy. In some embodiments, the subject was not diagnosed with a food allergy. In some embodiments, the subject has previously been treated for a food allergy. In some embodiments, the subject was determined to be resistant to the previous treatment. In some embodiments, the subject has not been previously treated for a food allergy.

In some embodiments, the composition comprises a bacterial product comprising the *Phascolarctobacterium faecium* and/or *Ruminococcus bromii*. In some embodiments, the bacterial product is a live bacterial product. In some embodiments, the bacterial product is a lyophilized or freeze-dried bacterial product. In some embodiments, the bacterial product is isolated from a human subject. In some embodiments, the bacterial product is a bacterial product isolated from a non-human subject. In some embodiments, the composition is administered orally.

In some embodiments, the method comprises preventing an anaphylactic response in the subject. In some embodiments, the method further comprises providing to the subject a prebiotic. The term “prebiotic” refers to an oligosaccharide or polysaccharide with a degree of polymerization of two or more that is not susceptible to digestion or degradation prior to entering the upper gastrointestinal tract, such as the small intestine, and is fermentable or digestible by microbes or other processes within the colon in which the fermented or digested oligosaccharides or their byproducts of digestion alter the microbiome or provide benefit to human or animal.

In some embodiments, the prebiotic comprises fructan (including short-chain fructooligosaccharides (scFOS), fructo-oligosaccharides (FOS), and inulin), galactans, glucans, and/or other oligosaccharides. Examples of such include short-chain FOS (shorter chains of fructose below, with degree of polymerization from 2-4); fructooligosaccharides (with degree of polymerization of 4-20); inulin (with degree of polymerization >20) or phlein; soybeanoligosaccharide (SOS); galactooligosacchararide (GOS); isomaltooligosaccharide (IMOS) (derived from starches in wheat, barley, corn, oats, tapioca, rice, potato) including isomaltose, isomaltotriose, and panose; soybeanoligosaccharides (SOS) (from soybean) including raffinose and tetrasaccharide stachyose; xylooligosaccharides (XOS) including xylan, xylobiose, xylothiose, and xylotetraose (derived from starches found in bamboo shoots, fruits, vegetables, milk, and honey); pecticoligosaccharides (POS) including pectin; chitooligosaccharides including chitin; lactulose; beta-glucans (from cereal grains, such as oat, barley, wheat, and rye); Type I resistant starch; Type II resistant starch; and Type III resistant starch, which includes resistant starch that is formed when starch-containing foods heated then are cooled (ex. pasta, potatoes, and rice). Further examples include polyols such as isomalt, maltitol, mannitol, sorbitol, xylitol, lactitol, erythritol, and polyglycitol. Sources of polyols include apples, apricots, avocados, blackberries, cherries, lychees, nectarines, peaches, pears, plums, prunes, watermelon, cauliflower, and mushrooms. Even further examples include non-fructans such as dextrins, including maltodextrins, cyclodextrins, and pirodextrins (derived from potato and maize starch), wheat dextrin, high-amylose cornstarch (and maizestarch), amylose, and amylopectin. In some embodiments, the prebiotic comprises one or more of wherein the prebiotic comprises one or more of galactooligosacchararide, lactulose, lactitol, erythritol, isomalt, polyglycitol, and succinate. In some embodiments, the prebiotic comprises one or more of galactooligosacchararide, lactulose, succinate, and lactitol.

In some embodiments, at least 1, 2, 3, 4, 5, 6, 7, 8, 9, 10, 1, 12, 13, 14, or 15 grams of prebiotic, or more, is administered to the subject. In some embodiments, at least 10 grams of prebiotic is administered to the subject. In some embodiments, the ratio or the colony forming units of the *Phascolarctobacterium faecium* or *Ruminococcus bromii* to grams or prebiotic is between 1000:1 and 10000:1, or any range or value derivable therein.

Also included are derivatives and processed forms of the compounds described herein. Derivatives or processed forms may be modified to alter the fermentation properties of the prebiotic, for example, by making the prebiotic more readily digestible, more specific to a certain type of bacterium, or to increase yield of fermentation products, such as short-chain fatty acids (SCFAs) and/or other metabolites. Also included are foods and food derivatives known to contain quantities of these compounds and/or which are capable of having a prebiotic effect. These foods may be processed to isolate their starches, or may be administered without isolation of their starches, e.g. by grinding the food whole for consumption. Examples of such foods include: onion, artichoke, garlic, wheat, banana, asparagus, chicory, leek, tomato, bamboo shoots, fruits, vegetables, milk, honey, wheat, rye, barley, corn, oats, tapioca, rice, and potato.

In some embodiments, the method further comprises administering the allergen to the subject. In some embodiments, the allergen is a food allergen. In some embodiments, the composition is administered prior to the allergen. The composition may be administered at least or at most 4, 6, 8, 10, 12, 16, 24, 36, 48, or 72 hours prior to the allergen, or any range or value derivable therein. In some embodiments, the composition is administered after the allergen. The composition may be administered at least or at most 4, 6, 8, 10, 12, 16, 24, 36, 48, or 72 hours after to the allergen, or any range or value derivable therein.

In some embodiments, the method further comprises providing an immunotherapy to the subject. In some embodiments, the immunotherapy is an oral immunotherapy. In some embodiments, the immunotherapy is an epicutaneous immunotherapy. In some embodiments, the immunotherapy is provided prior to administering the composition to the subject. In some embodiments, the immunotherapy is provided after administering the composition to the subject.

Further aspects of the disclosure relate to a method for treating food allergy in a subject comprising providing a food allergy therapy (e.g., an immunotherapy, a steroid, an antihistamine, a hormone, and/or a microbiome-modulating therapy) where the subject was determined to have a food allergy. In some embodiments, the food allergy therapy is a microbiome-modulating therapy. In some embodiments, the microbiome-modulating therapy comprises a composition comprising *Phascolarctobacterium faecium* and/or *Ruminococcus bromii*. In some embodiments, the subject was determined to have a decreased OTU abundance score relative to a control or reference sample, and wherein the OTU abundance score was calculated using at least 20 of the OTUs of Table 1. In some embodiments, the OTU abundance score was calculated using at least or at most, 20, 25, 30, 35, 40, 45, 50, 55, 60, 61, 62, 63, or 64 of the OTUs of Table 1. In some embodiments, the OTU abundance score was calculated using one or more OTUs selected from 173135, 174588, 174818, 176077, 176664, 178799, 186478, 188079, 189816, 190169, 190649, 195258, 196139, 198184, 198941, 2331530, 269611, 295804, 343313, 361702, 362342, 362765, 370099, 4402610, 509709, 556835, 574038, 658370, 823634, New.CleanUp.ReferenceOTU110487, New.CleanUp.ReferenceOTU112566, New.CleanUp.ReferenceOTU122371, New.CleanUp.ReferenceOTU124061, New.CleanUp.ReferenceOTU127991, New.CleanUp.ReferenceOTU1320, New.CleanUp.ReferenceOTU134087, New.CleanUp.ReferenceOTU135990, New.CleanUp.ReferenceOTUl41755, New.CleanUp.ReferenceOTU141972, New.CleanUp.ReferenceOTUl49108, New.CleanUp.ReferenceOTU152821, New.CleanUp.ReferenceOTU153408, New.CleanUp.ReferenceOTU153961, New.CleanUp.ReferenceOTU156924, New.CleanUp.ReferenceOTU164203, New.CleanUp.ReferenceOTU28435, New.CleanUp.ReferenceOTU37938, New.CleanUp.ReferenceOTU41338, New.CleanUp.ReferenceOTU41725, New.CleanUp.ReferenceOTU47134, New.CleanUp.ReferenceOTU5050, New.CleanUp.ReferenceOTU57003, New.CleanUp.ReferenceOTU58395, New.CleanUp.ReferenceOTU58632, New.CleanUp.ReferenceOTU74051, New.CleanUp.ReferenceOTU79183, New.CleanUp.ReferenceOTU80284, New.CleanUp.ReferenceOTU86790, New.CleanUp.ReferenceOTU86928, New.CleanUp.ReferenceOTU89172, New.CleanUp.ReferenceOTU92834, New.CleanUp.ReferenceOTU97550, New.CleanUp.ReferenceOTU99007, New.ReferenceOTU129, and a combination thereof.

In some embodiments, the subject was determined to have a decreased abundance of metabolites from a metabolic pathway, wherein the metabolic pathway is the diacylglycerol pathway, the sterol pathway, the tocopherol metabolism pathway, the gamma-glutamyl amino acid pathway, or the endocannabinoid pathway. In some embodiments, the metabolic pathway is the diacylglycerol pathway. In some embodiments, the subject was determined to have a decreased abundance of linoleoyl-linoleoyl-glycerol (18:2/18:3) relative to a control or reference sample. In some embodiments, the subject was determined to have an increased abundance of metabolites from a metabolic pathway, wherein the metabolic pathway is the creatine metabolism pathway, the dihydroxy fatty acid pathway, the tyrosine metabolism pathway, or the food component/plant metabolism pathway. In some embodiments, the subject was determined to have an increased abundance of secoisolariciresinol relative to a control to reference sample.

Further aspects relate to a method for diagnosing a subject with a food allergy, the method comprising determining the subject to have a decreased OTU abundance score relative to a control or reference sample, wherein the OTU abundance score is calculated using at least 20 of the OTUs of Table 1. In some embodiments, the OTU abundance score is calculated using at least or at most 20, 25, 30, 35, 40, 45, 50, 55, 60, 61, 62, 63, or 64 of the OTUs of Table 1. In some embodiments, the OTU abundance score is calculated using one or more OTUs selected from 173135, 174588, 174818, 176077, 176664, 178799, 186478, 188079, 189816, 190169, 190649, 195258, 196139, 198184, 198941, 2331530, 269611, 295804, 343313, 361702, 362342, 362765, 370099, 4402610, 509709, 556835, 574038, 658370, 823634, New.CleanUp.ReferenceOTU110487, New.CleanUp.ReferenceOTU112566, New.CleanUp.ReferenceOTU122371, New.CleanUp.ReferenceOTU124061, New.CleanUp.ReferenceOTU127991, New.CleanUp.ReferenceOTU1320, New.CleanUp.ReferenceOTU134087, New.CleanUp.ReferenceOTU135990, New.CleanUp.ReferenceOTU141755, New.CleanUp.ReferenceOTUl41972, New.CleanUp.ReferenceOTU149108, New.CleanUp.ReferenceOTU152821, New.CleanUp.ReferenceOTU153408, New.CleanUp.ReferenceOTU153961, New.CleanUp.ReferenceOTU156924, New.CleanUp.ReferenceOTU164203, New.CleanUp.ReferenceOTU28435, New.CleanUp.ReferenceOTU37938, New.CleanUp.ReferenceOTU41338, New.CleanUp.ReferenceOTU41725, New.CleanUp.ReferenceOTU47134, New.CleanUp.ReferenceOTU5050, New.CleanUp.ReferenceOTU57003, New.CleanUp.ReferenceOTU58395, New.CleanUp.ReferenceOTU58632, New.CleanUp.ReferenceOTU74051, New.CleanUp.ReferenceOTU79183, New.CleanUp.ReferenceOTU80284, New.CleanUp.ReferenceOTU86790, New.CleanUp.ReferenceOTU86928, New.CleanUp.ReferenceOTU89172, New.CleanUp.ReferenceOTU92834, New.CleanUp.ReferenceOTU97550, New.CleanUp.ReferenceOTU99007, New.ReferenceOTU129, and a combination thereof.

Yet further aspects of the disclosure are directed to methods for diagnosing a subject with a food allergy, the method comprising determining the subject to have a decreased or increased abundance of metabolites from a metabolic pathway associated with food allergy. In some embodiments, the method comprises determining the subject to have a decreased abundance of metabolites from the diacylglycerol pathway, the sterol pathway, the tocopherol metabolism pathway, the gamma-glutamyl amino acid pathway, and/or the endocannabinoid pathway. In some embodiments, the metabolic pathway is the diacylglycerol pathway. In some embodiments, the subject was determined to have a decreased abundance of linoleoyl-linoleoyl-glycerol (18:2/18:3). In some embodiments, the method comprises determining the subject to have an increased abundance of metabolites from the creatine metabolism pathway, the dihydroxy fatty acid pathway, the tyrosine metabolism pathway, and/or the food component/plant metabolism pathway. In some embodiments, the subject was determined to have an increased abundance of secoisolariciresinol.

Additional aspects relate to a freeze-dried or lyophilized composition comprising *Phascolarctobacterium faecium* and *Ruminococcus bromii*. In some embodiments, the composition does not comprise more than a contaminating amount of any other bacteria. In some embodiments, the composition does not comprise a detectable amount of any other bacteria. In some embodiments, the composition further comprises a pharmaceutical excipient. In some embodiments, the composition comprises one or more additional bacteria. In some embodiments, the composition is formulated for oral administration. Also provided are tablets, capsules, and powders comprising a composition of the disclosure.

Further aspects are directed to a method for determining an OTU abundance score in a subject, the method comprising (a) obtaining a fecal sample from the subject; (b) sequencing nucleic acid from the fecal sample; and (c) identifying OTUs in the fecal sample; wherein the OTUs comprise at least 20 of the OTUs of Table 1. In some embodiments, the OTUs comprise at least 20, at least 25, at least 30, at least 35, at least 40, at least 45, at least 50, at least 55, at least 60, or more of the OTUs of Table 1. In some embodiments, the method further comprises comparing the OTUs in the fecal sample with OTUs from a control or healthy sample. In some embodiments, the method further comprises identifying the subject as having a food allergy if the OTU abundance score is decreased relative to an OTU abundance score of a control or healthy sample.

Yet further aspects are directed to a method for treating a subject determined to have a decreased OTU abundance score relative to a control or healthy sample, the method comprising providing to the subject a composition comprising a therapeutically effective amount of (a) *Phascolarctobacterium faecium* or (b) *Ruminococcus bromii*, wherein the OTU abundance score was determined using at least 20 of the OTUs of Table 1. In some embodiments, the OTUs comprise at least 20, at least 25, at least 30, at least 35, at least 40, at least 45, at least 50, at least 55, at least 60, or more of the OTUs of Table 1.

Throughout this application, the term "about" is used to indicate that a value includes the inherent variation of error for the measurement or quantitation method.

The use of the word "a" or "an" when used in conjunction with the term "comprising" may mean "one," but it is also consistent with the meaning of "one or more," "at least one," and "one or more than one."

The phrase "and/or" means "and" or "or". To illustrate, A, B, and/or C includes: A alone, B alone, C alone, a combination of A and B, a combination of A and C, a combination of B and C, or a combination of A, B, and C. In other words, "and/or" operates as an inclusive or.

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. Compositions and methods "consisting essentially of" any of the ingredients or steps disclosed limits the scope of the claim to the specified materials or steps which do not materially affect the basic and novel characteristic of the claimed invention. The phrase "consisting of" excludes any element, step, or ingredient not specified. It is contemplated that embodiments described in the context of the term "comprising" may also be implemented in the context of the term "consisting of" or "consisting essentially of."

As used herein, the terms "treat," "treatment," "treating," or "amelioration" when used in reference to a disease, disorder or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. For example, a treatment for food allergy is effective if one or more symptoms or clinical markers of food allergy are reduced, such as a reduction in allergic symptoms or immune markers. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, alleviation of one or more symptom(s), diminishment of extent of the deficit, and an increased lifespan as compared to that expected in the absence of treatment.

"Individual, "subject," and "patient" are used interchangeably and can refer to a human or non-human.

The term "isolated" encompasses a bacterium or other entity or substance that has been (1) separated from at least some of the components with which it was associated when initially produced (whether in nature or in an experimental setting), and/or (2) produced, prepared, purified, and/or manufactured by the hand of man. Isolated bacteria may be separated from at least about 10%, about 20%, about 30%, about 40%, about 50%, about 60%, about 70%, about 80%, about 90%, or more of the other components with which they were initially associated. In some embodiments, isolated bacteria are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

The terms "purify," "purifying" and "purified" refer to a bacterium or other material that has been separated from at least some of the components with which it was associated either when initially produced or generated (e.g., whether in nature or in an experimental setting), or during any time after its initial production. A bacterium or a bacterial population may be considered purified if it is isolated at or after production, such as from a material or environment containing the bacterium or bacterial population, and a purified bacterium or bacterial population may contain other materials up to about 10%, about 20%, about 30%, about 40%, about 50%, about 60%, about 70%, about 80%, about 90%, or above about 90% and still be considered "isolated." In some embodiments, purified bacteria and bacterial populations are more than about 80%, about 85%, about 90%, about 91%, about 92%, about 93%, about 94%, about 95%, about 96%, about 97%, about 98%, about 99%, or more than about 99% pure. In the instance of bacterial compositions provided herein, the one or more bacterial types present in the composition can be independently purified from one or more other bacteria produced and/or present in the material or environment containing the bacterial type.

Any method in the context of a therapeutic, diagnostic, or physiologic purpose or effect may also be described in "use" claim language such as "Use of" any compound, composition, or agent discussed herein for achieving or implementing a described therapeutic, diagnostic, or physiologic purpose or effect.

Use of the one or more compositions may be employed based on any of the methods described herein. Other embodiments are discussed throughout this application. Any embodiment discussed with respect to one aspect of the disclosure applies to other aspects of the disclosure as well and vice versa. For example, any step in a method described herein can apply to any other method. Moreover, any method described herein may have an exclusion of any step or combination of steps. The embodiments in the Example section are understood to be embodiments that are applicable to all aspects of the technology described herein.

It is contemplated that any embodiment discussed in this specification can be implemented with respect to any method or composition of the invention, and vice versa. Furthermore, compositions of the invention can be used to achieve methods of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3A shows relative abundance of taxonomy at the family level. Sample IDs are shown on the x-axis (n=34); discordant twins (12 pairs, n=24), for which one member was healthy and the other member was allergic; concordant twins (5 pairs, n=10), for which both members were allergic. Out of 36 total samples in the twin cohort, one sample (S5077) failed sequencing and yielded 0 reads, hence the corresponding twin pair (#13) was excluded from 16S analysis. FIGS. 3B and 3C show correlation of OTU abundance between members from each twin pair, with the comparison between concordant and discordant twin pairs shown in FIG. 3B, and the comparison between dizygotic and monozygotic twins shown in FIG. 3C. Each dot denotes one twin pair (17 pairs shown). FIGS. 3D and 3E show Shannon alpha-diversity index between healthy and allergic groups; all samples are shown in FIG. 3D (n=34) and only discordant twins shown in FIG. 3E (n=24). Each dot denotes one sample. In FIGS. 3B-3E, the bounds of the boxes represent the 25th and 75th percentiles, the horizontal center line indicates the median, and the whiskers extend to data points within a maximum of 1.5 times the interquartile range (IQR). Two-sided Wilcoxon rank-sum test was used in FIGS. 3C-3D and two-sided Wilcoxon signed-rank test was used in FIG. 3E.

In FIG. 7A, DS-FDR was used on all samples (P<0.05) and two-sided Wilcoxon signed-rank test was used on discordant twin pairs (P<0.10), respectively. Unadjusted P-value thresholds were used to filter for OTUs of interest. In FIG. 7B, two-sided Wilcoxon rank-sum test was used on all samples.

FIG. 10A shows results from 28 samples from 14 pairs of monozygotic twins. FIG. 10B shows results from 18 samples from 9 pairs of monozygotic twins that are discordant for food allergy. Each dot denotes one sample. The bounds of the boxes represent the 25th and 75th percentiles, the horizontal center line indicates the median, and the whiskers extend to data points within a maximum of 1.5 times the IQR. DS-FDR was used in FIG. 10A, two-sided Wilcoxon rank-sum test was used in FIG. 10B.

FIG. 13A shows that, of 36 samples, 33 metabolites were more abundant in healthy (n=13) relative to allergic (n=23) group. Metabolites are shown on the row in the format of "COMP_ID|Biochemical_Name|Super_Pathway|Sub_Pathway". Sample IDs are shown on the column, with annotation bars above the heatmap indicating concordant/discordant twin members, sex, and zygosity. FIG. 13B shows that, of 36 samples, 64 metabolites were more abundant in allergic (n=23) relative to healthy (n=13) group. The same annotations are used as in FIG. 13A. In FIGS. 13A and 13B, two-sided Welch's two-sample t-test was used on all samples (P<0.10) and unadjusted P-value thresholds were used to filter for individual metabolites of interest.

FIG. 14A shows that metabolites more abundant in the healthy group or in the allergic group were enriched in different sub-pathways. Relative enrichment fold-change is shown on the x-axis, the name of sub-pathway is shown on the y-axis. P-value and FDR-adjusted P-value of each sub-pathway enrichment are shown next to each horizontal bar. FIGS. 14B and 14C show representative examples of metabolites in the enriched sub pathways in the healthy or allergic group. FIG. 14B shows that the linoleoyl-linolenoyl-glycerol (18:2/18:3) [1]* (sub-pathway: Diacylglycerol) was higher in healthy (n=13) compared to allergic (n=23) twin members. FIG. 14C shows that the secoisolariciresinol (sub-pathway: Food Component/Plant) was higher in allergic twin pairs (n=23) compared to healthy twin pairs (n=13). Each dot denotes one sample. The bounds of the boxes represent the 25th and 75th percentiles, the horizontal center line indicates the median, and the whiskers extend to data points within a maximum of 1.5 times the IQR. In FIG. 14A, hypergeometric test was used to compute the P-values of relative enrichment of metabolite sub-pathways and filtered by FDR-adjusted P<0.10. Pathways consisting of at least 2 significant metabolites were included in the statistical test. After BH-FDR multiple testing correction, diacylglycerol (DAG) remained as the most significantly enriched sub-pathway in metabolites more abundant in healthy twins (FDR-adjusted P<0.00001). In FIGS. 14B and 14C, two-sided Welch's two-sample t-test was used on all samples.

FIG. 20A shows distribution of pathways in group 1 and 2 metabolites. Upper panel: super pathways in each group. The fraction of metabolites from each super pathway on the y-axis was calculated by the number of metabolites that belong to this pathway divided by the total number of metabolites in a group. Bottom panels: number of metabolites that belong to each sub-pathway; (left panel) group 1, (right panel) group 2. FIG. 20B shows that OTU 556835 (family Acidaminococcaceae) is significantly more abundant in healthy compared to allergic group by 16S sequencing. This OTU was annotated as *Phascolarctobacterium faecium* at the species level. FIG. 20C shows quantitative PCR (qPCR) validation of the abundance differences between healthy and allergic groups using *P. faecium*-specific primers. FIG. 20D shows that OTU188079 (family Ruminococcaceae) is significantly more abundant in healthy compared to allergic group by 16S sequencing. This OTU was annotated as *Ruminococcus bromii* at the species level. FIG. 20E shows qPCR validation of the abundance differences between healthy and allergic groups using *R. bromii*-specific primers. Units shown on the y-axis in FIG. 20C and FIG. 20E represent $2^{-Ct}$ normalized to total 16S rRNA copies per gram of fecal material and multiplied by a constant ($1\times10^{22}$) to bring all values above 1. In FIGS. 20B-20E, n=30 samples (15 twin pairs) with DNA available for qPCR validation are shown (10 healthy, 20 allergic). Each dot denotes one sample. The bounds of the boxes represent the 25th and 75th percentiles, the horizontal center line indicates the median, and the whiskers extend to data points within a maximum of 1.5 times the IQR. DS-FDR was used in FIG. 20B and FIG. 20D. In FIG. 20C and FIG. 20E, qPCR data were log 10 transformed, and two-sided Wilcoxon rank-sum test was used.

FIG. 21A shows that OTU 556835 (family Acidaminococcaceae) is significantly more abundant in healthy compared to allergic group by 16S sequencing. This OTU was annotated as *Phascolarctobacterium faecium* at the species level with 99% sequence identity (NCBI accession ID NR_026111.1). P-value was re-calculated amongst the 10 twin pairs shown here from the 16S sequencing data, instead of 12 twin pairs total. FIG. 21B shows quantitative PCR (qPCR) validation of the abundance differences between healthy and allergic groups using *P. faecium*-specific primers. Units shown on the y-axis in represent $2^{-Ct}$ normalized to total 16S rRNA copies per gram of fecal material and multiplied by a constant ($1\times10^{22}$) to bring all values above 1. Samples with abundance above the detection limit in both platforms are shown. Each dot denotes one sample. The bounds of the boxes represent the 25th and 75th percentiles, the horizontal center line indicates the median, and the whiskers extend to data points within a maximum of 1.5 times the IQR. Two-sided Wilcoxon signed-rank test was used in FIGS. 21A and 21B. qPCR data in FIG. 21B were log 10 transformed before statistical testing.

FIG. 22A shows that OTU188079 (family Ruminococcaceae) is significantly more abundant in healthy compared to allergic group by 16S sequencing. This OTU was annotated as *Ruminococcus bromii* at the species level with 99% sequence identity (NCBI accession ID NR_025930.1). P-value was re-calculated amongst the 10 twin pairs shown here from the 16S sequencing data, instead of 12 twin pairs total. FIG. 22B shows qPCR validation of the abundance differences between healthy and allergic groups using *R. bromii*-specific primers. Units shown on the y-axis represent $2^{-Ct}$ normalized to total 16S rRNA copies per gram of fecal material and multiplied by a constant ($1\times10^{22}$) to bring all values above 1. Samples with abundance above the detection limit in both platforms are shown. Each dot denotes one metabolite. The bounds of the boxes represent the 25th and 75th percentiles, the horizontal center line indicates the median, and the whiskers extend to data points within a maximum of 1.5 times the IQR. Two-sided Wilcoxon signed-rank test was used in FIGS. 22A and 22B. qPCR data in FIG. 22B were log 10 transformed before statistical testing.

DETAILED DESCRIPTION

Figure 1:
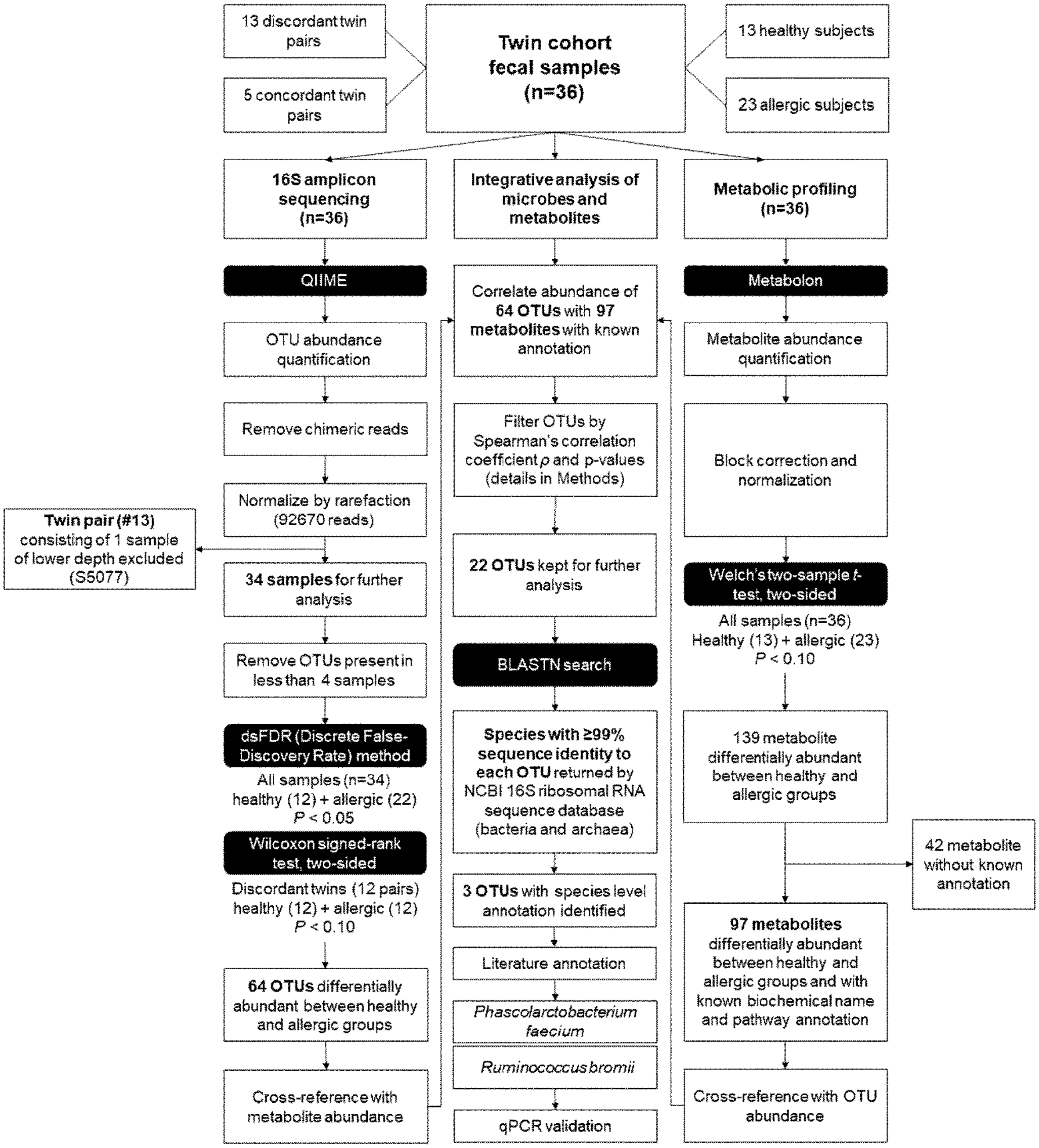
FIG. 1 shows a schematic overview of the analysis workflow on the microbial 16S sequencing data, metabolite profiling data, and integration of the two types of data.

Toward the goal of developing novel microbiome-modulating therapeutics, the inventors identified bacterial taxa, and their products, associated with a healthy microbiota. Fecal samples were examined from a unique cohort of food allergic and healthy twins across a broad age range and a distinct set of bacterial species and metabolites were identified that distinguished the healthy and allergic groups. A unique microbiota signature was identified consisting of 64 operational taxonomic units (OTUs), 62 healthy-abundant and 2 allergic-abundant, that were significantly different between the two groups. By integrating microbiota and metabolite abundance, a significant enrichment was identified in healthy twins in particular metabolite pathways not seen in their allergic counterparts, particularly diacylglycerol, an essential microbially-derived, lipid second messenger involved in numerous cell signaling cascades supporting biosynthesis of glycerolipids and regulating protein kinase C (16). The inventors also identified two bacterial species more abundant in healthy twins which correlate with differentially abundant metabolites: *Phascolarctobacterium faecium*, an acetate/propionate-producing obligate anaerobe associated with increased diacylglycerol and biotin metabolism (17, 18) and *Ruminococcus bromii*, a keystone resistant-starch (RS)-degrading strict anaerobe associated with fatty acid, sterol, and amino acid metabolism (19, 20). These findings demonstrate bacteria and metabolites which may be useful for therapeutic indications in food allergy.

I. Microbial Compositions

Embodiments of the present disclosure concern microbial compositions for the treatment of allergic disease, including food allergy.

The present disclosure also provides pharmaceutical compositions comprising one or more microbial cultures. The bacterial species therefore are present in the dose form as live bacteria, whether in dried or lyophilized form. This may be adapted for suitable administration; for example, in tablet or powder form, in some cases with an enteric coating, for oral treatment.

In some embodiments, the composition is formulated for oral administration. Oral administration may be achieved using a chewable formulation, a dissolving formulation, an encapsulated/coated formulation, a multi-layered lozenge (to separate active ingredients and/or active ingredients and excipients), a slow release/timed release formulation, or other suitable formulations known to persons skilled in the art. Although the word "tablet" is used herein, the formulation may take a variety of physical forms that may commonly be referred to by other terms, such as lozenge, pill, capsule, or the like.

While the compositions of the present disclosure may be formulated for oral administration, other routes of administration can be employed, however, including, but not limited to, subcutaneous, intramuscular, intradermal, transdermal, intraocular, intraperitoneal, mucosal, vaginal, rectal, and intravenous.

The desired dose of the composition of the present disclosure may be presented in multiple (e.g., two, three, four, five, six, or more) sub-doses administered at appropriate intervals throughout the day, week, month or year.

In one aspect, the disclosed composition is prepared as a capsule. The capsule may be a hollow, generally cylindrical capsule formed from various substances, such as gelatin, cellulose, carbohydrate or the like.

In another aspect, the disclosed composition is prepared as a suppository. The suppository may include but is not limited to the bacteria and one or more carriers, such as polyethylene glycol, acacia, acetylated monoglycerides, carnuba wax, cellulose acetate phthalate, corn starch, dibutyl phthalate, docusate sodium, gelatin, glycerin, iron oxides, kaolin, lactose, magnesium stearate, methyl paraben, pharmaceutical glaze, povidone, propyl paraben, sodium benzoate, sorbitan monoleate, sucrose talc, titanium dioxide, white wax and coloring agents.

In some aspects, the disclosed microbial composition is prepared as a tablet. The tablet may include the bacteria and one or more tableting agents, such as dibasic calcium phosphate, stearic acid, croscarmellose, silica, cellulose and cellulose coating. The tablets may be formed using a direct compression process, though those skilled in the art will appreciate that various techniques may be used to form the tablets.

In other aspects, the disclosed microbial composition is formed as food or drink or, alternatively, as an additive to food or drink, wherein an appropriate quantity of bacteria is added to the food or drink to render the food or drink the carrier.

In some embodiments, the microbial composition may further comprise a food or a nutritional supplement effective to stimulate the growth of bacteria (e.g., *Phascolarctobacterium faecium, Ruminococcus bromii*, and/or *Agathobaculum desmolans*) present in the gastrointestinal tract of the subject. In some embodiments, the nutritional supplement is produced by another bacterium associated with a healthy human gut microbiome.

In some embodiments, the disclosed microbial compositions comprise one or more microparticles. In some embodiments, the compositions comprise one or more bacteria (e.g., *Phascolarctobacterium faecium, Ruminococcus bromii*, and/or *Agathobaculum desmolans*) encapsulated within microparticles. Microparticles may be any type of microparticles suitable for providing a microbial composition to a subject. In some embodiments, microparticles are lipid microparticles.

In some embodiments, a microbial composition comprises an isolated bacteria selected from *Phascolarctobacterium faecium, Ruminococcus bromii* and *Agathobaculum desmolans*. In some embodiments, a microbial composition comprises *Phascolarctobacterium faecium* and *Ruminococcus bromii*. In some embodiments, a microbial composition comprises *Phascolarctobacterium faecium* and *Agathobaculum desmolans*. In some embodiments, a microbial composition comprises *Agathobaculum desmolans* and *Ruminococcus bromii*. In some embodiments, a microbial composition comprises a minimum amount of one or more isolated bacteria. For example, a microbial composition may comprise at least, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.9% of a particular type or particular types of bacteria (e.g., *Phascolarctobacterium faecium, Ruminococcus bromii*, and/or *Agathobaculum desmolans*), or any value or range derivable therein. In some embodiments, a microbial composition comprises at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.9% of *Phascolarctobacterium faecium*, or any value or range derivable therein. In some embodiments, a microbial composition comprises at least %, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.9% of *Agathobaculum desmolans*, or any value or range derivable therein. In some embodiments, a microbial composition comprises at least %, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.9% of *Ruminococcus bromii*, or any value or range derivable therein. In some embodiments, a microbial composition comprises at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.9% of *Phascolarctobacterium faecium* and *Agathobaculum desmolans*, or any value or range derivable therein. In some embodiments, a microbial composition comprises at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.9% of *Phascolarctobacterium faecium* and *Ruminococcus bromii*, or any value or range derivable therein. In some embodiments, a microbial composition comprises at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 8100, 82%, 83%, 84%, 85%, 86%, 87%, 88%, 89%, 90%, 91%, 92%, 93%, 94%, 95%, 96%, 97%, 98%, 99%, 99.5%, or 99.9% of *Ruminococcus bromii* and *Agathobaculum desmolans*, or any value or range derivable therein.

In some embodiments, a microbial composition comprises, in addition to *Phascolarctobacterium faecium, Ruminococcus bromii*, and/or *Agathobaculum desmolans*, one or more additional bacteria. In some embodiments, a microbial composition does not comprise a detectable amount of one or more additional bacteria. In some embodiments, a microbial composition does not comprise more than a contaminating amount of one or more additional bacteria. A contaminating amount of bacteria in a composition may be at most 5%, 4%, 3%, 2%, 1%, 0.1%, 0.01%, 0.001%, or 0.0001% of the composition, or any range or value derivable therein.

II. Sample Preparation

In certain aspects, methods involve obtaining a sample from a subject (also a "biological sample"). The methods of obtaining provided herein may include methods of biopsy such as fine needle aspiration, core needle biopsy, vacuum assisted biopsy, incisional biopsy, excisional biopsy, punch biopsy, shave biopsy or skin biopsy. In other embodiments the sample may be obtained from any of the tissues provided herein that include but are not limited to non-cancerous or cancerous tissue and non-cancerous or cancerous tissue from the serum, gall bladder, mucosal, skin, heart, lung, breast, pancreas, blood, liver, muscle, kidney, smooth muscle, bladder, colon, intestine, brain, prostate, esophagus, or thyroid tissue. Alternatively, the sample may be obtained from any other source including but not limited to blood, sweat, hair follicle, buccal tissue, tears, menses, feces, or saliva. In certain aspects of the current methods, any medical professional such as a doctor, nurse or medical technician may obtain a biological sample for testing. Yet further, the biological sample can be obtained without the assistance of a medical professional.

A sample may include but is not limited to, tissue, cells, or biological material from cells or derived from cells of a subject. The biological sample may be a heterogeneous or homogeneous population of cells or tissues. The biological sample may be obtained using any method known to the art that can provide a sample suitable for the analytical methods described herein. The sample may be obtained by non-invasive methods including but not limited to: scraping of the skin or cervix, swabbing of the cheek, saliva collection, urine collection, feces collection, collection of menses, tears, or semen.

The sample may be obtained by methods known in the art. In certain embodiments the samples are obtained by biopsy. In other embodiments the sample is obtained by swabbing, endoscopy, scraping, phlebotomy, or any other methods known in the art. In some cases, the sample may be obtained, stored, or transported using components of a kit of the present methods. In some cases, multiple samples, such as multiple fecal samples may be obtained for diagnosis by the methods described herein. In other cases, multiple samples, such as one or more samples of one type (for example fecal) and one or more samples of another type (for example blood) may be obtained for diagnosis by the methods. In some cases, multiple samples may be obtained at the same or different times. Samples may be obtained at different times are stored and/or analyzed by different methods. For example, a sample may be obtained and analyzed by routine staining methods or any other cytological analysis methods.

In some embodiments the biological sample may be obtained by a physician, nurse, or other medical professional such as a medical technician, endocrinologist, cytologist, phlebotomist, radiologist, or a pulmonologist. The medical professional may indicate the appropriate test or assay to perform on the sample. In certain aspects a molecular profiling business may consult on which assays or tests are most appropriately indicated. In further aspects of the current methods, the patient or subject may obtain a biological sample for testing without the assistance of a medical professional, such as obtaining a whole blood sample, a urine sample, a fecal sample, a buccal sample, or a saliva sample.

In other cases, the sample is obtained by an invasive procedure including but not limited to: biopsy, needle aspiration, endoscopy, or phlebotomy. The method of needle aspiration may further include fine needle aspiration, core needle biopsy, vacuum assisted biopsy, or large core biopsy. In some embodiments, multiple samples may be obtained by the methods herein to ensure a sufficient amount of biological material.

General methods for obtaining biological samples are also known in the art. Publications such as Ramzy, Ibrahim Clinical Cytopathology and Aspiration Biopsy 2001, which is herein incorporated by reference in its entirety, describes general methods for biopsy and cytological methods. In one embodiment, the sample is a fecal sample. In some cases, the fine needle aspirate sampling procedure may be guided by the use of an ultrasound, X-ray, or other imaging device.

In some embodiments of the present methods, the molecular profiling business may obtain the biological sample from a subject directly, from a medical professional, from a third party, or from a kit provided by a molecular profiling business or a third party. In some cases, the biological sample may be obtained by the molecular profiling business after the subject, a medical professional, or a third party acquires and sends the biological sample to the molecular profiling business. In some cases, the molecular profiling business may provide suitable containers, and excipients for storage and transport of the biological sample to the molecular profiling business.

In some embodiments of the methods described herein, a medical professional need not be involved in the initial diagnosis or sample acquisition. An individual may alternatively obtain a sample through the use of an over the counter (OTC) kit. An OTC kit may contain a means for obtaining said sample as described herein, a means for storing said sample for inspection, and instructions for proper use of the kit. In some cases, molecular profiling services are included in the price for purchase of the kit. In other cases, the molecular profiling services are billed separately. A sample suitable for use by the molecular profiling business may be any material containing tissues, cells, nucleic acids, genes, gene fragments, expression products, gene expression products, or gene expression product fragments of an individual to be tested. Methods for determining sample suitability and/or adequacy are provided.

In some embodiments, the subject may be referred to a specialist such as an oncologist, surgeon, endocrinologist, or gastroenterologist. The specialist may likewise obtain a biological sample for testing or refer the individual to a testing center or laboratory for submission of the biological sample. In some cases the medical professional may refer the subject to a testing center or laboratory for submission of the biological sample. In other cases, the subject may provide the sample. In some cases, a molecular profiling business may obtain the sample.

III. Administration of Therapeutic Compositions

Embodiments of the disclosure relate to compositions and methods comprising therapeutic compositions. Different therapies may be administered in one composition or in more than one composition, such as 2 compositions, 3 compositions, or 4 compositions. Various combinations of the agents may be employed.

In some embodiments, the therapy provided herein comprises administration of a combination of therapeutic agents, such as a combination of two or more microbial compositions. In some embodiments, the therapy comprises administration of a combination or one or more microbial compositions and a prebiotic. In some embodiments, the therapy comprises administration of a combination of one or more microbial compositions and an allergen. For example, a therapy may comprise administration of one or more bacteria and a food of a food allergy (e.g., administration of bacteria and a peanut product to an individual with a peanut allergy). The therapy may be administered in any suitable manner known in the art. For example, a microbial composition, a prebiotic, and/or an allergen may be administered sequentially (at different times) or concurrently (at the same time).

Embodiments of the disclosure relate to compositions and methods comprising bacteria, a food allergen, and/or one or more prebiotics. The bacteria, allergen, and/or prebiotic(s) may be administered in one composition or in more than one composition, such as 2 compositions, 3 compositions, or 4 compositions. Various combinations of the agents may be employed, for example, a bacterium (or composition comprising bacteria) is "A" and a prebiotic or an allergen is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A B/A/B/A B/A/A/B A/A/A/B B/A/A/A A/B/A/A A/A/B/A

In some embodiments, the microbial composition is administered prior to the prebiotic. In some embodiments, the microbial composition is administered at least, at most, or about 1, 2, 3, 5, 6, 12, 24 hours or 2, 3, 4, 6, 8, 10, days or 2, 3, 4, 5, 6, 7, or 8 weeks (or any derivable range therein) prior to the prebiotic. In some embodiments, at least 1, 2, 3, 4, 5, 6, or 7 doses (or any derivable range therein) of the microbial composition is administered at least, at most, or about 1, 2, 3, 5, 6, 12, 24 hours or 2, 3, 4, 6, 8, 10, days or 2, 3, 4, 5, 6, 7, or 8 weeks (or any derivable range therein) prior to the prebiotic. In some embodiments, the microbial composition is administered after the prebiotic. In some embodiments, the microbial composition is administered at least, at most, or about 1, 2, 3, 5, 6, 12, 24 hours or 2, 3, 4, 6, 8, 10, days or 2, 3, 4, 5, 6, 7, or 8 weeks (or any derivable range therein) after the prebiotic or after at least one of the prebiotics or after at least 2 of the prebiotics. In some embodiments, at least 1, 2, 3, 4, 5, 6, or 7 doses (or any derivable range therein) of the microbial composition is administered at least, at most, or about 1, 2, 3, 5, 6, 12, 24 hours or 2, 3, 4, 6, 8, 10, days or 2, 3, 4, 5, 6, 7, or 8 weeks (or any derivable range therein) after the prebiotic or after at least one of the prebiotics or after at least 2 of the prebiotics.

In some embodiments, the microbial composition is administered prior to the allergen. In some embodiments, the microbial composition is administered at least, at most, or about 1, 2, 3, 5, 6, 12, 24 hours or 2, 3, 4, 6, 8, 10, days or 2, 3, 4, 5, 6, 7, or 8 weeks (or any derivable range therein) prior to the allergen. In some embodiments, at least 1, 2, 3, 4, 5, 6, or 7 doses (or any derivable range therein) of the microbial composition is administered at least, at most, or about 1, 2, 3, 5, 6, 12, 24 hours or 2, 3, 4, 6, 8, 10, days or 2, 3, 4, 5, 6, 7, or 8 weeks (or any derivable range therein) prior to the allergen. In some embodiments, the microbial composition is administered after the allergen. In some embodiments, the microbial composition is administered at least, at most, or about 1, 2, 3, 5, 6, 12, 24 hours or 2, 3, 4, 6, 8, 10, days or 2, 3, 4, 5, 6, 7, or 8 weeks (or any derivable range therein) after the allergen. In some embodiments, at least 1, 2, 3, 4, 5, 6, or 7 doses (or any derivable range therein) of the microbial composition is administered at least, at most, or about 1, 2, 3, 5, 6, 12, 24 hours or 2, 3, 4, 6, 8, 10, days or 2, 3, 4, 5, 6, 7, or 8 weeks (or any derivable range therein) after the allergen.

In some embodiments, the microbial modulator composition is formulated for oral administration. The skilled artisan knows a variety of formulas which can encompass living or killed microorganisms and which can present as food supplements (e.g., pills, tablets, powders, and the like) or as functional food such as drinks or fermented yogurts.

The agents of the disclosure may be administered by the same route of administration or by different routes of administration. In some embodiments, the prebiotic is administered intravenously, intramuscularly, subcutaneously, topically, orally, transdermally, intraperitoneally, intraorbitally, by implantation, by inhalation, intrathecally, intraventricularly, or intranasally. In some embodiments, the microbial composition is administered intravenously, intramuscularly, subcutaneously, topically, orally, transdermally, intraperitoneally, intraorbitally, by implantation, by inhalation, intrathecally, intraventricularly, or intranasally. The appropriate dosage may be determined based on the type of disease to be treated, severity and course of the disease, the clinical condition of the individual, the individual's clinical history and response to the treatment, and the discretion of the attending physician.

In some embodiments, a composition may comprise a therapeutically effective amount of one or more bacteria. As used here, a "therapeutically effective" amount of a bacterium describes an amount sufficient to be effective in treating a desired condition, for example food allergy. In some embodiments, a therapeutically effective amount of each of the at least one isolated or purified population of bacteria or each of the at least two, 3, 4, 5, 6, 7, 8, 9, 10 11, 12, 13, 14, or 15 isolated or purified populations of bacteria that is administered to a human will be at least about $1\times10^3$ colony forming units (CFU) of bacteria or at least about $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ CFU (or any derivable range therein). In some embodiments, a single dose will contain bacteria (such as a specific bacteria or species, genus, or family described herein) present in an amount of least, at most, or about $1\times10^{3}$, $1\times10^{4}$, $1\times10^{5}$, $1\times10^{6}$, $1\times10^{7}$, $1\times10^{8}$, $1\times10^{9}$, $1\times10^{10}$, $1\times10^{11}$, $1\times10^{12}$, $1\times10^{13}$, $1\times10^{14}$, $1\times10^{15}$ or more CFU (or any derivable range therein). In some embodiments, a single dose will contain at least, at most, or about $1\times10^{3}$, $1\times10^{4}$, $1\times10^{5}$, $1\times10^{6}$, $1\times10^{7}$, $1\times10^{8}$, $1\times10^{9}$, $1\times10^{10}$, $1\times10^{11}$, $1\times10^{12}$, $1\times10^{13}$, $1\times10^{14}$, $1\times10^{15}$ or greater than $1\times10^{15}$ CFU (or any derivable range therein) of total bacteria.

In some embodiments, a therapeutically effective amount of each of the at least one isolated or purified population of bacteria that is administered to a human will be at least about $1\times10^{3}$ cells of bacteria or at least about $1\times10^{4}$, $1\times10^{5}$, $1\times10^{6}$, $1\times10^{7}$, $1\times10^{8}$, $1\times10^{9}$, $1\times10^{10}$, $1\times10^{11}$, $1\times10^{12}$, $1\times10^{13}$, $1\times10^{14}$, $1\times10^{15}$ cells (or any derivable range therein). In some embodiments, a single dose will contain bacteria (such as a specific bacteria or species, genus, or family described herein) present in an amount of at least, at most, or about $1\times10^{3}$, $1\times10^{4}$, $1\times10^{5}$, $1\times10^{6}$, $1\times10^{7}$, $1\times10^{8}$, $1\times10^{9}$, $1\times10^{10}$, $1\times10^{11}$, $1\times10^{12}$, $1\times10^{13}$, $1\times10^{14}$, $1\times10^{15}$ or more cells (or any derivable range therein). In some embodiments, a single dose will contain at least, at most, or about $1\times10^{3}$, $1\times10^{4}$, $1\times10^{5}$, $1\times10^{6}$, $1\times10^{7}$, $1\times10^{8}$, $1\times10^{9}$, $1\times10^{10}$, $1\times10^{11}$, $1\times10^{2}$, $1\times10^{13}$, $1\times10^{14}$, $1\times10^{15}$ or greater than $1\times10^{15}$ cells (or any derivable range therein) of total bacteria.

Embodiments of the disclosure relate to compositions and methods comprising one or more metabolites. In some embodiments, disclosed are compositions comprising one or more metabolites from a metabolic pathway. In some embodiments, the metabolic pathway is the diacylglycerol pathway, the biotin metabolism pathway, the sterol pathway, the tocopherol metabolism pathway, the gamma-glutamyl amino acid pathway, or the endocannabinoid pathway. In some embodiments, the disclosed compositions comprise one or more metabolites from the diacylglycerol pathway. In some embodiments, the disclosed compositions comprise linoleoyl-linoleoyl-glycerol (18:2/18:3). In some embodiments, the disclosed compositions comprise diacylglycerol. In some embodiments, the metabolic pathway is the creatine metabolism pathway, the dihydroxy fatty acid pathway, the cardiovascular drug metabolism pathway, the tyrosine metabolism pathway, or the food component/plant metabolism pathway. In some embodiments, the disclosed compositions comprise secoisolariciresinol. Also contemplated are compositions comprising inhibitors or activators of one of more metabolic pathways disclosed above. For example, in some embodiments, a composition comprises an activator of the diacylglycerol pathway, the biotin metabolism pathway, the sterol pathway, the tocopherol metabolism pathway, the gamma-glutamyl amino acid pathway, or the endocannabinoid pathway. In some embodiments, a composition comprises an activator of the diacylglycerol pathway. In some embodiments, a composition comprises an inhibitor of the creatine metabolism pathway, the hydroxy fatty acid pathway, the cardiovascular drug metabolism pathway, the tyrosine metabolism pathway, or the food component/plant metabolism pathway. In some embodiments, a composition comprises an inhibitor of the creatine metabolism pathway.

The treatments may include various "unit doses." Unit dose is defined as containing a predetermined-quantity of the therapeutic composition. The quantity to be administered, and the particular route and formulation, is within the skill of determination of those in the clinical arts. A unit dose need not be administered as a single injection but may comprise continuous infusion over a set period of time. In some embodiments, a unit dose comprises a single administrable dose.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability and toxicity of the particular therapeutic substance or other therapies a subject may be undergoing.

Prebiotics may be formulated using techniques of pharmaceutical formulation known in the art. They may be formulated using specialized techniques known for delivery to specific regions of the gastrointestinal tract. Two examples known in the art are described in published PCT application WO 2018/195067 A1 and also in US Patent application publication US 2017/0209504 A1, each of which are incorporated by reference. Other formulations for prebiotics or combinations of prebiotics and bacteria (e.g., *Phascolarctobacterium faecium, Ruminococcus bromii*, and/or *Agathobaculum desmolans*) are known in the art. In some embodiments, the compositions of the disclosure include a compound carrying butyrate or other microbial metabolites, such as those described in WO 2018/195067.

IV. Methods of Treatment

The methods of the disclosure relate to the treatment of inflammatory, autoimmune, or allergic disease. In some embodiments, the methods and compositions are for the treatment of a food allergy. In some embodiments, the food allergy is an allergy to one or more of peanuts, tree nuts, shellfish, soy, egg, fish, mustard, oats, olives, corn, rice, pineapple, wheat, gluten, milk, sesame, garbanzo beans, bananas, kiwi, avocado, mangos, melons, carrots, cucumber, apples, squash, and crab. In some embodiments, the disclosed methods comprise treatment of a subject having an allergy to a single food. In some embodiments, the disclosed methods comprise treatment of a subject having allergies to multiple foods (e.g., 1, 2, 3, 4, 5, 6, 7, or 8 foods, or more). In some embodiments, subjects treated by the disclosed methods have been diagnosed with a food allergy. In some embodiments, subjects treated by the disclosed methods have not been diagnosed with a food allergy. In some embodiments, subjects treated by the disclosed methods are at risk for having or developing an allergy to one or more foods.

In some embodiments, the disclosed methods comprise treatment of a subject following identification and/or analysis of one or more operational taxonomic units (OTUs). OTUs describe clusters of similar sequence results (e.g., from sequencing of 16S rRNA from a biological sample comprising a plurality of bacteria) based on a sequence similarity threshold (e.g., 97% similar, 98% similar, or 99% similar). OTUs may be further characterized to determine the closest matching genus or species. OTUs may be used to identify a subject as having a food allergy and/or inform a food allergy treatment decision. Examples of OTUs which may be used in the methods of the present disclosure are provided in Table 1.

TABLE 1

List of 64 OTUs identified herein as differentially abundant between healthy and allergic twins.

| OTU | Taxonomy |
| --- | --- |
| 173135 | *k__Bacteria*; *p__Firmicutes*; |

TABLE 1-continued

List of 64 OTUs identified herein as differentially abundant between healthy and allergic twins.

| OTU | Taxonomy |
|---|---|
| | c__Clostridia; o__Clostridiales; f__Ruminococcaceae; g__; s__ |
| 174588 | k__Bacteria; p__Firmicutes; c__Clostridia; o__Clostridiales; f__Lachnospiraceae; g__; s__ |
| 174818 | k__Bacteria; p__Firmicutes; c__Clostridia; o__Clostridiales; f__Ruminococcaceae; g__; s__ |
| 176077 | k__Bacteria; p__Firmicutes; c__Clostridia; o__Clostridiales; f__; g__; s__ |
| 176664 | k__Bacteria; p__Firmicutes; c__Clostridia; o__Clostridiales; f__Lachnospiraceae; g__Roseburia; s__faecis |
| 178799 | k__Bacteria; p__Firmicutes; c__Clostridia; o__Clostridiales; f__Ruminococcaceae; g__; s__ |
| 186478 | k__Bacteria; p__Firmicutes; c__Clostridia; o__Clostridiales; f__Ruminococcaceae; g__; s__ |
| 188079 | k__Bacteria; p__Firmicutes; c__Clostridia; o__Clostridiales; f__Ruminococcaceae; g__Ruminococcus |
| 189816 | k__Bacteria; p__Firmicutes; c__Clostridia; o__Clostridiales |
| 190169 | k__Bacteria; p__Firmicutes; c__Clostridia; o__Clostridiales; f__Ruminococcaceae; g__; s__ |
| 190649 | k__Bacteria; p__Firmicutes; c__Clostridia; o__Clostridiales; f__Ruminococcaceae; g__; s__ |
| 195258 | k__Bacteria; p__Bacteroidetes; c__Bacteroidia; o__Bacteroidales; f__Bacteroidaceae; g__Bacteroides; s__ovatus |
| 196139 | k__Bacteria; p__Firmicutes; c__Clostridia; o__Clostridiales; f__Ruminococcaceae; g__; s__ |

TABLE 1-continued

List of 64 OTUs identified herein as differentially abundant between healthy and allergic twins.

| OTU | Taxonomy |
|---|---|
| 198184 | k__Bacteria; p__Firmicutes; c__Clostridia; o__Clostridiales; f__Ruminococcaceae; g__; s__ |
| 198941 | k__Bacteria; p__Firmicutes; c__Clostridia; o__Clostridiales; f__Ruminococcaceae; g__; s__ |
| 2331530 | k__Bacteria; p__Bacteroidetes; c__Bacteroidia; o__Bacteroidales; f__Bacteroidaceae; g__Bacteroides; s__uniformis |
| 269611 | k__Bacteria; p__Firmicutes; c__Clostridia; o__Clostridiales; f__Ruminococcaceae; g__; s__ |
| 295804 | k__Bacteria; p__Firmicutes; c__Clostridia; o__Clostridiales; f__Lachnospiraceae; g__Roseburia; s__ |
| 343313 | k__Bacteria; p__Firmicutes; c__Clostridia; o__Clostridiales; f__Ruminococcaceae; g__; s__ |
| 361702 | k__Bacteria; p__Firmicutes; c__Clostridia; o__Clostridiales; f__Ruminococcaceae; g__Ruminococcus; s__ |
| 362342 | k__Bacteria; p__Firmicutes; c__Clostridia; o__Clostridiales; f__Ruminococcaceae; g__Ruminococcus; s__ |
| 362765 | k__Bacteria; p__Firmicutes; c__Clostridia; o__Clostridiales; f__Ruminococcaceae; g__Ruminococcus; s__ |
| 370099 | k__Bacteria; p__Firmicutes; c__Erysipelotrichi; o__Erysipelotrichales; f__Erysipelotrichaceae; g__; s__ |
| 4402610 | k__Bacteria; p__Bacteroidetes; c__Bacteroidia; o__Bacteroidales; f__[Odoribacteraceae]; g__Butyricimonas; s__ |
| 509709 | k__Bacteria; p__Firmicutes; c__Clostridia; o__Clostridiales; f__Lachnospiraceae; g__Dorea; s__ |
| 556835 | k__Bacteria; p__Firmicutes; c__Clostridia; |

TABLE 1-continued

List of 64 OTUs identified herein as differentially abundant between healthy and allergic twins.

| OTU | Taxonomy |
|---|---|
| | *o__Clostridiales*; *f__Veillonellaceae*; *g__Phascolarcto-bacterium*; s__ |
| 574038 | *k__Bacteria*; *p__Firmicutes*; *c__Clostridia*; *o__Clostridiales*; *f__Lachnospiraceae*; g__; s__ |
| 658370 | *k__Bacteria*; *p__Firmicutes*; *c__Clostridia*; *o__Clostridiales*; *f__Lachnospiraceae*; g__; s__ |
| 823634 | *k__Bacteria*; *p__Firmicutes*; *c__Clostridia*; *o__Clostridiales*; *f__Ruminococcaceae*; *g__Ruminococcus*; *s__bromii* |
| New.CleanUp.Reference OTU110487 | *k__Bacteria*; *p__Firmicutes*; *c__Clostridia*; *o__Clostridiales*; *f__Ruminococcaceae*; *g__Ruminococcus*; s__ |
| New.CleanUp.Reference OTU112566 | *k__Bacteria*; *p__Bacteroidetes*; *c__Bacteroidia*; *o__Bacteroidales*; *f__Bacteroidaceae*; *g__Bacteroides*; *s__uniformis* |
| New.Cleanup.Reference OTU122371 | *k__Bacteria*; *p__Firmicutes*; *c__Clostridia*; *o__Clostridiales*; *f__Lachnospiraceae*; g__; s__ |
| New.CleanUp.Reference OTU124061 | *k__Bacteria*; *p__Firmicutes*; *c__Clostridia*; *o__Clostridiales*; *f__Lachnospiraceae*; g__; s__ |
| New.CleanUp.Reference OTU127991 | *k__Bacteria*; *p__Firmicutes*; *c__Clostridia*; *o__Clostridiales*; *f__Ruminococcaceae*; *g__Ruminococcus*; s__ |
| New.CleanUp.Reference OTU1320 | *k__Bacteria*; *p__Firmicutes*; *c__Clostridia*; *o__Clostridiales*; *f__Ruminococcaceae*; *g__aecalibacterium*; *s__prausnitzii* |
| New.CleanUp.Reference OTU134087 | *k__Bacteria*; *p__Firmicutes*; *c__Clostridia*; *o__Clostridiales*; *f__Lachnospiraceae*; g__; s__ |
| New.CleanUp.Reference OTU135990 | *k__Bacteria*; *p__Firmicutes*; *c__Clostridia*; *o__Clostridiales*; *f__Lachnospiraceae*; *g__Coprococcus*; s__ |
| New.CleanUp.Reference OTU141755 | *k__Bacteria*; *p__Firmicutes*; *c__Clostridia*; *o__Clostridiales*; *f__Lachnospiraceae* |

TABLE 1-continued

List of 64 OTUs identified herein as differentially abundant between healthy and allergic twins.

| OTU | Taxonomy |
|---|---|
| New.CleanUp.Reference OTU141972 | *k__Bacteria*; *p__Firmicutes*; *c__Clostridia*; *o__Clostridiales*; *f__Ruminococcaceae*; *g__Ruminococcus*; s__ |
| New.CleanUp.Reference OTU149108 | *k__Bacteria*; *p__Firmicutes*; *c__Clostridia*; *o__Clostridiales*; *f__Lachnospiraceae*; *g__Lachnospira*; s__ |
| New.CleanUp.Reference OTU152821 | *k__Bacteria*; *p__Firmicutes*; *c__Clostridia*; *o__Clostridiales*; f__; g__; s__ |
| New.CleanUp.Reference OTU153408 | *k__Bacteria*; *p__Bacteroidetes*; *c__Bacteroidia*; *o__Bacteroidales*; *f__Bacteroidaceae*; *g__Bacteroides*; *s__uniformis* |
| New.CleanUp.Reference OTU153961 | *k__Bacteria*; *p__Firmicutes*; *c__Clostridia*; *o__Clostridiales*; *f__Ruminococcaceae* |
| New.CleanUp.Reference OTU156924 | *k__Bacteria*; *p__Bacteroidetes*; *c__Bacteroidia*; *o__Bacteroidales*; *f__Bacteroidaceae*; *g__Bacteroides*; s__ |
| New.CleanUp.Reference OTU164203 | *k__Bacteria*; *p__Firmicutes*; *c__Clostridia*; *o__Clostridiales*; *f__Ruminococcaceae*; *g__Oscillospira*; s__ |
| New.CleanUp.Reference OTU28435 | *k__Bacteria*; *p__Firmicutes*; *c__Clostridia*; *o__Clostridiales*; *f__Lachnospiraceae*; *g__Coprococcus*; s__ |
| New.CleanUp.Reference OTU37938 | *k__Bacteria*; *p__Firmicutes*; *c__Clostridia*; *o__Clostridiales*; *f__Lachnospiraceae*; *g__Blautia*; s__ |
| New.CleanUp.Reference OTU41338 | *k__Bacteria*; *p__Firmicutes*; *c__Clostridia*; *o__Clostridiales*; *f__Ruminococcaceae*; *g__Ruminococcus*; *s__bromii* |
| New.CleanUp.Reference OTU41725 | *k__Bacteria*; *p__Firmicutes*; *c__Clostridia*; *o__Clostridiales*; f__; g__; s__ |
| New.CleanUp.Reference OTU47134 | *k__Bacteria*; *p__Firmicutes*; *c__Clostridia*; *o__Clostridiales*; *f__Ruminococcaceae* |
| New.CleanUp.Reference OTU5050 | *k__Bacteria*; *p__Firmicutes*; *c__Clostridia*; *o__Clostridiales*; *f__Lachnospiraceae*; |

TABLE 1-continued

List of 64 OTUs identified herein as differentially abundant between healthy and allergic twins.

| OTU | Taxonomy |
|---|---|
| | g__*Lachnospira*; s__ |
| New.CleanUp.Reference OTU57003 | k__*Bacteria*; p__*Firmicutes*; c__*Clostridia*; o__*Clostridiales*; f__*Lachnospiraceae*; g__*Coprococcus*; s__ |
| New.CleanUp.Reference OTU58395 | k__*Bacteria*; p__*Firmicutes*; c__*Clostridia*; o__*Clostridiales*; f__*Lachnospiraceae*; g__*Coprococcus*; s__ |
| New.CleanUp.Reference OTU58632 | k__*Bacteria*; p__*Firmicutes*; c__*Clostridia*; o__*Clostridiales*; f__*Ruminococcaceae*; g__*Ruminococcus*; s__ |
| New.CleanUp.Reference OTU74051 | k__*Bacteria*; p__*Firmicutes*; c__*Clostridia*; o__*Clostridiales*; f__*Ruminococcaceae*; g__*Faecalibacterium*; s__*prausnitzii* |
| New.CleanUp.Reference OTU79183 | k__*Bacteria*; p__*Firmicutes*; c__*Clostridia*; o__*Clostridiales*; f__*Lachnospiraceae*; g__; s__ |
| New.CleanUp.Reference OTU80284 | k__*Bacteria*; p__*Firmicutes*; c__*Clostridia*; o__*Clostridiales*; f__*Lachnospiraceae*; g__; s__ |
| New.CleanUp.Reference OTU86790 | k__*Bacteria*; p__*Firmicutes*; c__*Clostridia*; o__*Clostridiales*; f__*Lachnospiraceae*; g__; s__ |
| New.CleanUp.Reference OTU86928 | k__*Bacteria*; p__*Firmicutes*; c__*Clostridia*; o__*Clostridiales*; f__*Ruminococcaceae*; g__*Faecalibacterium*; s__*prausnitzii* |
| New.CleanUp.Reference OTU89172 | k__*Bacteria*; p__*Firmicutes*; c__*Clostridia*; o__*Clostridiales*; f__*Lachnospiraceae*; g__*Coprococcus*; s__ |
| New.CleanUp.Reference OTU92834 | k__*Bacteria*; p__*Firmicutes*; c__*Clostridia*; o__*Clostridiales*; f__*Ruminococcaceae*; g__*Oscillospira*; s__ |
| New.CleanUp.Reference OTU97550 | k__*Bacteria*; p__*Firmicutes*; c__*Clostridia*; o__*Clostridiales*; f__*Lachnospiraceae*; g__; s__ |
| New.CleanUp.Reference OTU99007 | k__*Bacteria*; p__*Bacteroidetes*; c__*Bacteroidia*; o__*Bacteroidales*; f__*Porphyromonadaceae*; g__*Parabacteroides*; s__ |
| New.ReferenceOTU129 | k__*Bacteria*; p__*Bacteroidetes*; c__*Bacteroidia*; o__*Bacteroidales*; f__*Bacteroidaceae*; g__*Bacteroides*; s__ |

Aspects of the disclosure comprise determining an "OTU abundance score". An OTU abundance score may be determined to diagnose a subject with a food allergy and/or to identify a patient as a candidate for food allergy therapy. An OTU abundance score may be calculated from two or more OTUs, such as the OTUs listed in Table 1. In some embodiments, an OTU abundance score is calculated using 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64 of the OTUs listed in Table 1. In some embodiments, an OTU abundance score is calculated by first adding a rarefied absolute count matrix of OTUs by offset 1.0 and log 10-transforming, then scaling by dividing the value by their root mean square across samples. The abundance of allergic-abundant OTUs is multiplied by (−1).

In some embodiments, the disclosed methods are for treating allergies, asthma, diabetes (e.g. type 1 diabetes), graft rejection, arthritis (rheumatoid arthritis such as acute arthritis, chronic rheumatoid arthritis, gout or gouty arthritis, acute gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, and systemic juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, rheumatoid spondylitis, rheumatoid synovitis, hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, proliferative nephritis, autoimmune polyglandular endocrine failure, balanitis including balanitis circumscripta plasmacellularis, balanoposthitis, erythema annulare centrifugum, erythema dyschromicum perstans, eythema multiform, granuloma annulare, lichen nitidus, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, allergic reaction, eczema including allergic or atopic eczema, asteatotic eczema, dyshidrotic eczema, and vesicular palmoplantar eczema, asthma such as asthma bronchiale, bronchial asthma, and auto-immune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, systemic lupus erythematosus (SLE) such as cutaneous SLE or subacute cutaneous SLE, neonatal lupus syndrome (NLE), and lupus erythematosus disseminatus, juvenile onset (Type I) diabetes mellitus, including pediatric insulin-dependent diabetes mellitus (IDDM), and adult onset diabetes mellitus (Type II diabetes) and autoimmune diabetes. Also contemplated are immune responses associated with acute and delayed hypersensitivity mediated by cytokines and T-lymphocytes, sarcoidosis, granulomatosis including lymphomatoid granulomatosis, Wegener's granulomatosis, agranulocytosis, vasculitides, including vasculitis, large-vessel vasculitis (including polymyalgia rheumatica and gianT cell (Takayasu's) arteritis), medium-vessel vasculitis (including Kawasaki's disease and polyarteritis nodosa/periarteritis nodosa), microscopic polyarteritis, immunovasculitis, CNS vasculitis, cutaneous vasculitis, hypersensitivity vasculitis, necrotizing vasculitis such as systemic necrotizing vasculitis, and ANCA-associated vasculitis, such as Churg-Strauss vasculitis or syndrome (CSS) and ANCA-associated small-vessel vasculitis, temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), Addison's disease, autoimmune neutropenia, pancytopenia, leukopenia, diseases involving leukocyte diapedesis, CNS inflammatory disorders, Alzheimer's disease, Parkinson's disease, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Behcet's disease/syndrome, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, thermal injury, preeclampsia, an immune complex disorder such as immune complex nephritis, antibody-mediated nephritis, polyneuropathies, chronic neuropathy such as IgM polyneuropathies or IgM-mediated neuropathy, autoimmune or immune-mediated thrombocytopenia such as idiopathic thrombocytopenic purpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), experimental autoimmune encephalomyelitis, myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, gianT cell hepatitis, chronic active hepatitis or autoimmune chronic active hepatitis, lymphoid interstitial pneumonitis (LIP), bronchiolitis obliterans (non-transplant) vs NSIP, Guillain-Barre syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal or segmental or focal segmental glomerulosclerosis (FSGS), endocrine opthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia greata, alopecia totalis, CREST syndrome (calcinosis, Raynaud's phenomenon, esophageal dysmotility, sclerodactyl), and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis (acute or chronic), or Fuch's cyclitis, Henoch-Schonlein purpura, human immunodeficiency virus (HIV) infection, SCID, acquired immune deficiency syndrome (AIDS), echovirus infection, sepsis, endotoxemia, pancreatitis, thyroxicosis, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, gianT cell polymyalgia, chronic hypersensitivity pneumonitis, keratoconjunctivitis sicca, epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis *acuta*, pyoderma gangrenosum, Quervain's thyreoiditis, acquired spenic atrophy, non-malignant thymoma, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, autoimmune polyglandular syndrome type I, adult-onset idiopathic hypoparathyroidism (AOIH), cardiomyopathy such as dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism, neurological disease, lymphadenitis, reduction in blood pressure response, vascular dysfunction, tissue injury, cardiovascular ischemia, hyperalgesia, renal ischemia, cerebral ischemia, and disease accompanying vascularization, allergic hypersensitivity disorders, glomerulonephritides, reperfusion injury, ischemic re-perfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, graft versus host disease, contact hypersensitivity, asthmatic airway hyperreaction, or endometriosis.

V. Kits

Certain aspects of the present disclosure also concern kits containing compositions of the disclosure or compositions to implement methods of the disclosure. In some embodiments, kits can be used to evaluate one or more biomarkers. In certain embodiments, a kit contains, contains at least or contains at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1,000 or more probes, primers or primer sets, synthetic molecules or inhibitors, or any value or range and combination derivable therein. In some embodiments, there are kits for evaluating biomarker activity in a cell.

Kits may comprise components, which may be individually packaged or placed in a container, such as a tube, bottle, vial, syringe, or other suitable container means.

Individual components may also be provided in a kit in concentrated amounts; in some embodiments, a component is provided individually in the same concentration as it would be in a solution with other components. Concentrations of components may be provided as 1×, 2×, 5×, 10×, or 20× or more.

Kits for using probes, synthetic nucleic acids, non-synthetic nucleic acids, and/or inhibitors of the disclosure for prognostic or diagnostic applications are included as part of the disclosure. Specifically contemplated are any such molecules corresponding to any biomarker identified herein, which includes nucleic acid primers/primer sets and probes that are identical to or complementary to all or part of a biomarker, which may include noncoding sequences of the biomarker, as well as coding sequences of the biomarker.

In certain aspects, negative and/or positive control nucleic acids, probes, and inhibitors are included in some kit embodiments. In addition, a kit may include a sample that is a negative or positive control for one or more biomarkers.

It is contemplated that any method or composition described herein can be implemented with respect to any other method or composition described herein and that different embodiments may be combined. The claims originally filed are contemplated to cover claims that are multiply dependent on any filed claim or combination of filed claims.

Any embodiment of the disclosure involving specific biomarker by name is contemplated also to cover embodiments involving biomarkers whose sequences are at least 80, 81, 82, 83, 84, 85, 86, 87, 88, 89, 90, 91, 92, 93, 94, 95, 96, 97, 98, 99% identical to the mature sequence of the specified nucleic acid.

Embodiments of the disclosure include kits for analysis of a pathological sample by assessing biomarker profile for a sample comprising, in suitable container means, two or more biomarker probes, wherein the biomarker probes detect one or more of the biomarkers identified herein. The kit can further comprise reagents for labeling nucleic acids in the sample. The kit may also include labeling reagents, including at least one of amine-modified nucleotide, poly(A) polymerase, and poly(A) polymerase buffer. Labeling reagents can include an amine-reactive dye.

EXAMPLES

The following examples are included to demonstrate embodiments of the invention. It should be appreciated by those of skill in the art that the techniques disclosed in the examples which follow represent techniques discovered by the inventors to function well in the practice of the invention, and thus can be considered to constitute certain modes for its practice. However, those of skill in the art should, in light of the present disclosure, appreciate that many changes can be made in the specific embodiments which are disclosed and still obtain a like or similar result without departing from the spirit and scope of the invention.

Example 1—Identification of a Protective Fetal Microbial Profile in Healthy Twins

Methods

Study Design

A design of the analytical workflow is shown in FIG. 1, which illustrates enrollment of the twin pairs that were food allergic and those that were healthy. Statistical tests used Wilcoxon rank-sum tests for analysis of data.

Human Fecal Sample Collection

Participants were recruited as part of an observational study (ClinicalTrials.gov Identifier: NCT01613885) at multiple sites from 2014 to 2018. Food allergic participants in this study were diagnosed with food allergy by a staged and validated food challenge (13) performed by trained center staff. Fecal samples were collected per a standard operating procedure developed by the NIH Microbiome Project (21). Fecal samples were collected from 18 pairs of twins. Among 18 twin pairs, 13 were discordant for food allergy (one sibling had food allergy and the other was healthy) and 5 were concordant for food allergy (both siblings were food allergy). No one was on any medications or experienced any respiratory infections (e.g. cold, flu, pneumonia) at the time of fecal sample collection. All samples that passed QC (n=34 for microbiota analysis; n=36 for metabolite analysis) were used for statistical comparisons.

16S rRNA-Targeted Library Preparation and Sequencing

Bacterial DNA was extracted from fecal samples of the twin cohort using the Power Soil DNA Isolation Kit (MoBio). 16S rRNA-targeted gene amplicon library preparation and sequencing were performed at the Environmental Sample Preparation and Sequencing Facility at Argonne National Laboratory (DuPage, Illinois). The V4 region of the 16S rRNA gene was amplified by PCR with region-specific primers (515F-806R) that include sequencer adapter sequences used in the Illumina flowcell. 151 bp paired-end (PE) reads with 12 bp barcodes were generated following previously described protocols (22) on an Illumina MiSegm instrument. On average, each sample yielded 183,952±7,011 (mean±S.E.M.; ranging from 94,917 to 268,423) read pairs. One sample (S5077, allergic sibling of a twin pair) failed sequencing and yielded 0 reads and the corresponding twin pair (#13) was therefore excluded from 16S data analysis. A total of 34 samples (from 22 allergic and 12 healthy twins) was kept for further analysis, including 12 discordant twin pairs (n=24) and 5 concordant twin pairs (n=10).

16S rRNA Microbial Quantification and Normalization

The microbial 16S rRNA-targeted gene amplicon sequencing data were processed by Quantitative Insights into Microbial Ecology (QIIME) (version 1.9) (23) using a procedure similar to what has been previously described (24). In brief, low-quality bases were trimmed at 5' end of raw PE reads and 3' overlapping mates were merged by SeqPrep (Available on the World Wide Web at github.com/jstjohn/SeqPrep). The open reference OTU picking protocol was used at 97% sequence identity against the Greengenes database (August 2013 release) (25). Reads were aligned to reference sequences using PyNAST (26) and taxonomy was assigned using uclust consensus taxonomy assigner (27). Chimeric sequences were identified and removed using ChimeraSlayer (v20110519) (28). Sequences with "Unassigned" taxa at the kingdom level were also removed. Data were then rarefied to an even depth of 92,670 sequences across all samples (n=3734 the twin cohort). Alpha-diversity (Shannon index) was compared between the allergic and healthy groups using Wilcoxon rank-sum test (unpaired, non-parametric) for all samples or Wilcoxon signed-rank test (paired, non-parametric) within the discordant twin pairs only. Beta-diversity metrics were calculated and compared between the two groups using PERMANOVA with weighted UniFrac distance in R package vegan (v2.4.5) (29).

Differentially Abundant Microbial Taxa Identification

Bacterial taxa differentially abundant between allergic and healthy groups of the twin cohort were identified using the following approach. First, OTUs present in fewer than 4 samples were removed. Second, for all samples (n=34), relative abundance of OTUs was compared between the two groups using Discrete False-Discovery Rate (DS-FDR) (30) method (hereafter referred to as test #1) with parameters "transform type=normdata, method=meandiff, alpha=0.10, numperm=1000, fdr_method=dsfdr" (accessed 10102018) (available on the World Wide Web at github.com/biocore/dsFDR). The DS-FDR algorithm computes test statistics, raw P-values, and estimates false-discovery rate from a permutation test (default 1000 permutations). Of 5,590 OTUs total, 180 reached $P<0.05$; none reached FDR 0.10 potentially due to sample size. Then, within the discordant twin pairs (n=24, from 12 pairs), for which one sibling is allergic and the other is healthy, relative abundance of OTUs was compared between groups using Wilcoxon signed-rank test (paired, non-parametric) (hereafter referred to as test #2). Of 5,590 OTUs total, 259 reached a significance level of $P<0.10$. A more lenient P-value cutoff (0.10) was used here considering that non-parametric rank-based method has less power than DS-FDR method (30). After Benjamini-Hochberg FDR (BH-FDR) correction (31) for multiple testing, no OTUs passed FDR 0.10 potentially due to small sample sizes. Between 180 OTUs returned by test #1 and 259 OTUs returned by test #2, 64 OTUs overlapped and showed consistent direction of change in abundance (more abundant in healthy or allergic) in both tests and were kept for further analysis (OTUs shown in Table 2).

TABLE 2

List of 64 OTUs identified herein as differentially abundant between healthy and allergic twins.

| OTU | Taxonomy | Direction | OTU Type |
|---|---|---|---|
| 173135 | *k__Bacteria*; *p__Firmicutes*; *c__Clostridia*; *o__Clostridiales*; *f__Ruminococcaceae*; g__; s__ | UP in Healthy | Healthy-abundant |
| 174588 | *k__Bacteria*; *p__Firmicutes*; *c__Clostridia*; *o__Clostridiales*; *f__Lachnospiraceae*; g__; s__ | UP in Healthy | Healthy-abundant |
| 174818 | *k__Bacteria*; *p__Firmicutes*; *c__Clostridia*; *o__Clostridiales*; *f__Ruminococcaceae*; g__; s__ | UP in Healthy | Healthy-abundant |
| 176077 | *k__Bacteria*; *p__Firmicutes*; *c__Clostridia*; *o__Clostridiales*; f__; g__; s__ | UP in Healthy | Healthy-abundant |
| 176664 | *k__Bacteria*; *p__Firmicutes*; *c__Clostridia*; *o__Clostridiales*; *f__Lachnospiraceae*; *g__Roseburia*; *s__faecis* | UP in Healthy | Healthy-abundant |
| 178799 | *k__Bacteria*; *p__Firmicutes*; *c__Clostridia*; *o__Clostridiales*; *f__Ruminococcaceae*; g__; s__ | UP in Healthy | Healthy-abundant |
| 186478 | *k__Bacteria*; *p__Firmicutes*; *c__Clostridia*; *o__Clostridiales*; *f__Ruminococcaceae*; g__; s__ | UP in Healthy | Healthy-abundant |
| 188079 | *k__Bacteria*; *p__Firmicutes*; *c__Clostridia*; *o__Clostridiales*; *f__Ruminococcaceae*; *g__Ruminococcus* | UP in Healthy | Healthy-abundant |
| 189816 | *k__Bacteria*; *p__Firmicutes*; *c__Clostridia*; *o__Clostridiales* | UP in Allergic | Allergic-Abundant |
| 190169 | *k__Bacteria*; *p__Firmicutes*; *c__Clostridia*; *o__Clostridiales*; *f__Ruminococcaceae*; g__; s__ | UP in Healthy | Healthy-abundant |
| 190649 | *k__Bacteria*; *p__Firmicutes*; *c__Clostridia*; *o__Clostridiales*; *f__Ruminococcaceae*; g__; s__ | UP in Healthy | Healthy-abundant |
| 195258 | *k__Bacteria*; *p__Bacteroidetes*; *c__Bacteroidia*; *o__Bacteroidales*; | UP in Healthy | Healthy-abundant |

TABLE 2-continued

List of 64 OTUs identified herein as differentially abundant between healthy and allergic twins.

| OTU | Taxonomy | Direction | OTU Type |
|---|---|---|---|
| | *f__Bacteroidaceae*; *g__Bacteroides*; *s__ovatus* | | |
| 196139 | *k__Bacteria*; *p__Firmicutes*; *c__Clostridia*; *o__Clostridiales*; *f__Ruminococcaceae*; g__; s__ | UP in Healthy | Healthy-abundant |
| 198184 | *k__Bacteria*; *p__Firmicutes*; *c__Clostridia*; *o__Clostridiales*; *f__Ruminococcaceae*; g__; s__ | UP in Healthy | Healthy-abundant |
| 198941 | *k__Bacteria*; *p__Firmicutes*; *c__Clostridia*; *o__Clostridiales*; *f__Ruminococcaceae*; g__; s__ | UP in Healthy | Healthy-abundant |
| 2331530 | *k__Bacteria*; *p__Bacteroidetes*; *c__Bacteroidia*; *o__Bacteroidales*; *f__Bacteroidaceae*; *g__Bacteroides*; *s__uniformis* | UP in Healthy | Healthy-abundant |
| 269611 | *k__Bacteria*; *p__Firmicutes*; *c__Clostridia*; *o__Clostridiales*; *f__Ruminococcaceae*; g__; s__ | UP in Healthy | Healthy-abundant |
| 295804 | *k__Bacteria*; *p__Firmicutes*; *c__Clostridia*; *o__Clostridiales*; *f__Lachnospiraceae*; *g__Roseburia*; s__ | UP in Healthy | Healthy-abundant |
| 343313 | *k__Bacteria*; *p__Firmicutes*; *c__Clostridia*; *o__Clostridiales*; *f__Ruminococcaceae*; g__; s__ | UP in Healthy | Healthy-abundant |
| 361702 | *k__Bacteria*; *p__Firmicutes*; *c__Clostridia*; *o__Clostridiales*; *f__Ruminococcaceae*; *g__Ruminococcus*; s__ | UP in Healthy | Healthy-abundant |
| 362342 | *k__Bacteria*; *p__Firmicutes*; *c__Clostridia*; *o__Clostridiales*; *f__Ruminococcaceae*; *g__Ruminococcus*; s__ | UP in Healthy | Healthy-abundant |
| 362765 | *k__Bacteria*; *p__Firmicutes*; *c__Clostridia*; *o__Clostridiales*; *f__Ruminococcaceae*; *g__Ruminococcus*; s__ | UP in Healthy | Healthy-abundant |
| 370099 | *k__Bacteria*; *p__Firmicutes*; *c__Erysipelotrichi*; *o__Erysipelotrichales*; *f__Erysipelotrichaceae*; g__; s__ | UP in Healthy | Healthy-abundant |

TABLE 2-continued

List of 64 OTUs identified herein as differentially abundant between healthy and allergic twins.

| OTU | Taxonomy | Direction | OTU Type |
|---|---|---|---|
| 4402610 | *k__Bacteria*; *p__Bacteroidetes*; *c__Bacteroidia*; *o__Bacteroidales*; *f__[Odoribacteraceae]*; *g__Butyricimonas*; s__ | UP in Healthy | Healthy-abundant |
| 509709 | *k__Bacteria*; *p__Firmicutes*; *c__Clostridia*; *o__Clostridiales*; *f__Lachnospiraceae*; *g__Dorea*; s__ | UP in Healthy | Healthy-abundant |
| 556835 | *k__Bacteria*; *p__Firmicutes*; *c__Clostridia*; *o__Clostridiales*; *f__Veillonellaceae*; *g__Phascolarcto-bacterium*; s__ | UP in Healthy | Healthy-abundant |
| 574038 | *k__Bacteria*; *p__Firmicutes*; *c__Clostridia*; *o__Clostridiales*; *f__Lachnospiraceae*; g__; s__ | UP in Healthy | Healthy-abundant |
| 658370 | *k__Bacteria*; *p__Firmicutes*; *c__Clostridia*; *o__Clostridiales*; *f__Lachnospiraceae*; g__; s__ | UP in Healthy | Healthy-abundant |
| 823634 | *k__Bacteria*; *p__Firmicutes*; *c__Clostridia*; *o__Clostridiales*; *f__Ruminococcaceae*; *g__Ruminococcus*; *s__bromii* | UP in Healthy | Healthy-abundant |
| New.CleanUp. Reference OTU110487 | *k__Bacteria*; *p__Firmicutes*; *c__Clostridia*; *o__Clostridiales*; *f__Ruminococcaceae*; *g__Ruminococcus*; s__ | UP in Healthy | Healthy-abundant |
| New.CleanUp. Reference OTU112566 | *k__Bacteria*; *p__Bacteroidetes*; *c__Bacteroidia*; *o__Bacteroidales*; *f__Bacteroidaceae*; *g__Bacteroides*; *s__uniformis* | UP in Healthy | Healthy-abundant |
| New.CleanUp. Reference OTU122371 | *k__Bacteria*; *p__Firmicutes*; *c__Clostridia*; *o__Clostridiales*; *f__Lachnospiraceae*; g__; s__ | UP in Healthy | Healthy-abundant |
| New.CleanUp. Reference OTU124061 | *k__Bacteria*; *p__Firmicutes*; *c__Clostridia*; *o__Clostridiales*; *f__Lachnospiraceae*; g__; s__ | UP in Healthy | Healthy-abundant |
| New.CleanUp. Reference OTU127991 | *k__Bacteria*; *p__Firmicutes*; *c__Clostridia*; *o__Clostridiales*; *f__Ruminococcaceae*; *g__Ruminococcus*; s__ | UP in Healthy | Healthy-abundant |
| New.CleanUp. Reference OTU1320 | *k__Bacteria*; *p__Firmicutes*; *c__Clostridia*; *o__Clostridiales*; *f__Ruminococcaceae*; *g__Faecalibacterium*; *s__prausnitzii* | UP in Healthy | Healthy-abundant |
| New.CleanUp. Reference OTU134087 | *k__Bacteria*; *p__Firmicutes*; *c__Clostridia*; *o__Clostridiales*; *f__Lachnospiraceae*; g__; s__ | UP in Healthy | Healthy-abundant |
| New.CleanUp. Reference OTU135990 | *k__Bacteria*; *p__Firmicutes*; *c__Clostridia*; *o__Clostridiales*; *f__Lachnospiraceae*; *g__Coprococcus*; s__ | UP in Healthy | Healthy-abundant |
| New.CleanUp. Reference OTU141755 | *k__Bacteria*; *p__Firmicutes*; *c__Clostridia*; *o__Clostridiales*; *f__Lachnospiraceae* | UP in Healthy | Healthy-abundant |
| New.CleanUp. Reference OTU141972 | *k__Bacteria*; *p__Firmicutes*; *c__Clostridia*; *o__Clostridiales*; *f__Ruminococcaceae*; *g__Ruminococcus*; s__ | UP in Healthy | Healthy-abundant |
| New.CleanUp. Reference OTU149108 | *k__Bacteria*; *p__Firmicutes*; *c__Clostridia*; *o__Clostridiales*; *f__Lachnospiraceae*; *g__Lachnospira*; s__ | UP in Healthy | Healthy-abundant |
| New.CleanUp. Reference OTU152821 | *k__Bacteria*; *p__Firmicutes*; *c__Clostridia*; *o__Clostridiales*; f__; g__; s__ | UP in Healthy | Healthy-abundant |
| New.CleanUp. Reference OTU153408 | *k__Bacteria*; *p__Bacteroidetes*; *c__Bacteroidia*; *o__Bacteroidales*; *f__Bacteroidaceae*; *g__Bacteroides*; *s__uniformis* | UP in Healthy | Healthy-abundant |
| New.CleanUp. Reference OTU153961 | *k__Bacteria*; *p__Firmicutes*; *c__Clostridia*; *o__Clostridiales*; *f__Ruminococcaceae* | UP in Healthy | Healthy-abundant |
| New.CleanUp. Reference OTU156924 | *k__Bacteria*; *p__Bacteroidetes*; *c__Bacteroidia*; *o__Bacteroidales*; *f__Bacteroidaceae*; *g__Bacteroides*; s__ | UP in Healthy | Healthy-abundant |
| New.CleanUp. Reference OTU164203 | *k__Bacteria*; *p__Firmicutes*; *c__Clostridia*; *o__Clostridiales*; *f__Ruminococcaceae*; *g__Oscillospira*; s__ | UP in Healthy | Healthy-abundant |
| New.CleanUp. Reference OTU28435 | *k__Bacteria*; *p__Firmicutes*; *c__Clostridia*; *o__Clostridiales*; *f__Lachnospiraceae*; *g__Coprococcus*; s__ | UP in Healthy | Healthy-abundant |
| New.CleanUp. Reference OTU37938 | *k__Bacteria*; *p__Firmicutes*; *c__Clostridia*; *o__Clostridiales*; *f__Lachnospiraceae*; *g__Blautia*; s__ | UP in Healthy | Healthy-abundant |

TABLE 2-continued

List of 64 OTUs identified herein as differentially abundant between healthy and allergic twins.

| OTU | Taxonomy | Direction | OTU Type |
| --- | --- | --- | --- |
| New.CleanUp. Reference OTU41338 | *k__Bacteria*; *p__Firmicutes*; *c__Clostridia*; *o__Clostridiales*; *f__Ruminococcaceae*; *g__Ruminococcus*; *s__bromii* | UP in Healthy | Healthy-abundant |
| New.CleanUp. Reference OTU41725 | *k__Bacteria*; *p__Firmicutes*; *c__Clostridia*; *o__Clostridiales*; f__; g__; s__ | UP in Healthy | Healthy-abundant |
| New.CleanUp. Reference OTU47134 | *k__Bacteria*; *p__Firmicutes*; *c__Clostridia*; *o__Clostridiales*; *f__Ruminococcaceae* | UP in Healthy | Healthy-abundant |
| New.CleanUp. Reference OTU5050 | *k__Bacteria*; *p__Firmicutes*; *c__Clostridia*; *o__Clostridiales*; *f__Lachnospiraceae*; *g__Lachnospira*; s__ | UP in Healthy | Healthy-abundant |
| New.CleanUp. Reference OTU57003 | *k__Bacteria*; *p__Firmicutes*; *c__Clostridia*; *o__Clostridiales*; *f__Lachnospiraceae*; *g__Coprococcus*; s__ | UP in Healthy | Healthy-abundant |
| New.CleanUp. Reference OTU58395 | *k__Bacteria*; *p__Firmicutes*; *c__Clostridia*; *o__Clostridiales*; *f__Lachnospiraceae*; *g__Coprococcus*; s__ | UP in Healthy | Healthy-abundant |
| New.CleanUp. Reference OTU58632 | *k__Bacteria*; *p__Firmicutes*; *c__Clostridia*; *o__Clostridiales*; *f__Ruminococcaceae*; *g__Ruminococcus*; s__ | UP in Healthy | Healthy-abundant |
| New.CleanUp. Reference OTU74051 | *k__Bacteria*; *p__Firmicutes*; *c__Clostridia*; *o__Clostridiales*; *f__Ruminococcaceae*; *g__Faecalibacterium*; *s__prausnitzii* | UP in Healthy | Healthy-abundant |
| New.CleanUp. Reference OTU79183 | *k__Bacteria*; *p__Firmicutes*; *c__Clostridia*; *o__Clostridiales*; *f__Lachnospiraceae*; g__; s__ | UP in Healthy | Healthy-abundant |
| New.CleanUp. Reference OTU80284 | *k__Bacteria*; *p__Firmicutes*; *c__Clostridia*; *o__Clostridiales*; *f__Lachnospiraceae*; g__; s__ | UP in Healthy | Healthy-abundant |
| New.CleanUp. Reference OTU86790 | *k__Bacteria*; *p__Firmicutes*; *c__Clostridia*; *o__Clostridiales*; *f__Lachnospiraceae*; g__; s__ | UP in Allergic | Allergic-Abundant |
| New.CleanUp. Reference OTU86928 | *k__Bacteria*; *p__Firmicutes*; *c__Clostridia*; *o__Clostridiales*; *f__Ruminococcaceae*; *g__Faecalibacterium*; *s__prausnitzii* | UP in Healthy | Healthy-abundant |
| New.CleanUp. Reference OTU89172 | *k__Bacteria*; *p__Firmicutes*; *c__Clostridia*; *o__Clostridiales*; *f__Lachnospiraceae*; *g__Coprococcus*; s__ | UP in Healthy | Healthy-abundant |
| New.CleanUp. Reference OTU92834 | *k__Bacteria*; *p__Firmicutes*; *c__Clostridia*; *o__Clostridiales*; *f__Ruminococcaceae*; *g__Oscillospira*; s__ | UP in Healthy | Healthy-abundant |
| New.CleanUp. Reference OTU97550 | *k__Bacteria*; *p__Firmicutes*; *c__Clostridia*; *o__Clostridiales*; *f__Lachnospiraceae*; g__; s__ | UP in Healthy | Healthy-abundant |
| New.CleanUp. Reference OTU99007 | *k__Bacteria*; *p__Bacteroidetes*; *c__Bacteroidia*; *o__Bacteroidales*; *f__ Porphyromonadaceae*; *g__Parabacteroides*; s__ | UP in Healthy | Healthy-abundant |
| New.Reference OTU129 | *k__Bacteria*; *p__Bacteroidetes*; *c__Bacteroidia*; *o__Bacteroidales*; *f__Bacteroidaceae*; *g__Bacteroides*; s__ | UP in Healthy | Healthy-abundant |

OTU Abundance Score Calculation

Figure 5:
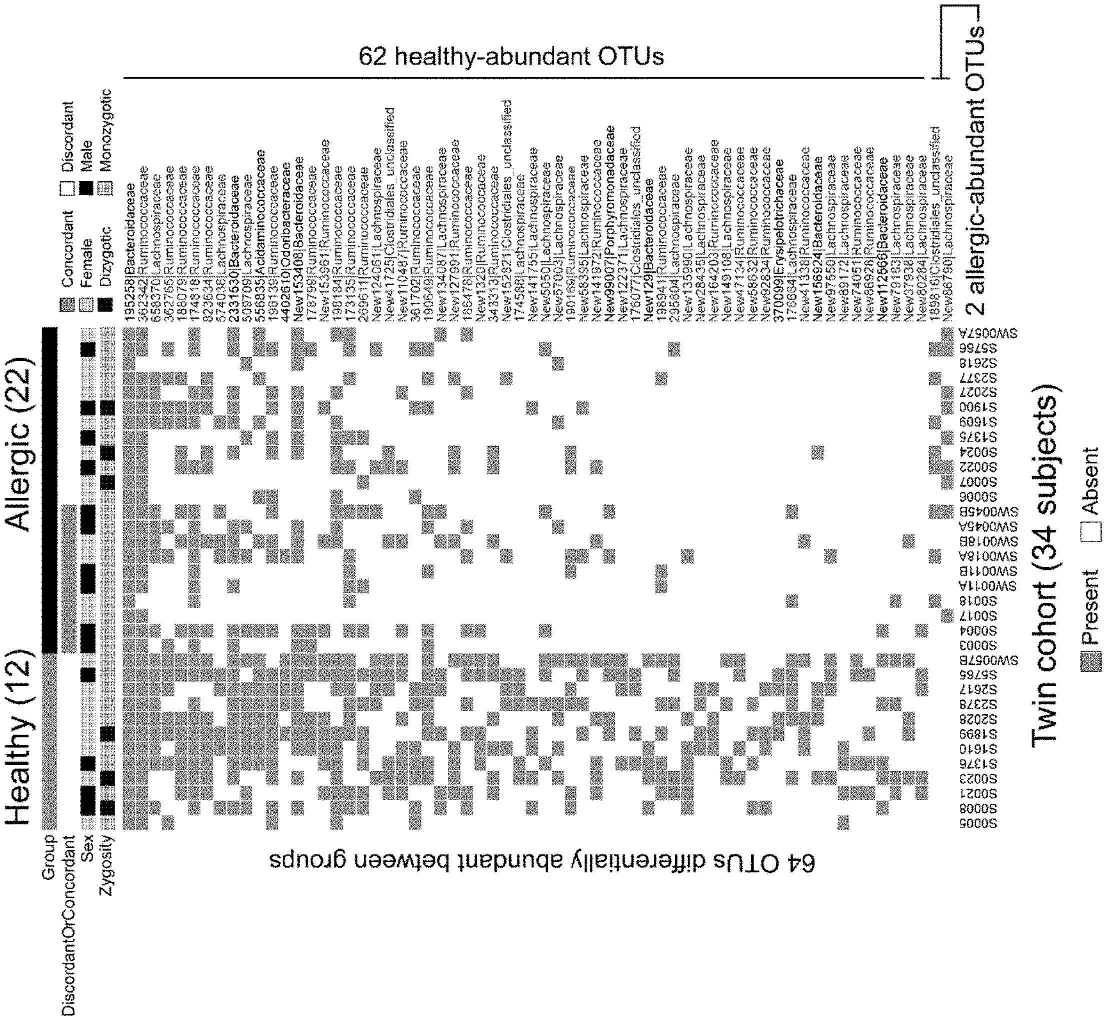
FIG. 5 shows a binary heatmap of the 64 OTUs differentially abundant between healthy and allergic groups. Dark gray indicates the presence of an OTU in a sample, and light grey indicates absence. The 64 OTUs are those listed in Table 2. Out of 64 OTUs, 62 were more abundant in the healthy group (healthy-abundant OTUs), and 2 are more abundant in the allergic group (allergic-abundant OTUs). OTU IDs are shown on the row in the format of "OTU_ID|Family", and those annotated with family Lachnospiraceae, Ruminococcaceae, or Clostridiales_unclassified are highlighted. Sample IDs are shown on the column, with annotation bars above the heatmap indicating concordant/discordant twin members, sex, and zygosity.
Figure 6:
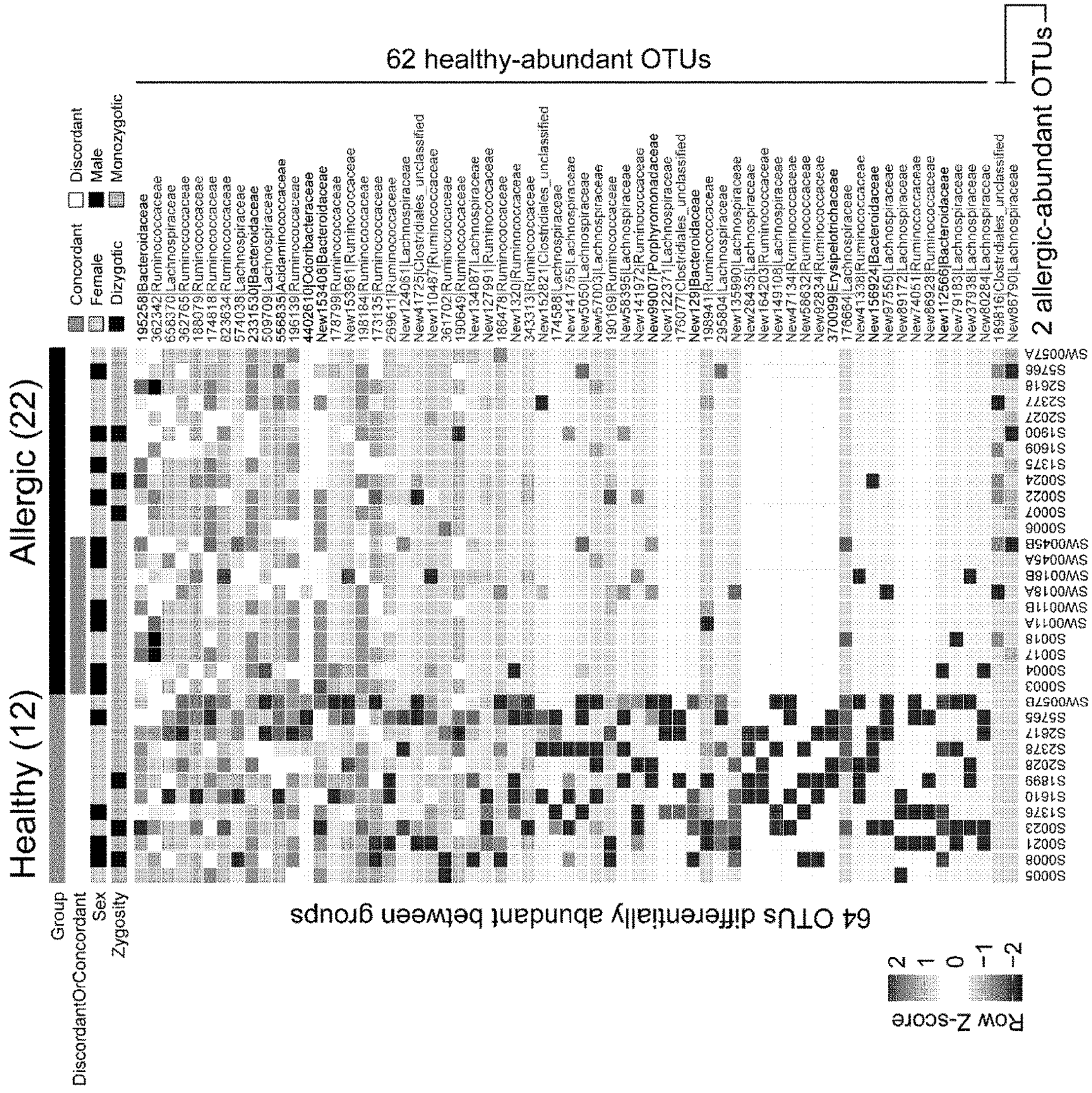
FIG. 6 shows a relative abundance heatmap of the 64 OTUs identified herein as differentially abundant. Of these 64 OTUs, 62 were more abundant in the healthy group (healthy-abundant OTUs), and 2 were more abundant in the allergic group (allergic-abundant OTU). OTU IDs are shown on the row in the format of "OTU_ID|Family," and those annotated with the Clostridia class (Lachnospiraceae, Ruminococcaceae, unclassified Clostridiales) are highlighted. Sample IDs are shown on the column, with annotation bars above the heatmap indicating concordant/discordant twin members, sex, and zygosity. Out of 36 samples total in the twin cohort, one sample (S5077) failed sequencing and yielded 0 reads, hence the corresponding twin pair (#13) was excluded from 16S analysis. DS-FDR was used on all samples (P<0.05) and two-sided Wilcoxon signed-rank test was used on discordant twin pairs (P<0.10), respectively. Unadjusted P-value thresholds were used to filter for OTUs of interest.
Figure 7A:
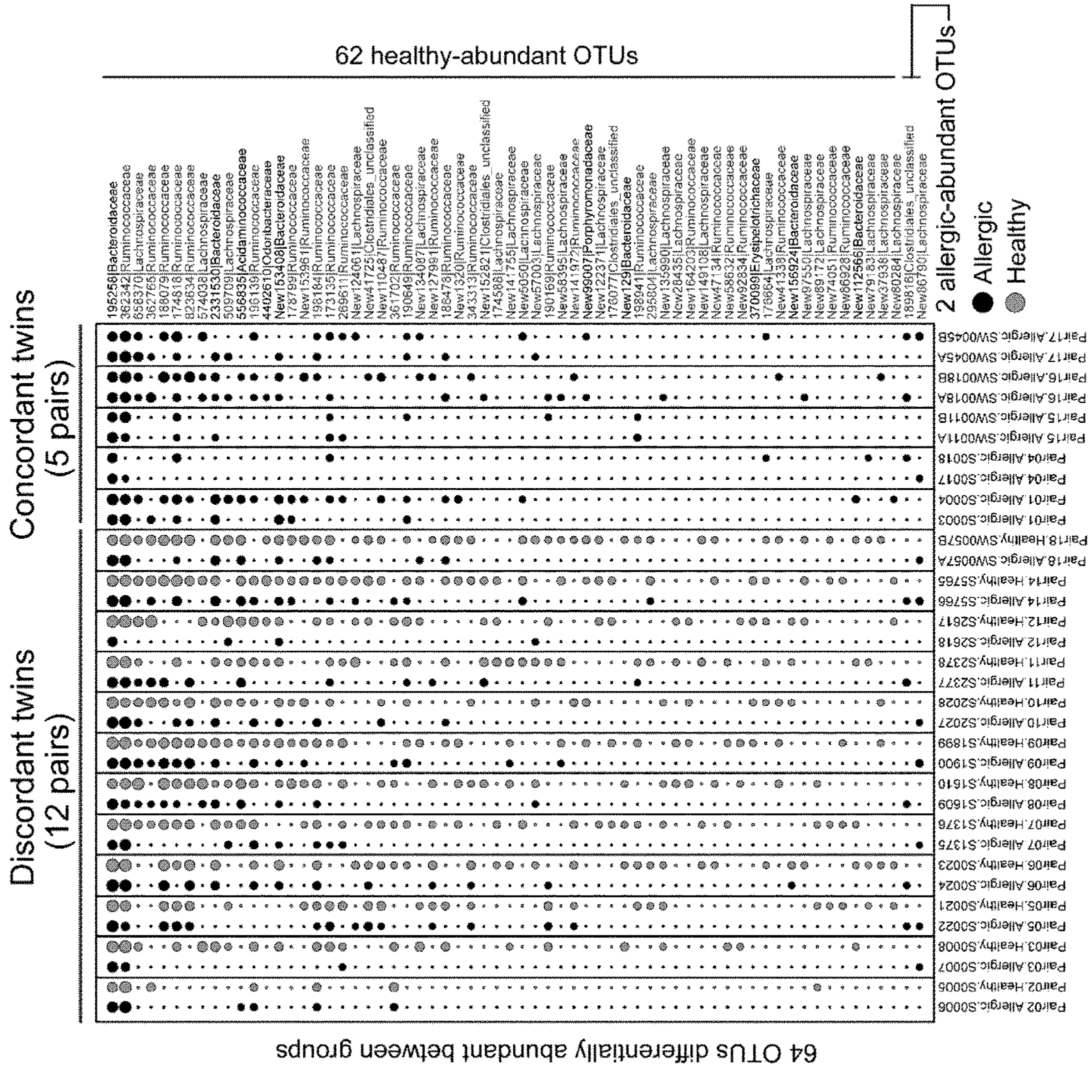
FIG. 7A shows a bubble plot showing the per-twin-pair abundance differences of the 64 differentially abundant OTUs. The size of each circle corresponds to the relative abundance of an OTU. Samples were arranged as: discordant twins (12 pairs, n=24), where one member is healthy and the other member is allergic; concordant twins (5 pairs, n=10), where both members are allergic. OTU IDs are shown on the row in the format of "OTU_ID|Family," and those annotated with the Clostridia class (Lachnospiraceae, Ruminococcaceae, unclassified Clostridiales) are highlighted.

Out of 64 OTUs differentially abundant between allergic and healthy twin members, 62 were more abundant in the healthy group (hereby referred to as healthy-abundant OTUs), and 2 were more abundant in the allergic group (hereby referred to as allergic-abundant OTUs) (see Table 2 and FIGS. 5, 6, and 7A). The limited number of allergic-abundant OTUs did not warrant the calculation of an OTU ratio as previously made (23), defined as the total number of potentially healthy-abundant OTUs divided by the total number of potentially allergic-abundant OTUs per sample. Here, an "OTU abundance score" was calculated as an aggregated signature taking into consideration the relative abundance of the 64 OTUs shown in Table 2 and FIG. 6. First, the rarefied absolute count matrix of OTUs was added by offset 1.0 and log 10-transformed to bring data to close to Gaussian distribution, then scaled by dividing the value by their root mean square across samples. The abundance of allergic-abundant OTUs was multiplied by (−1). Second, the sum of the transformed abundance of the 64 OTUs was calculated to generate the aggregate score.

Results

Figure 2:
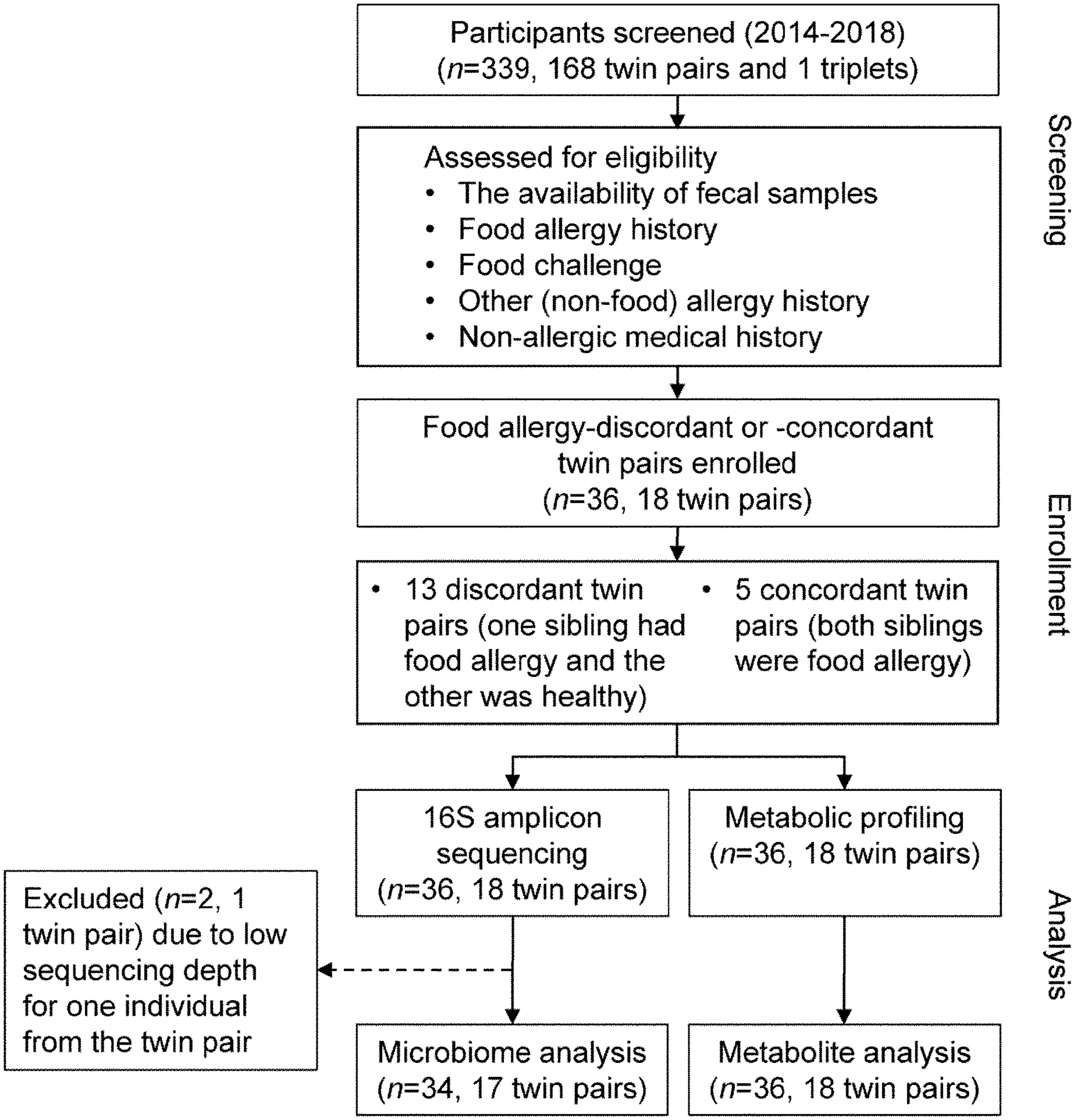
FIG. 2 shows a flow diagram of study design and participating patients.

Microbial signatures and metabolomic profiles were examined in the fecal samples from a unique collection of twin pairs that were raised in the same household in which they equally avoided the foods that the affected twin was found to be allergic to and were either concordant or discordant for food allergy (FIG. 2). Baseline demographic and clinical characteristics of the twin cohort are shown in Tables 3-1 and 3-2. The average age of participants at sample collection was 39.4±4.1 years (mean±SEM). All of the twins lived independently after the age of 19 years. There were no significant differences in the baseline demographical and clinical characteristics between the healthy vs. food-allergic twin pairs.

TABLE 3-1

| Baseline demographic and clinical characteristics of the twin cohort | | | | | | | | |
|---|---|---|---|---|---|---|---|---|
| | | Demographics | | | | | | |
| Twin pairs | Sample ID# | Discordant or concordant | Zygosity | Age at stool collection | Sex | Race | Body Mass Index | Breast-feeding for at least 6 mo |
| 1 | S0003 | concordant | Monozygotic | 57 | Male | White | 25.77 | no |
| | S0004 | concordant | Monozygotic | 57 | Male | White | 26.70 | no |
| 2 | S0005 | discordant | Monozygotic | 0.5 | Female | Asian and White | 18.23 | Yes |
| | S0006 | discordant | Monozygotic | 0.5 | Female | Asian and White | 18.95 | Yes |
| 3 | S0008 | discordant | Dizygotic | 6 | Male | Asian | 12.63 | Yes |
| | S0007 | discordant | Dizygotic | 6 | Female | Asian | NA | Yes |
| 4 | S0017 | concordant | Monozygotic | 1 | Female | White | 17.55 | Yes |
| | S0018 | concordant | Monozygotic | 1 | Female | White | 16.82 | Yes |
| 5 | S0021 | discordant | Monozygotic | 5 | Male | Asian | 15.09 | No |
| | S0022 | discordant | Monozygotic | 5 | Male | Asian | 15.08 | No |
| 6 | S0023 | discordant | Dizygotic | 5 | Female | White | 13.10 | Yes |
| | S0024 | discordant | Dizygotic | 5 | Female | White | 13.75 | Yes |
| 7 | S1376 | discordant | Monozygotic | 58 | Male | Hispanic or Latino | 27.62 | Yes |
| | S1375 | discordant | Monozygotic | 58 | Male | Hispanic or Latino | 26.87 | Yes |
| 8 | S1610 | discordant | Monozygotic | 48 | Female | Asian | 27.79 | No |
| | S1609 | discordant | Monozygotic | 48 | Female | Asian | 26.63 | No |
| 9 | S1899 | discordant | Dizygotic | 57 | Female | White | 29.35 | Yes |
| | S1900 | discordant | Dizygotic | 57 | Male | White | 31.37 | Yes |
| 10 | S2028 | discordant | Monozygotic | 53 | Female | White | 22.25 | No |
| | S2027 | discordant | Monozygotic | 53 | Female | White | 21.57 | No |
| 11 | S2378 | discordant | Monozygotic | 46 | Female | White | 30.89 | Yes |
| | S2377 | discordant | Monozygotic | 46 | Female | White | 28.49 | Yes |
| 12 | S2617 | discordant | Monozygotic | 70 | Female | White | 25.97 | Yes |
| | S2618 | discordant | Monozygotic | 70 | Female | White | 28.59 | Yes |
| 13 | S5078 | discordant | Dizygotic | 47 | Female | Asian | 31.93 | Yes |
| | S5077 | discordant | Dizygotic | 47 | Female | Asian | 25.97 | Yes |
| 14 | S5765 | discordant | Monozygotic | 57 | Male | White | 35.70 | Yes |
| | S5766 | discordant | Monozygotic | 57 | Male | White | 34.44 | Yes |
| 15 | SW0011A | concordant | Monozygotic | 58 | Male | White | 34.35 | No |
| | SW0011B | concordant | Monozygotic | 58 | Male | White | 36.12 | No |
| 16 | SW0018A | concordant | Monozygotic | 56 | Female | Black or African American | 35.76 | No |
| | SW0018B | concordant | Monozygotic | 56 | Female | Black or African American | 35.18 | No |
| 17 | SW0045A | concordant | Monozygotic | 63 | Male | White | 37.95 | No |
| | SW0045B | concordant | Monozygotic | 63 | Male | White | 41.09 | No |
| 18 | SW0057B | discordant | Monozygotic | 22 | Female | White | 18.13 | Yes |
| | SW0057A | discordant | Monozygotic | 22 | Female | White | 19.64 | Yes |

TABLE 3-2

| Baseline demographic and clinical characteristics of the twin cohort | | | | | | | |
|---|---|---|---|---|---|---|---|
| | | Food Allergy History | | | | Has a doctor ever told | Has a doctor |
| Twin pairs | Sample ID# | Food allergies | Food Allergens | Years with the peanut allergy | Years with other food allergy | you that you have atopic dermatitis or eczema? | ever told you that you have asthma? |
| 1 | S0003 | Allergic | Peanut, Tree nuts, Shellfish, Soy | 56 | 56 | No | Yes |
| | S0004 | Allergic | Egg | 0 | 55 | No | No |
| 2 | S0005 | Healthy | None | 0 | 0 | Yes | No |
| | S0006 | Allergic | Egg | 0 | 0.3 | Yes | No |
| 3 | S0008 | Healthy | None | 0 | 0 | No | No |
| | S0007 | Allergic | Peanut, Tree nuts | 5.3 | 5 | No | No |
| 4 | S0017 | Allergic | Egg | 0 | 0.4 | No | No |
| | S0018 | Allergic | Egg | 0 | 0.4 | No | No |

TABLE 3-2-continued

Baseline demographic and clinical characteristics of the twin cohort

| Twin pairs | Sample ID# | Food Allergy History: Food allergies | Food Allergens | Years with the peanut allergy | Years with other food allergy | Has a doctor ever told you that you have atopic dermatitis or eczema? | Has a doctor ever told you that you have asthma? |
|---|---|---|---|---|---|---|---|
| 5 | S0021 | Healthy | None | 0 | 0 | No | No |
| | S0022 | Allergic | Peanut, Tree nuts, Fish, Mustard | 4 | 4 | No | Yes |
| 6 | S0023 | Healthy | None | 0 | 0 | No | No |
| | S0024 | Allergic | Peanut, Egg | 2 | 2 | No | Yes |
| 7 | S1376 | Healthy | None | 0 | 0 | No | Yes |
| | S1375 | Allergic | Oats, olives, corn | 0 | 23 | No | No |
| 8 | S1610 | Healthy | None | 0 | 0 | Yes | Yes |
| | S1609 | Allergic | Rice, Pineapple | 0 | 25 | No | Yes |
| 9 | S1899 | Healthy | None | 0 | 0 | No | Yes |
| | S1900 | Allergic | Peanut, Milk | 55 | 56 | No | Yes |
| 10 | S2028 | Healthy | None | 0 | 0 | No | Yes |
| | S2027 | Allergic | Peanut, Garbanzo beans | 50 | 45 | Yes | Yes |
| 11 | S2378 | Healthy | None | 0 | 0 | Yes | No |
| | S2377 | Allergic | Milk, Wheat | 0 | 45 | Yes | Yes |
| 12 | S2617 | Healthy | None | 0 | 0 | No | No |
| | S2618 | Allergic | Milk | 0 | 68 | No | Yes |
| 13 | S5078 | Healthy | None | 0 | 0 | No | No |
| | S5077 | Allergic | Milk | 0 | 46 | No | No |
| 14 | S5765 | Healthy | None | 0 | 0 | No | No |
| | S5766 | Allergic | Tree nuts | 0 | 50 | No | Yes |
| 15 | SW0011A | Allergic | Shellfish | 0 | 52 | No | Yes |
| | SW0011B | Allergic | Milk | 0 | 50 | Yes | Yes |
| 16 | SW0018A | Allergic | Tree nuts, Bananas, Kiwi, Avocado, Mangos, Melons, Carrots, Cucumber | 0 | 50 | No | Yes |
| | SW0018B | Allergic | Shellfish | 0 | 45 | No | Yes |
| 17 | SW0045A | Allergic | Apples | 0 | 55 | No | Yes |
| | SW0045B | Allergic | Tree nuts, Shellfish, melons, squash | 0 | 56 | No | No |
| 18 | SW0057B | Healthy | None | 0 | 0 | No | Yes |
| | SW0057A | Allergic | Shellfish, Banana, crab | 0 | 18 | No | Yes |

Figure 3A:
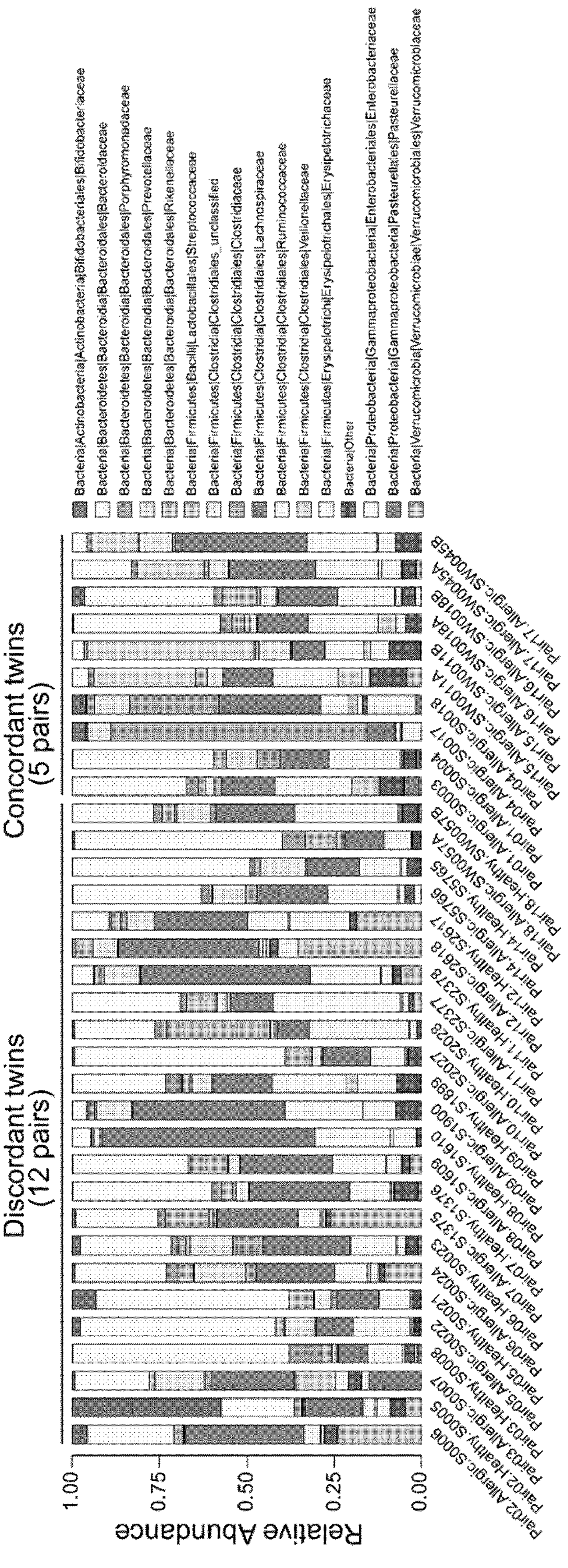
FIGS. 3A-3E show an overview of microbial composition from healthy and allergic twins.
Figure 3C:
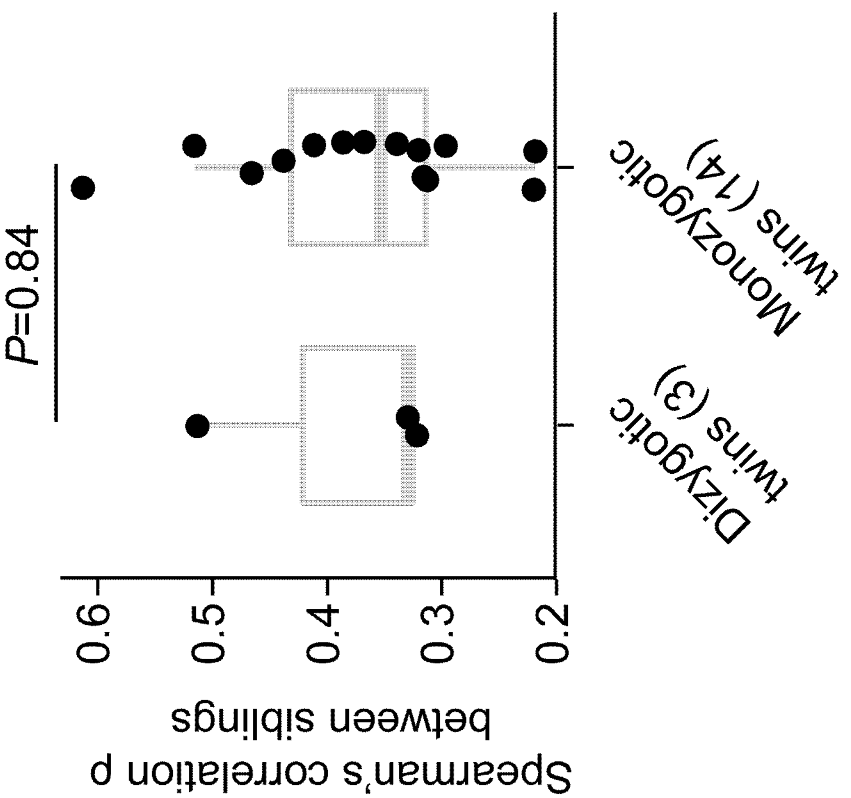
Figure 3B:
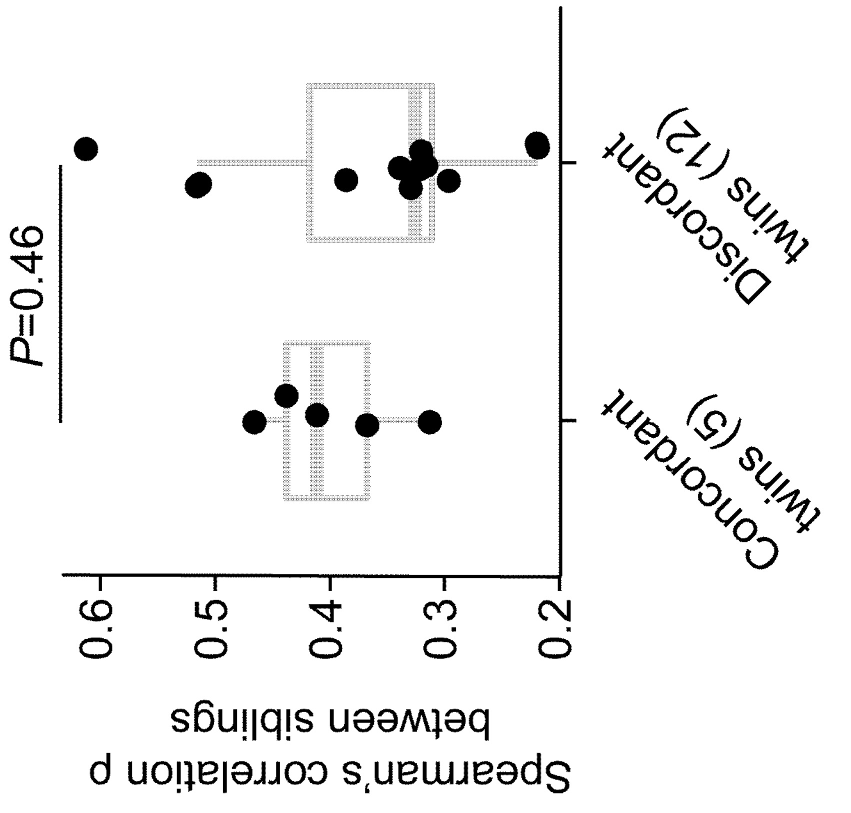
Figure 3D:
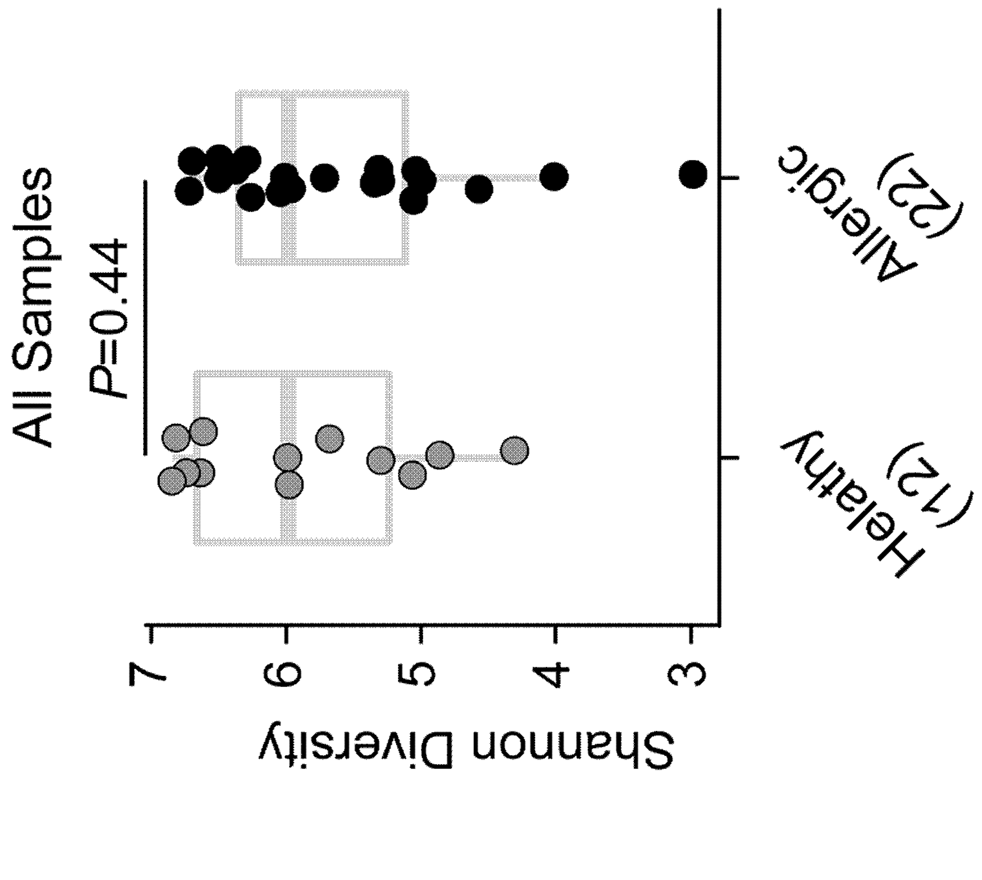
Figure 3E:
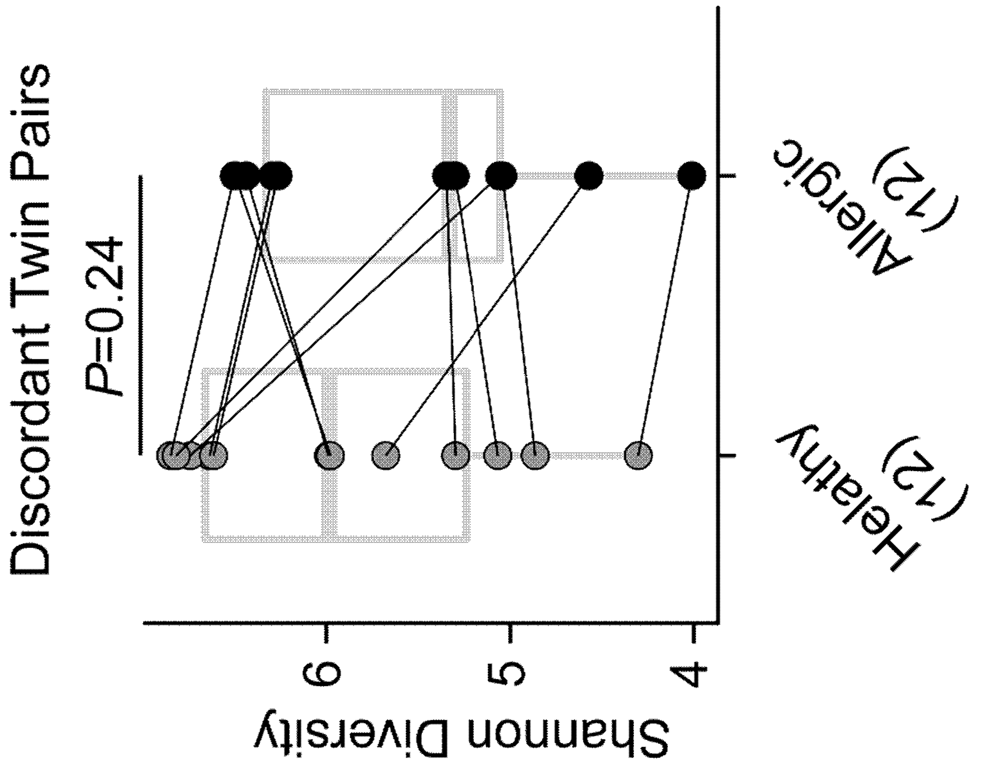
Figure 4:
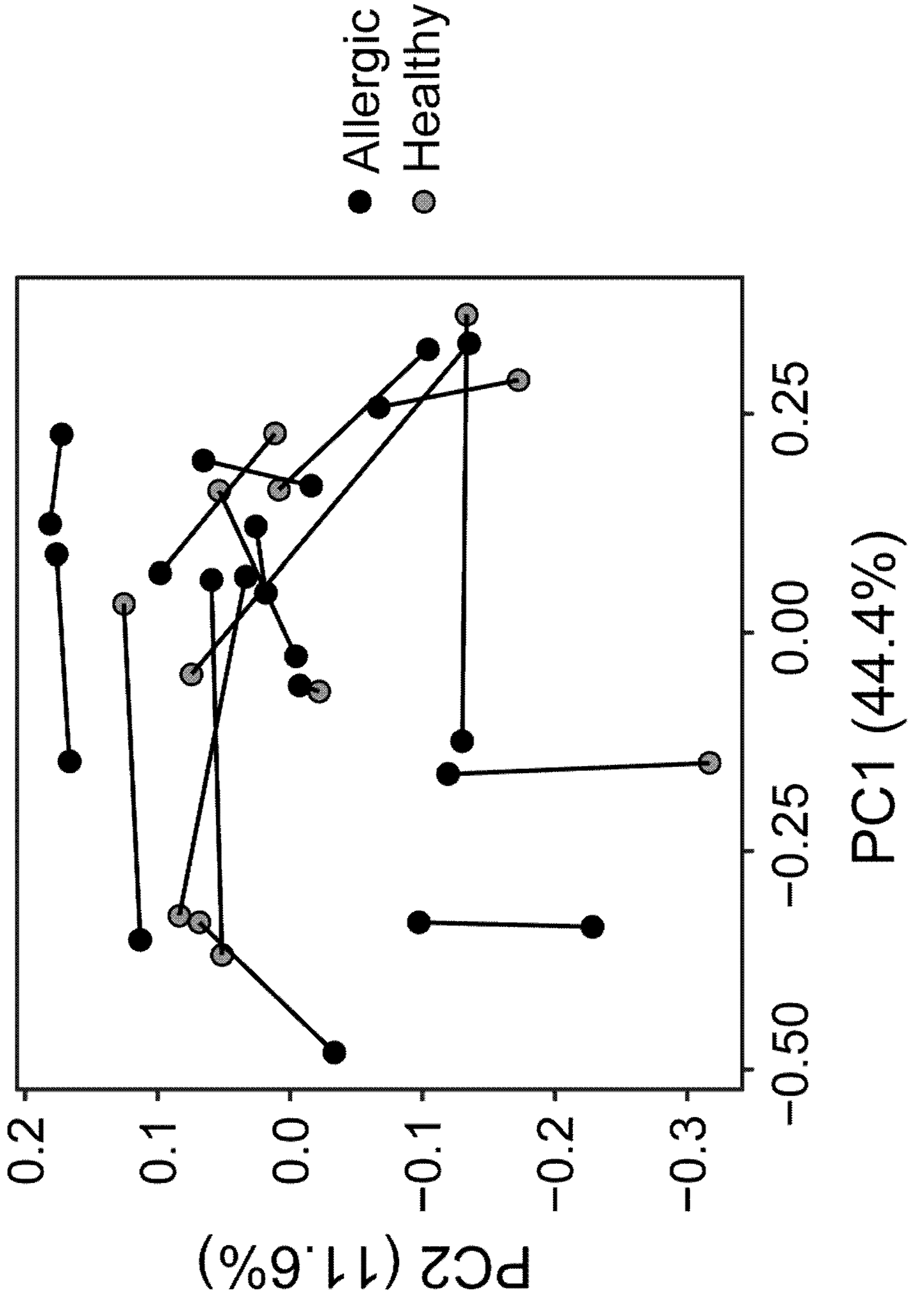
FIG. 4 shows a β-diversity Principal Coordinates Analysis (PCoA) of twin fecal microbial communities with weighted UniFrac measure. Shown is a plot of the first two principal coordinate axes (PC1 and PC2) explaining 44.4% and 11.6% of the total variance among 34 samples from the healthy and allergic twins. Each dot represents one sample. Line connects samples from the same twin pair. PERMANOVA was used to test the diversity differences between healthy and allergic groups (P=0.82).

16S rRNA-gene amplicon sequencing was performed on fecal samples from the 13 healthy and 23 food-allergic age-matched twin pairs. After excluding 1 sample with low sequencing depth and the corresponding twin pair, 34 samples were included for analysis, including 24 samples from 12 discordant twin pairs (1 allergic, 1 healthy) and 10 samples from 5 from concordant twin pairs (both allergic). An overview of the analytical workflow is shown in FIG. 1. The composition of commensal microbiota is shown in FIG. 3A. While there was sample-to-sample variation, the presence of major families such as Bacteroidaceae, Lachnospiraceae, and Ruminococcaceae was consistent with those reported in previous studies on fecal samples (32). For each twin pair, the relative abundance of Operational Taxonomic Units (OTUs) was compared. OTUs represent groups of microbes between closely related individuals. No significant differences were found in within-pair, sibling-wise OTU correlation between discordant and concordant twin pairs, or between dizygotic and monozygotic twin pairs (FIGS. 3B and 3C). Across all samples or within discordant twin pairs only, no significant differences were detected in the a-diversity (Shannon Diversity; FIGS. 3D and 3E). P-diversity (weighted UniFrac distance) metrics also did not differ between allergic and healthy groups (FIG. 4).

Figure 7B:
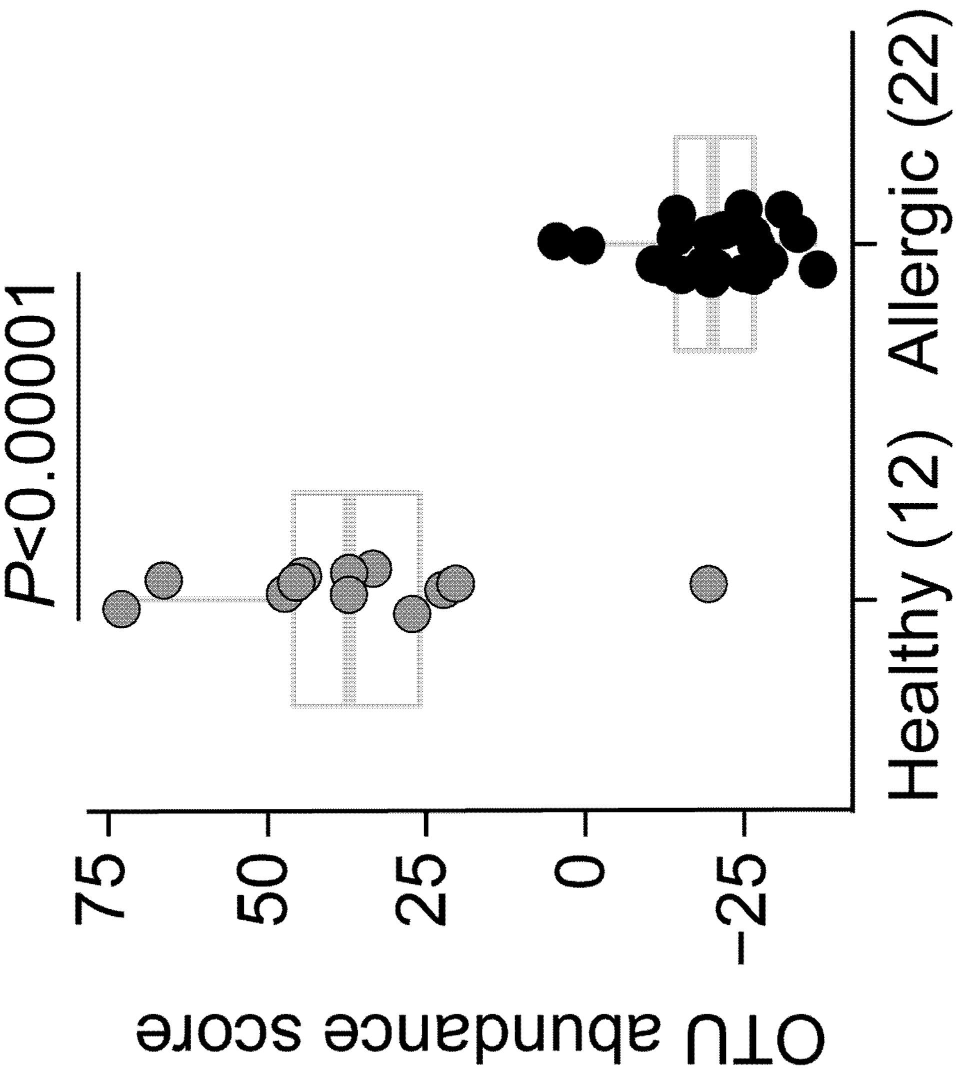
FIG. 7B shows the OTU abundance scores for each individual. The aggregated OTU abundance score was significantly higher in healthy (n=12) relative to allergic twins (n=22). The score was calculated using the 64 differentially abundant OTUs shown in FIG. 5, FIG. 6, FIG. 7A and Table 2. Each dot denotes one sample. The bounds of the boxes represent the 25th and 75th percentiles, the horizontal center line indicates the median, and the whiskers extend to data points within a maximum of 1.5 times the IQR.
Figure 8:
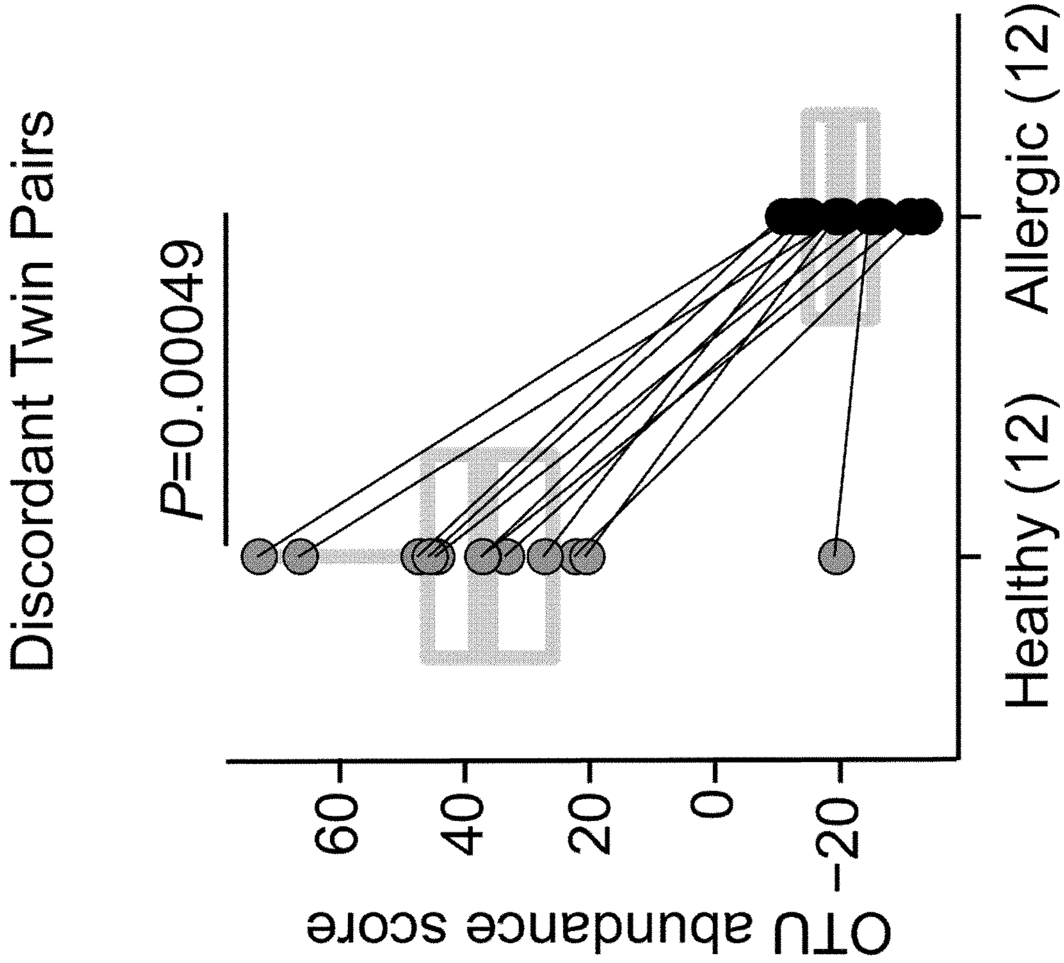
FIG. 8 shows data demonstrating that the aggregated OTU abundance score is significantly higher in healthy relative to allergic group in the discordant twin pairs (12 pairs, n=24). Each dot denotes one sample. The bounds of the boxes represent the 25th and 75th percentiles, the horizontal center line indicates the median, and the whiskers extend to data points within a maximum of 1.5 times the interquartile range (IQR). Two-sided Wilcoxon signed-rank test was used to compute the P-value.
Figure 9:
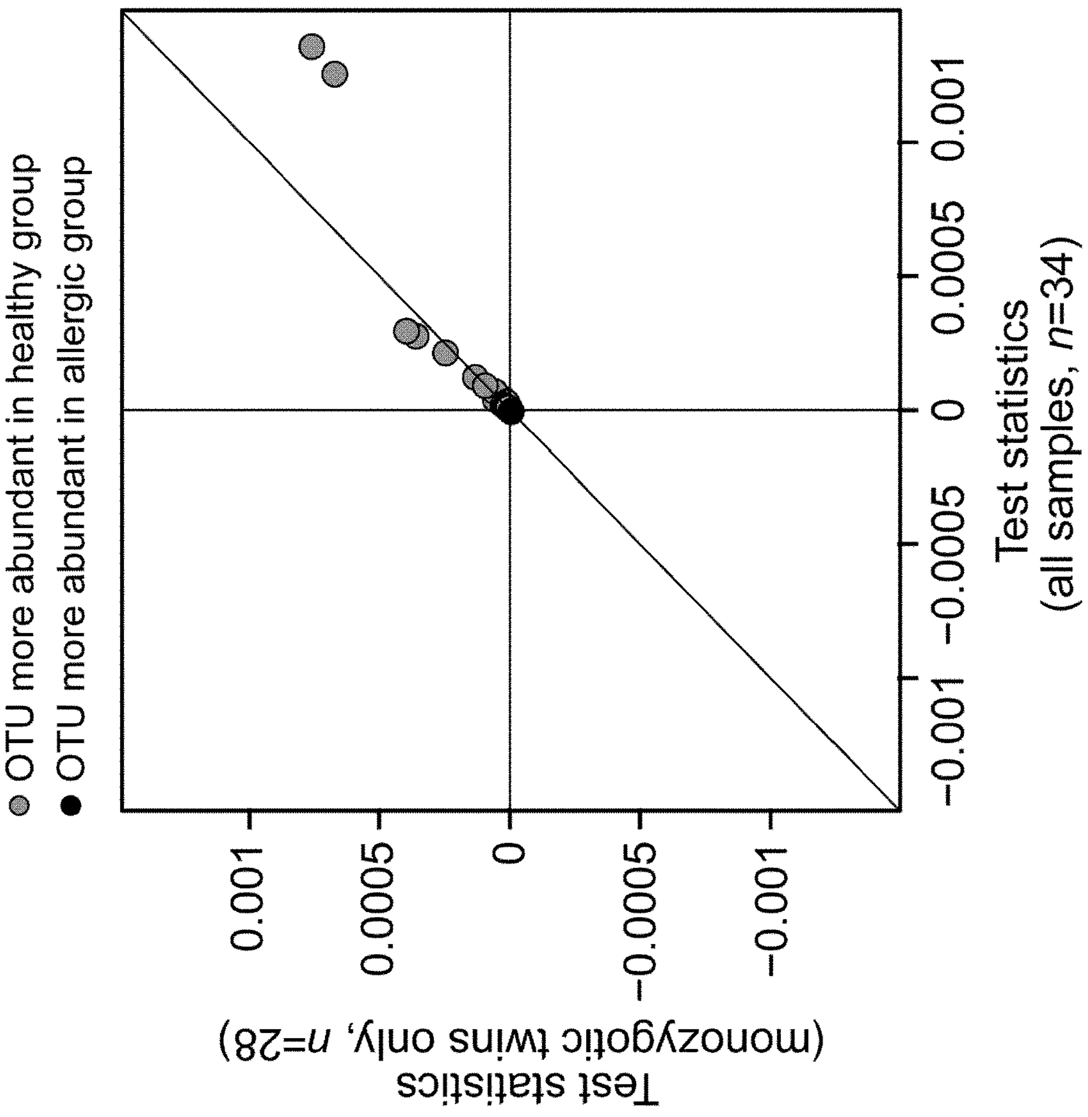
FIG. 9 shows that test statistics of the differentially abundant OTUs from all samples (n=34) is correlated with that computed from monozygotic twins only (n=28) comparing healthy and allergic groups.
Figure 10A:
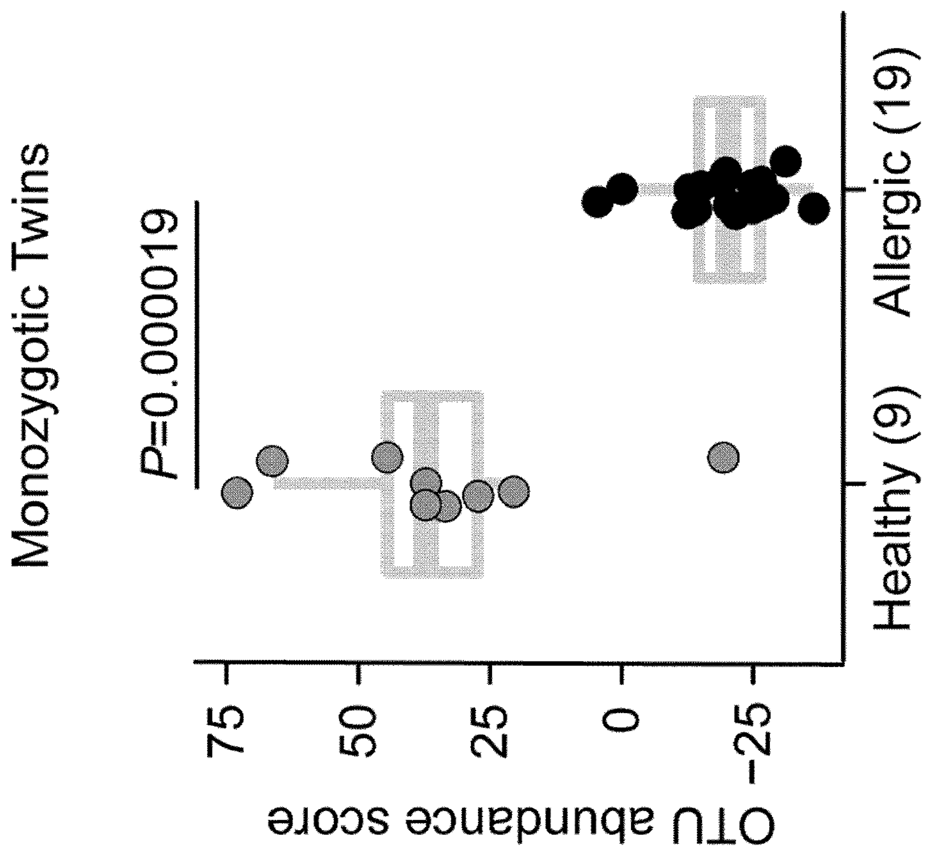
FIGS. 10A and 10B show that the aggregated OTU abundance score remains significant in healthy relative to allergic group in monozygotic twins (n=28).
Figure 10B:
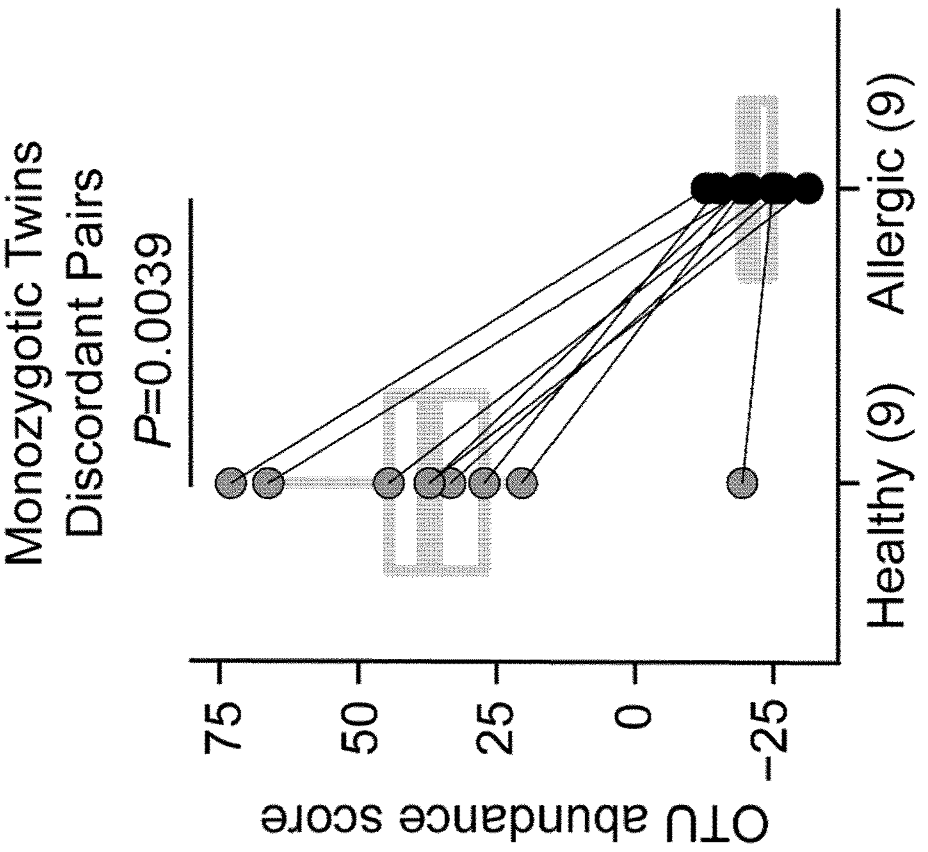
Figure 11:
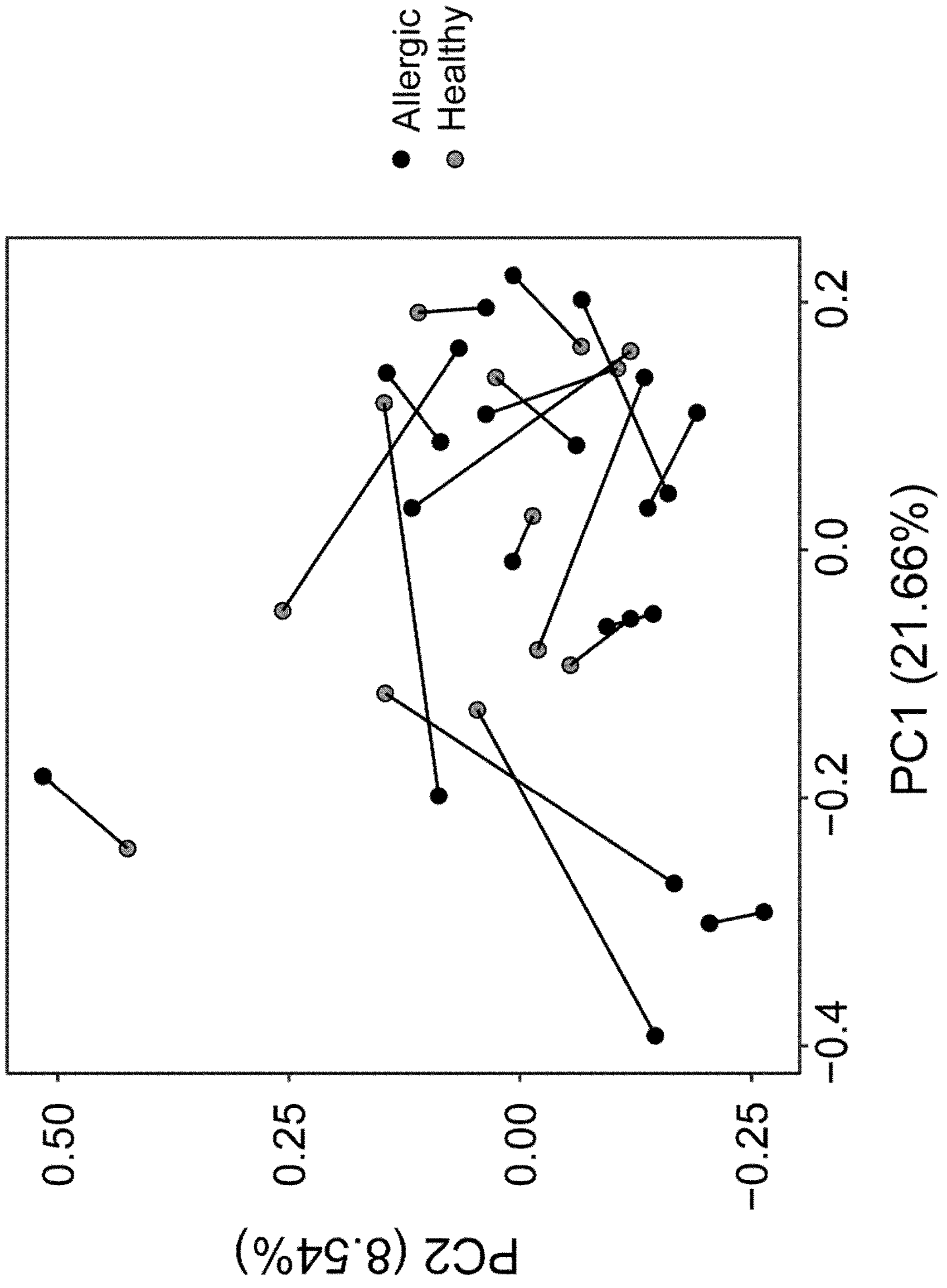
FIG. 11 shows a Principle Component Analysis (PCoA) of fecal metabolites. Shown is a plot of the first two principal component axes (PC1, PC2) explaining 21.66% and 8.54% of the total variance among 36 samples from the healthy and allergic groups. One sample (S5077) and the corresponding twin pair (#13) excluded from 16S analysis due to low sequencing depth was included for metabolite analysis. Each dot represents one sample. Line connects samples from the same twin pair. PCA was performed on normalized and log 10-transformed quantification of 1308 metabolites in total.

Next the microbial composition between allergic and healthy twin pairs was compared and 64 OTUs were identified as differentially abundant between the two groups, with 62 OTUs higher in healthy twins (hereafter referred to as "healthy-abundant" OTUs), and 2 OTUs higher in allergic twins (hereafter referred to as "allergic-abundant" OTUs); this is shown in FIG. 6 and in the binary presence/absence heatmap in FIG. 5. The 62 healthy-abundant OTUs were more abundant in the healthy twins compared with their allergic siblings, and the 2 allergic-abundant OTUs were more abundant in the allergic twins than their healthy siblings (FIG. 7A). 84% of the healthy-abundant OTUs were families in the Clostridia class, and annotated as Lachnospiraceae (n=21), Ruminococcaceae (n=28) or unclassified Clostridiales (n=4) (FIGS. 5, 6, and 7A). To develop an aggregated microbiome signature, a microbiota abundance score was calculated taking into consideration the relative abundance of the 64 differentially abundant OTUs and their change in direction between groups (see Methods). The OTU abundance score was significantly higher in healthy relative to allergic twins across all samples ($P<0.00001$) (FIG. 7B) or within discordant twins only ($P=0.00049$) (FIG. 8), as expected, since the score was calculated from preselected OTUs. Variance exists in the relative abundance scores for the discordant twin pairs (FIG. 8) because the majority of the differentially abundant OTUs are present in the healthy twins and absent in the allergic twins. If statistical comparisons are restricted to monozygotic twins only (14 pairs, 28 samples), the test statistics for the 62 healthy-abundant OTUs and the 2 allergic-abundant OTUs correlated with that of all twins (17 pairs, 34 samples) (FIG. 9), and the OTU abundance scores remained significantly different between the healthy and allergic twin groups (FIGS. 10A and 10B).

Example 2—Identification of Differential Enrichment of Fetal Metabolic Pathways Between Healthy and Allergic Twins

Methods

Metabolic Profiling Sample Preparation

The metabolic profiling of human fecal samples was performed by Metabolon Inc. (Morrisville, N.C., USA). All samples were maintained at −80° C. until processed. Samples were prepared using the automated MicroLab STAR® system from Hamilton Company (Reno, Nev., USA). Recovery standards were added prior to the first step in the extraction process for quality control purposes. To remove protein, to dissociate small molecules bound to protein or trapped in the precipitated protein matrix, and to recover chemically diverse metabolites, proteins were precipitated with methanol under vigorous shaking for 2 min (Glen Mills GenoGrinder 2000) followed by centrifugation. The resulting extract was divided into five fractions: two for analysis by two separate reverse phase (RP)/UPLC-MS/MS methods with positive ion mode electrospray ionization (ESI), one for analysis by RP/UPLC-MS/MS with negative ion mode ESI, one for analysis by HILIC/UPLC-MS/MS with negative ion mode ESI, and one sample reserved for backup. Samples were placed briefly on a TurboVap® (Zymark) to remove the organic solvent. The sample extracts were stored overnight under nitrogen before preparation for analysis.

Metabolic Profiling Sample QA/QC

Three types of controls were analyzed together with the experimental samples: (1) a pooled matrix sample generated by taking a small volume of each experimental sample as a technical replicate throughout the data set, (2) extracted water samples as process blanks, and (3) a cocktail of QC standards carefully chosen not to interfere with the measurement of endogenous compounds were spiked into every analyzed sample, allowing for monitoring of instrument performance and facilitating chromatographic alignment. Instrument variability was determined by calculating the median relative standard deviation (RSD) for the standards that were added to each sample prior to injection into the mass spectrometers (3% median RSD in this study). Overall process variability was determined by calculating the median RSD for all endogenous metabolites (i.e., non-instrument standards) present in 100% of the pooled matrix samples (7% median RSD in this study). All 36 fecal samples passed QC and were included in the metabolic data analysis.

Ultrahigh Performance Liquid Chromatography-Tandem Mass Spectroscopy (UPLC-MS/MS)

All methods utilized a Waters ACQUITY ultra-performance liquid chromatography (UPLC) and a Thermo Scientific Q-Exactive high-resolution/accurate mass spectrometer interfaced with a heated electrospray ionization (HESI-II) source and Orbitrap mass analyzer operated at 35,000 mass resolution. The sample extract was dried and reconstituted in solvents compatible to each of the four methods. Each reconstitution solvent contained a series of standards at fixed concentrations to ensure injection and chromatographic consistency. One aliquot was analyzed using acidic positive ion conditions, chromatographically optimized for more hydrophilic compounds. In this method, the extract was gradient eluted from a C18 column (Waters UPLC BEH C18-2.1×100 mm, 1.7 μm) using water and methanol, containing 0.05% perfluoropentanoic acid (PFPA) and 0.1% formic acid (FA). Another aliquot was also analyzed using acidic positive ion conditions; however, it was chromatographically optimized for more hydrophobic compounds. In this method, the extract was gradient eluted from the same previously mentioned C18 column using methanol, acetonitrile, water, 0.05% PFPA, and 0.01% FA, and was operated at an overall higher organic content. Another aliquot was analyzed using basic negative ion optimized conditions using a separate dedicated C18 column. The basic extracts were gradient eluted from the column using methanol and water, however with 6.5 mM ammonium bicarbonate at pH 8. The fourth aliquot was analyzed via negative ionization following elution from a HILIC column (Waters UPLC BEH Amide 2.1×150 mm, 1.7 μm) using a gradient consisting of water and acetonitrile with 10 mM ammonium formate, pH 10.8. The MS analysis alternated between MS and data-dependent MSn scans using dynamic exclusion. The scan range varied slighted between methods but covered 70-1000 m/z.

Compound Identification and Curation

UPLC MS/MS raw data were extracted, peak-identified, and QC-processed by Metabolon Inc. (Morrisville, N.C., USA). Compounds were identified by comparing them to internal library entries of purified standards or recurrent unknown entities. The library was based on authenticated standards that contain the retention time/index (RI), mass-to-charge ratio (m/z), and chromatographic data (including MS/MS spectral data) on all molecules present in the library. Furthermore, biochemical identifications were based on three criteria: (1) retention index within a narrow RI window of the proposed identification, (2) accurate mass match to the library±10 ppm, and (3) the MS/MS forward and reverse scores between the experimental data and authentic standards. The MS/MS scores were based on comparing the ions in the experimental spectrum to the ions in the library spectrum. While there may be similarities between these molecules based on one of these factors, the use of all three data points can be utilized to distinguish and differentiate biochemicals. More than 3300 commercially available purified standard compounds were acquired and registered for analysis on all platforms to determine their analytical characteristics. Additional mass spectral entries were created for structurally unnamed biochemicals, which were identified by virtue of their recurrent nature (both chromatographic and mass spectral). Entries were further processed by manual curation to ensure accurate and consistent identification of true chemical entities, and to remove those representing system artifacts, mis-assignments, and background noise.

Metabolite Quantification and Normalization

UPLC MS/MS peaks were quantified by area under the ROC curve (AUC). Data were normalized to correct for variations resulting from instrument inter-day tuning differences using median-centered method. In this method, each compound was corrected in run-day blocks by registering the median as 1.00 and normalizing each data point proportionately, hereafter referred to as block correction, and further normalized to account for differences in metabolite levels due to differences in the quantities of material in each sample.

Differentially Abundant Metabolite Identification

Metabolites differentially abundant across all samples from the allergic and healthy twin groups (n=36) were identified using Welch's two-sample t-test. A total of 1,308 metabolites were quantified. After removing metabolites without pathway annotation, 992 metabolites were kept for statistical comparisons. Among those, in comparing allergic with healthy groups, 97 metabolites reached a significance level of P<0.10 and were kept for further analysis. After BH-method correction for multiple testing, none of the metabolites passed FDR 0.10, potentially due to small sample size. Additionally, the abundance of metabolites was compared between the two groups within discordant twins only (n=26, from 13 twin pairs) using paired t-test. The sample (S5077) and the corresponding twin pair (#13) excluded from microbial 16S data analysis was kept in the metabolic profiling analysis.

Correlation of Bacterial Taxa and Metabolite Abundance

Figure 17:
FIG. 17 shows correlation between the 64 OTUs from FIG. 6 and the 97 metabolites from FIGS. 13A and 13B. Metabolites are shown on the row in the format of "COMP_ID|Biochemical_Name|Super_Pathway|Sub_Pathway", and OTU IDs are shown on the column in the format of "OTU_ID|Family".
Figure 18:
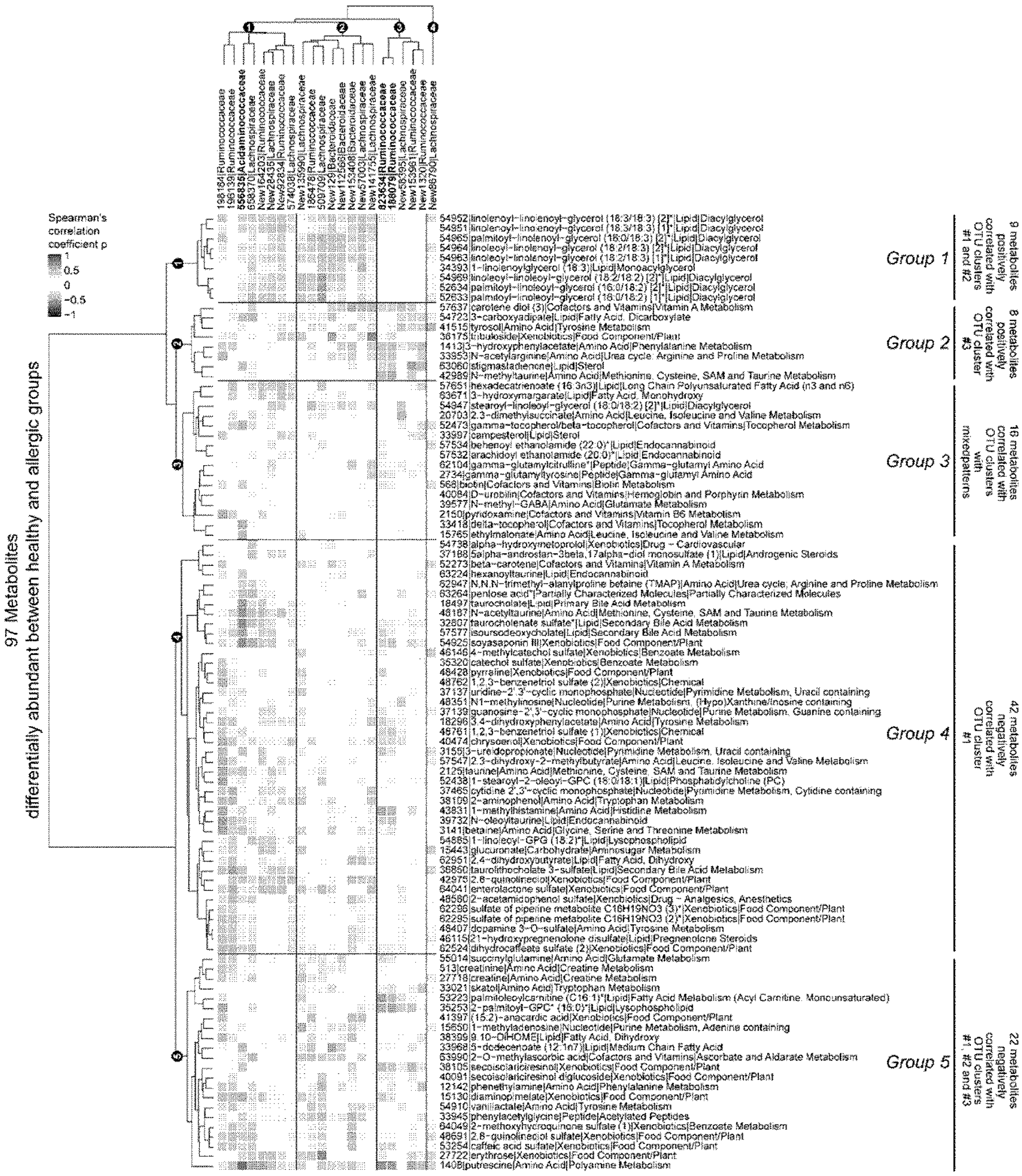
FIG. 18 shows the OTUs differentially abundant between healthy and allergic groups that are correlated with different sets of metabolites and pathways. Of 64 OTUs, 4 OTUs showed a strong correlation with the 97 metabolites. The filtering of OTUs is illustrated in the analytical workflow (FIG. 1). Metabolites are shown on the row in the format of "COMP_ID|Biochemical_Name|Super_Pathway|Sub-_Pathway", and OTU IDs are shown on the column in the format of "OTU_ID|Family". 3 OTUs that match to bacteria species at >99% identity are bolded. OTUs were divided into 4 clusters based on same height on the dendrogram shown on the column using R function cut.tree. Similarly, metabolites were divided into 5 groups based on same height on the dendrogram shown on the row. Annotation to metabolite groups 1 to 5 were added based on the distribution of Spearman's correlation coefficient ρ among the healthy-abundant OTU clusters 1 to 3 consisting of 21 OTUs. Cluster 4 only contains 1 OTU from allergic-abundant bacteria, hence was not used for metabolite group annotation. Spearman's correlation was used.

Pairwise Spearman's rank correlation was computed among the 64 OTUs and 97 metabolites differentially abundant between allergic and healthy twins (FIG. 17). OTUs were further prioritized using the following approach. First, OTUs were filtered for those that showed a correlation at P<0.05 with at least 5 differentially abundant metabolites from the designated group. For potentially healthy-abundant OTUs (more abundant in the healthy group), they were correlated with metabolites from group "Up in healthy" or "Down in healthy"; the potentially allergic-abundant OTUs (more abundant in allergic group) were correlated with metabolites from group "Up in allergic" or "Down in allergic." Second, OTUs that passed step 1 were filtered further for those that showed a relatively consistent trend of positive correlation (Spearman's p>0.20) across at least 30% of the metabolites from the designated group. For healthy-abundant OTUs, they were correlated with metabolites from group "Up in healthy" and "Down in allergic" joined; the allergic-abundant OTUs were correlated with metabolites from group "Up in allergic" and "Down in healthy" together. Third, OTUs that passed steps 1 and 2 were further filtered to select those at P<0.05 from the DS-FDR method comparing allergic to healthy groups across all samples. Of the 64 OTUs, 22 passed these correlation filters and are shown in FIG. 18. After a BLAST search of assembled 16S sequences against the NCBI database (16S ribosomal RNA, Bacteria and Archaea) (accessed 09/12/2020) using blastn (20), 3 of 22 OTUs were matched to bacterial species at 99% or higher sequence identity: OTU556835, matched to *Phascolarctobacterium faecium* (accession ID NR_026111.1, 99.21% identity); OTU188079 and OTU823634, both matched *Ruminococcus bromii* (accession ID NR_025930.1; 99.21% identity).

Statistics

The Discrete False-Discovery Rate (DS-FDR) method (29) was used to identify differentially abundant OTUs by comparing allergic to healthy twins. Welch's two-sample t-test was used to identify differentially abundant metabolites comparing allergic to healthy twins. Unless stated otherwise, for comparing groups using all samples, Wilcoxon rank-sum test was used; if only within discordant twins, Wilcoxon signed-rank test was used. For metabolites, paired t-test was used to compare its abundance between the two groups within discordant twins after log 10 transformation. metabolic sub-pathway enrichment was analyzed using the Hypergeometric test, requiring at least 2 metabolites annotated with each sub-pathway. Following Wilcoxon rank-sum test or Wilcoxon signed-rank test, and Hypergeometric test, we used the BH-FDR method (31) for multiple testing correction. For pairwise comparisons of metabolite Spearman's correlation coefficients between OTU clusters, Tukey's honestly significant difference (HSD) test was used. Other statistical tests were used as indicated in the text and in the Brief Description of the Drawings. For comparison of healthy and allergic groups across all samples in 16S analysis, qPCR validation, and Spearman's correlation between OTUs and metabolites, a P-value less than 0.05 was considered significant. For comparison of healthy and allergic groups across all samples in metabolite analysis, comparison of healthy and allergic groups within discordant twin pairs in 16S or metabolite analysis, and SCFA analysis, a P-value less than 0.10 was considered significant. For metabolite sub-pathway enrichment analysis, an FDR-adjusted P-value less than 0.10 was considered significant. All tests were two-sided.

Results

Figure 12:
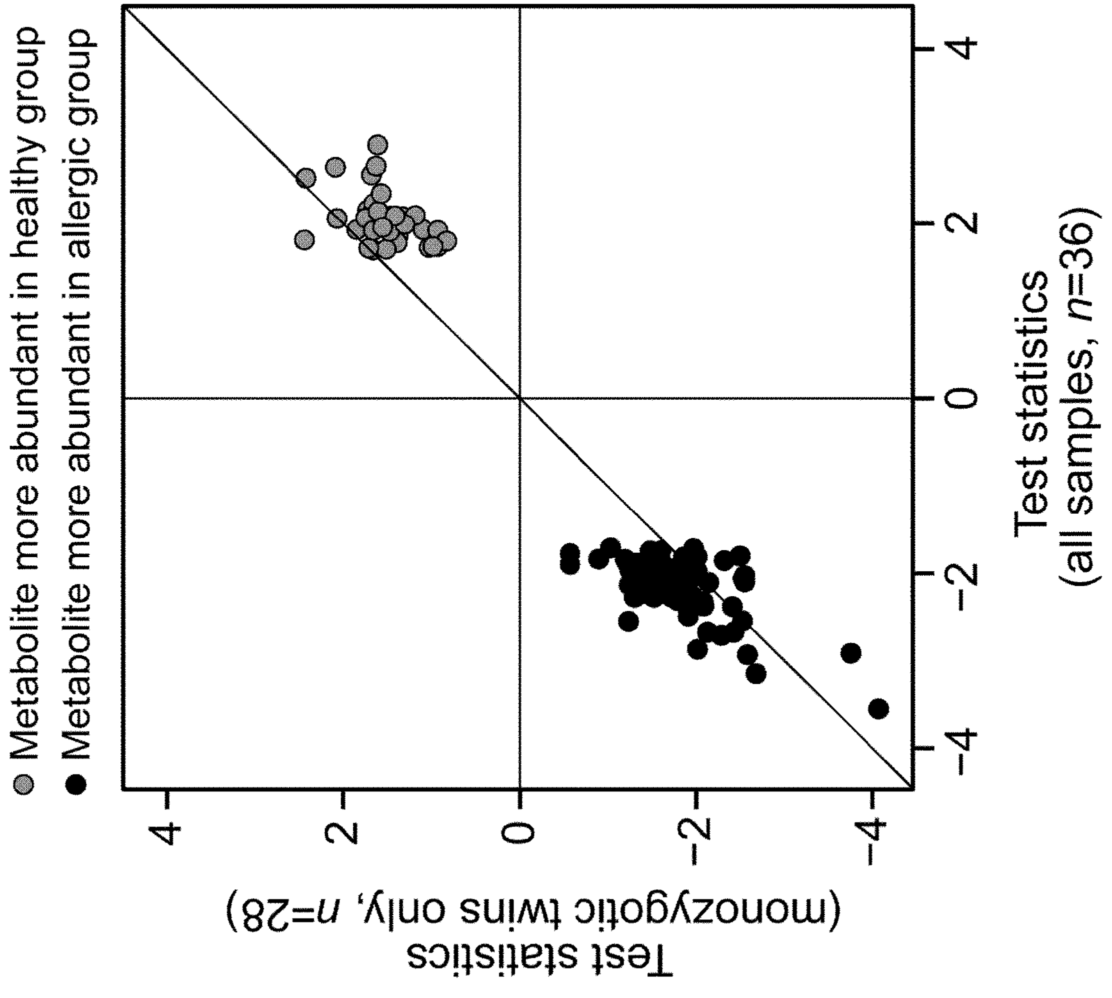
FIG. 12 shows that test statistics of the differentially abundant metabolites from all samples (n=36) is correlated with that computed from monozygotic twins only (n=28) comparing healthy and allergic groups. For each of the 97 metabolites differentially abundant between healthy and allergic groups using all samples, test statistics was re-computed using samples from monozygotic twins only. Two-sided Wilcoxon signed-rank test was used.
Figure 13A:
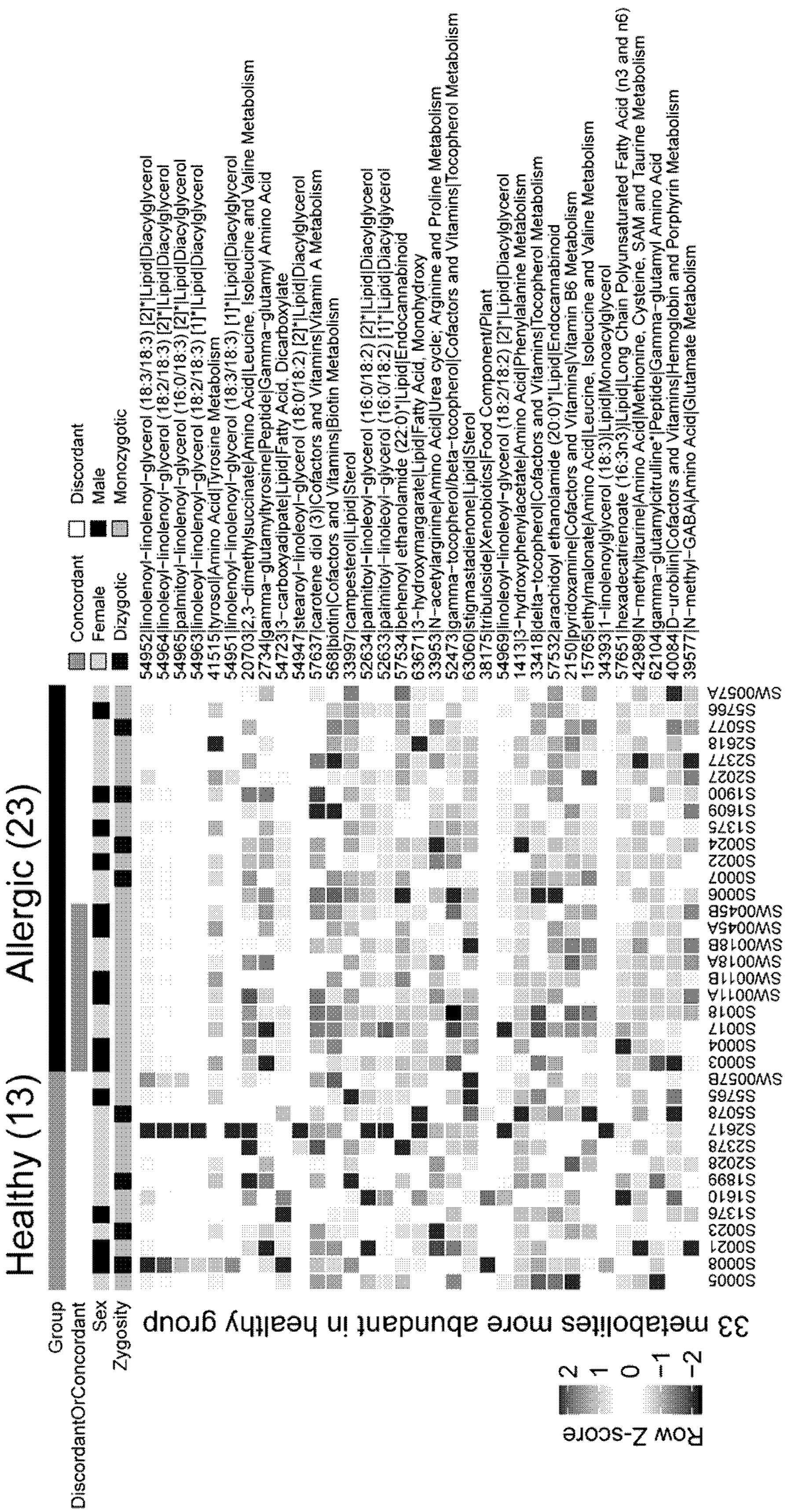
FIGS. 13A and 13B show data demonstrating that healthy and allergic twins exhibit differential enrichment in fecal metabolic pathways.
Figure 13B:
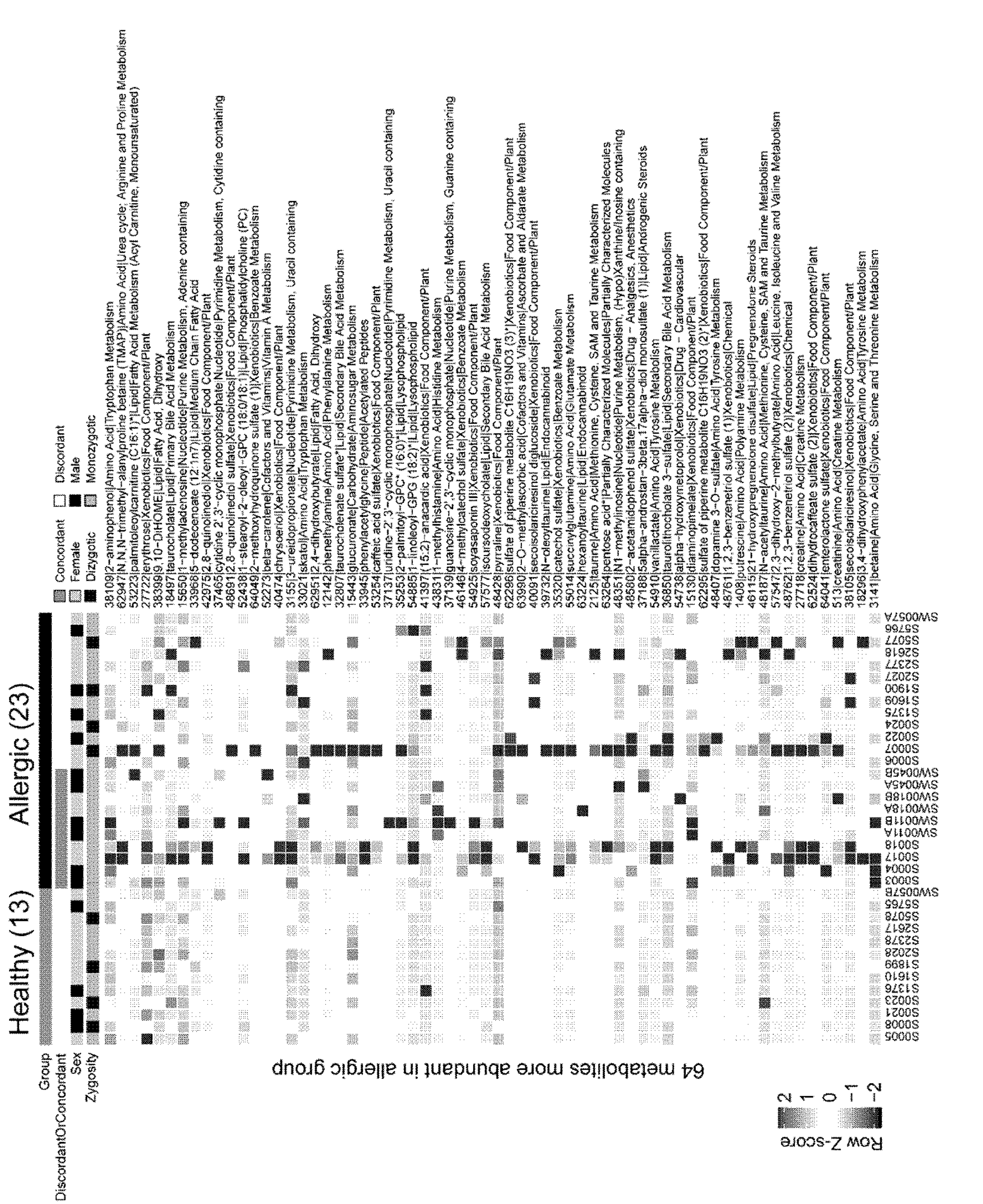

Bacteria produce many metabolites that modulate the immune system and profoundly influence human health (32). Limited data exist on unbiased systematic profiling of fecal metabolites in patients with and without food allergy. LC-MS/MS was performed to measure the abundance of compounds in the same set of fecal samples from the twin cohort. 97 metabolites were identified as differentially abundant between the healthy and allergic twins, with 33 more abundant in healthy twins, and 64 more abundant in allergic twins (FIGS. 13A and 131B; Table 4). When statistical comparisons were restricted to monozygotic twins only (14 pairs, 28 samples), the test statistics for the 33 healthy-abundant metabolites and the 64 allergic-abundant metabolites correlated with that of all samples (18 pairs, 36 samples) (FIG. 12, Table 4). Among these 97 metabolites, 32 (16 higher in healthy, 16 higher in allergic) also reached a significance level of 0.10 within discordant twin pairs only (FIGS. 16A-16H).

TABLE 4

List of 97 metabolites with known pathway annotation identified herein as differentially abundant between healthy and allergic twins

| CAS | Mass | Biochemical Name | Pubchem ID |
|---|---|---|---|
| 60-27-5 | 114.0662 | creatinine | 588 |
| 58-85-5 | 245.0955 | biotin | 171548 |
| 110-60-1 | 89.1073 | putrescine | 1045 |
| 621-37-4 | 151.0401 | 3-hydroxyphenylacetate | 12122 |
| 107-35-7 | 126.022 | taurine | 1123 |
| 58052-48-5 | 169.0972 | pyridoxamine | 1052 |
| 7432-23-7 | 311.1238 | gamma-glutamyltyrosine | 94340 |
| 107-43-7 | 118.0863 | betaine | 247 |

TABLE 4-continued

List of 97 metabolites with known pathway annotation identified herein as differentially abundant between healthy and allergic twins

| CAS | Mass | Biochemical Name | Pubchem ID |
|---|---|---|---|
| 462-88-4 | 133.0608 | 3-ureidopropionate | 111 |
| 64-04-0 | 122.0964 | phenethylamine | 1001 |
| 1476-39-7; 2577-62-0 | 191.1026 | diaminopimelate | 439283 |
| 207300-70-7 | 193.0354 | glucuronate | 444791 |
| 15763-06-1 | 282.1197 | 1-methyladenosine | 27476 |
| 601-75-2 | 131.035 | ethylmalonate | 11756 |
| 102-32-9 | 123.0452 | 3,4-dihydroxyphenylacetate | 547 |
| 145-42-6 | 514.2844 | taurocholate | 6675 |
| 13545-04-5 | 145.0506 | 2,3-dimethylsuccinate | 11848 |
| 57-00-1 | 132.0768 | creatine | 586 |
| 583-50-6 | 119.035 | erythrose | 94176 |
| | 279.6142 | taurocholenate sulfate* | NA |
| 83-34-1 | 130.0662 | skatol | 6736 |
| 119-13-1 | 402.3492 | delta-tocopherol | 92094 |
| 500-98-1 | 192.0666 | phenylacetylglycine | 68144 |
| 155-84-0 | 217.1295 | N-acetylarginine | 67427 |
| 2430-94-6 | 197.1547 | 5-dodecenoate (12:1n7) | 5312378 |
| 474-62-4 | 383.3672 | campesterol | 173183 |
| 124151-74-2 | 277.2173 | 1-linolenoylglycerol (18:3) | 53480978 |
| | 570.3413 | 2-palmitoyl-GPC* (16:0)* | 15061532 |
| 4918-96-1 | 188.9863 | catechol sulfate | 3083879 |
| 64936-83-0 | 280.6221 | taurolithocholate 3-sulfate | 440071 |
| 40632-52-8 | 305.018 | uridine-2',3'-cyclic monophosphate | 439715 |
| 15718-49-7 | 344.0402 | guanosine-2',3'-cyclic monophosphate | 92823 |
| | 371.1898 | 5alpha-androstan-3beta, 17alpha-diol monosulfate (1) | N/A |
| 15718-51-1 | 304.034 | cytidine 2',3'-cyclic monophosphate | 417654 |
| 29388-59-8 | 361.1657 | secoisolariciresinol | 65373 |
| 95-55-6 | 110.06 | 2-aminophenol | 5801 |
| 20316-62-5 | 593.1301 | tribuloside | 5320686 |
| 263399-34-4 | 313.2384 | 9,10-DiHOME | 9966640 |
| 1119-48-8 | 118.0863 | N-methyl-GABA | 70703 |
| 52514-04-2 | 388.2527 | N-oleoyltaurine | 6437033 |
| 3947-38-4 | 589.3021 | D-urobilin | 6276321 |
| 148244-82-0 | 685.2713 | secoisolariciresinol diglucoside | 9917980 |
| 491-71-4 | 299.0561 | chrysoeriol | 5280666 |
| 11034-77-8 | 343.2279 | (15:2)-anacardic acid | 11824131 |
| 501-94-0 | 137.0608 | tyrosol | 10393 |
| 15450-76-7 | 162.055 | 2,8-quinolinediol | 97250 |
| 107-68-6 | 138.023 | N-methyltaurine | 7882 |
| 501-75-7 | 126.1026 | 1-methylhistamine | 3614 |
| 1164-98-3 | 245.0671 | 21-hydroxypregnenolone disulfate | 134595 |
| | 203.002 | 4-methylcatechol sulfate | N/A |
| | 166.018 | N-acetyltaurine | 159864 |
| 20245-33-4 | 283.1037 | N1-methylinosine | 65095 |
| | 232.0285 | dopamine 3-O-sulfate | 122136 |
| 74509-14-1 | 253.1194 | pyrraline | 122228 |
| 40712-60-5 | 230.0129 | 2-acetamidophenol sulfate | 181671 |
| | 239.9972 | 2,8-quinolinediol sulfate | N/A |
| | 204.9812 | 1,2,3-benzenetriol sulfate (1) | N/A |
| | 204.9812 | 1,2,3-benzenetriol sulfate (2) | N/A |
| 7235-40-7 | 552.4312 | beta-carotene | 5280489 |
| 56421-10-4 | 788.6164 | l-stearoyl-2-oleoyl-GPC (18:0/18:1) | N/A |
| | 416.3643 | gamma-tocopherol/beta-tocopherol | N/A |
| | 610.5405 | palmitoyl-linoleoyl-glycerol (16:0/18:2) [1]* | 9543695 |
| | 610.5405 | palmitoyl-linoleoyl-glycerol (16:0/18:2) [2]* | N/A |
| | 398.3265 | palmitoleoylcamitine (C 16:l)* | 71464547 |
| | 258.9918 | caffeic acid sulfate | N/A |
| 923-42-2 | 189.0405 | 3-carboxyadipate | 222467 |
| 56392-16-6 | 284.1856 | alpha-hydroxymetoprolol | 114962 |
| | 507.2728 | 1-linoleoyl-GPG (18:2)* | NA |
| 2475-56-1 | 211.0612 | vanillactate | 160637 |
| 55304-02-4 | 795.4536 | soyasaponin III | N/A |
| | 638.5718 | stearoyl-linoleoyl-glycerol (18:0/18:2) [2]* | N/A |
| | 630.5092 | linolenoyl-linolenoyl-glycerol (18:3/18:3) [1]* | N/A |
| | 630.5092 | linolenoyl-linolenoyl-glycerol (18:3/18:3) [2]* | N/A |
| | 632.5249 | linoleoyl-linolenoyl-glycerol (18:2/18:3) [1]* | N/A |

TABLE 4-continued

List of 97 metabolites with known pathway annotation identified herein as differentially abundant between healthy and allergic twins

| CAS | Mass | Biochemical Name | Pubchem ID |
|---|---|---|---|
| | 632.5249 | linoleoyl-linolenoyl-glycerol (18:2/18:3) [2]* | N/A |
| | 608.5249 | palmitoyl-linolenoyl-glycerol (16:0/18:3) [2]* | N/A |
| | 634.5405 | linoleoyl-linoleoyl-glycerol (18:2/18:2) [2]* | N/A |
| | 247.0925 | succinylglutamine | N/A |
| | 356.3523 | arachidoyl ethanolamide (20:0)* | 3787294 |
| | 384.3836 | behenoyl ethanolamide (22:0)* | 3023585 |
| 14868-24-7 | 133.0506 | 2,3-dihydroxy-2-methylbutyrate | 301941 |
| 78919-26-3 | 391.2854 | isoursodeoxycholate | 127601 |
| | 568.4279 | carotene diol (3) | N/A |
| 7561-64-0 | 249.186 | hexadecatrienoate (16:3n3) | 5312428 |
| | 305.1456 | gamma-glutamylcitrulline* | N/A |
| | 352.086 | sulfate of piperine metabolite C16H19NO3 (2)* | N/A |
| | 352.086 | sulfate of piperine metabolite C16H19NO3 (3)* | N/A |
| | 261.0074 | dihydrocaffeate sulfate (2) | 49844181 |
| | 229.1547 | N,N,N-trimethyl-alanylproline betaine (TMAP) | N/A |
| 1518-62-3 | 119.035 | 2,4-dihydroxybutyrate | 192742 |
| | 411.3622 | stigmastadienone | 6442194 |
| | 222.0806 | hexanoyltaurine | 2245940 |
| | 165.0405 | pentose acid* | N/A |
| 40165-89-7 | 285.2435 | 3-hydroxymargarate | 93220 |
| 17860-87-6 | 189.0405 | 2-O-methylascorbic acid | 99779 |
| | 377.07 | enterolactone sulfate | N/A |
| 60-27-5 | 218.9969 | 2-methoxyhydroquinone sulfate (1) | N/A |

Figure 14A:
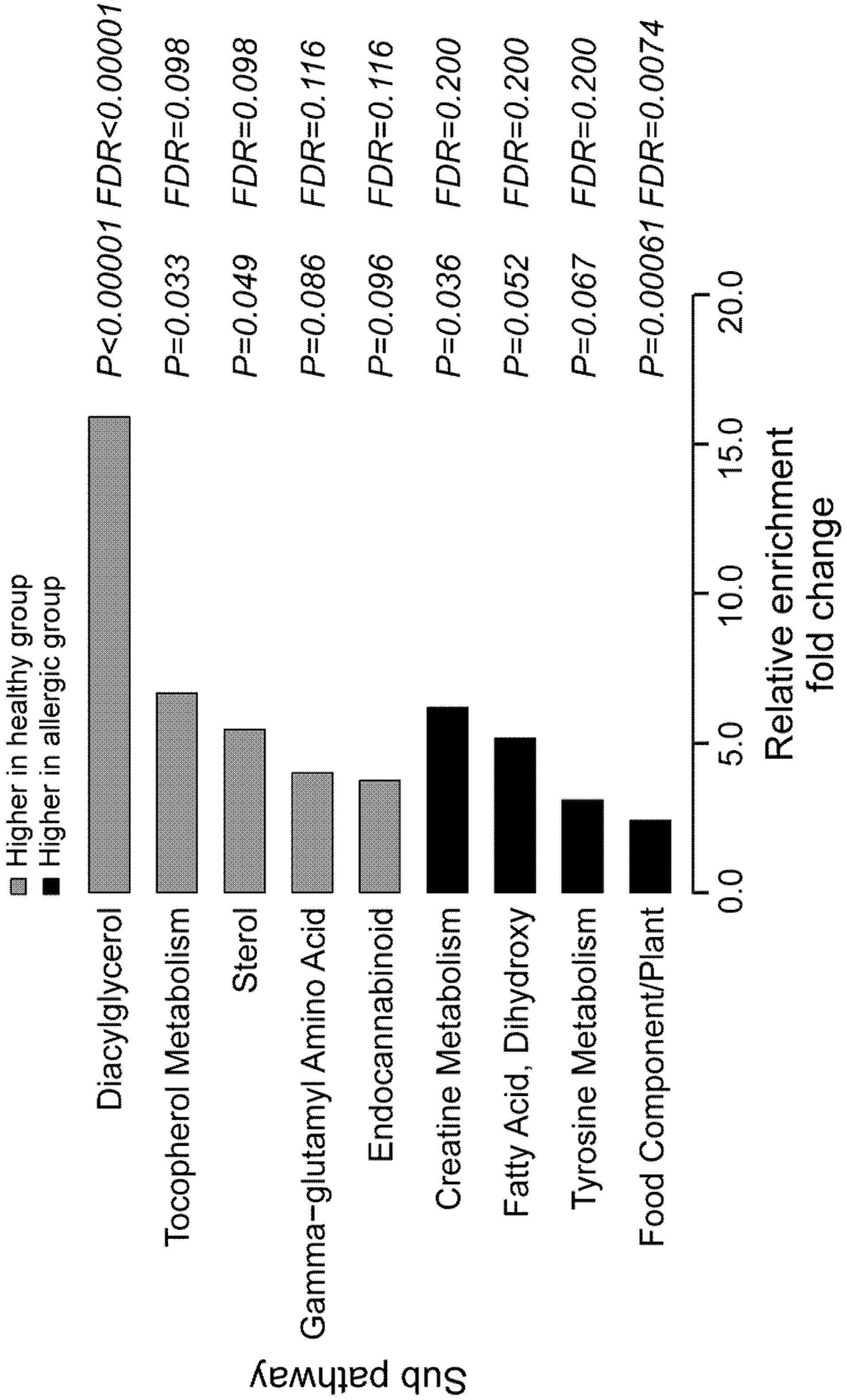
FIGS. 14A-14C show that distinct metabolic pathways are enriched in healthy and allergic twins.
Figure 14B:
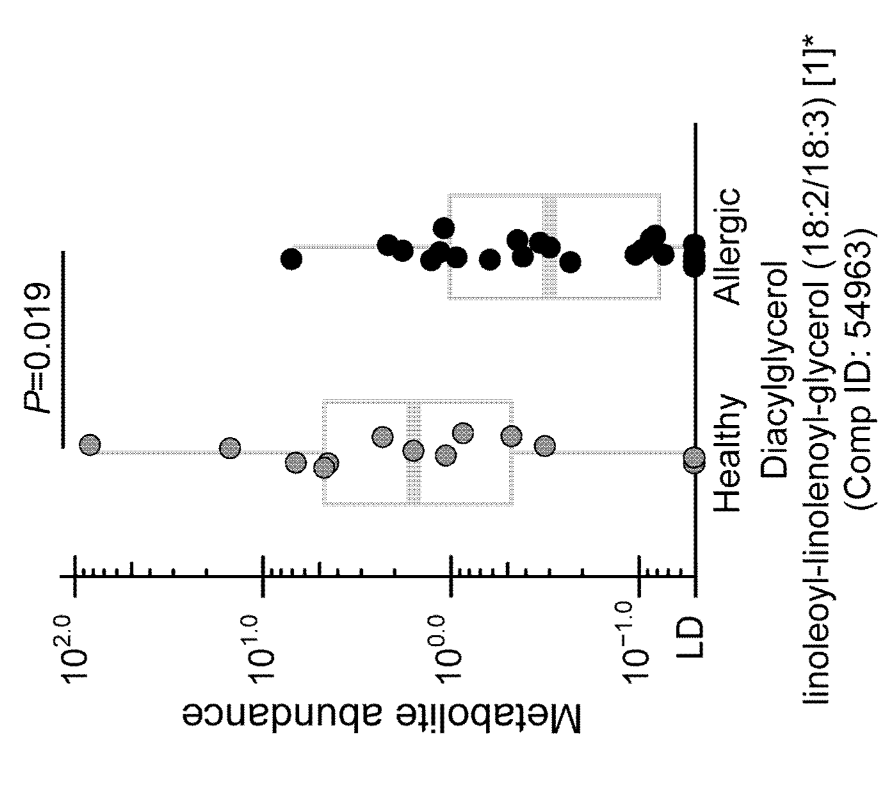
Figure 14C:
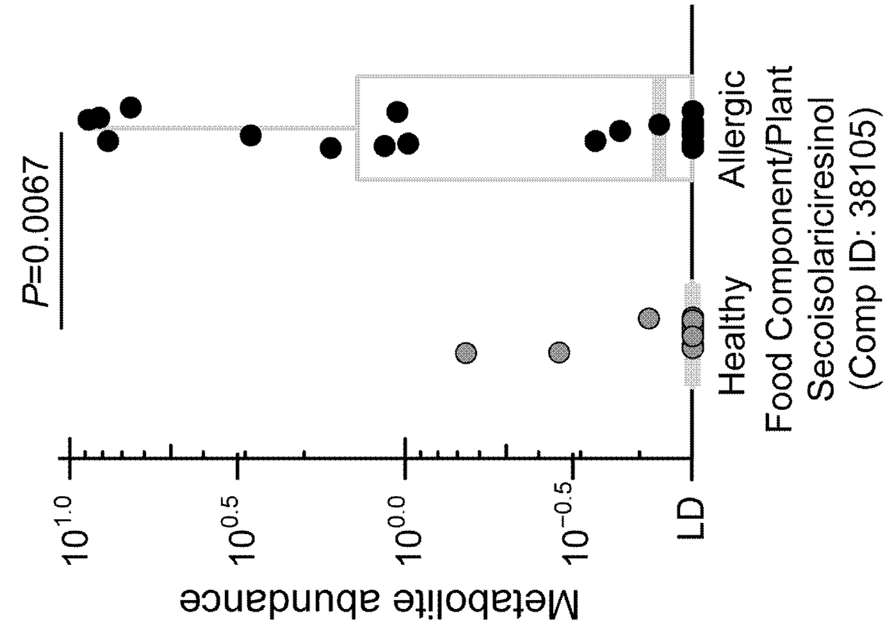
Figure 15A:
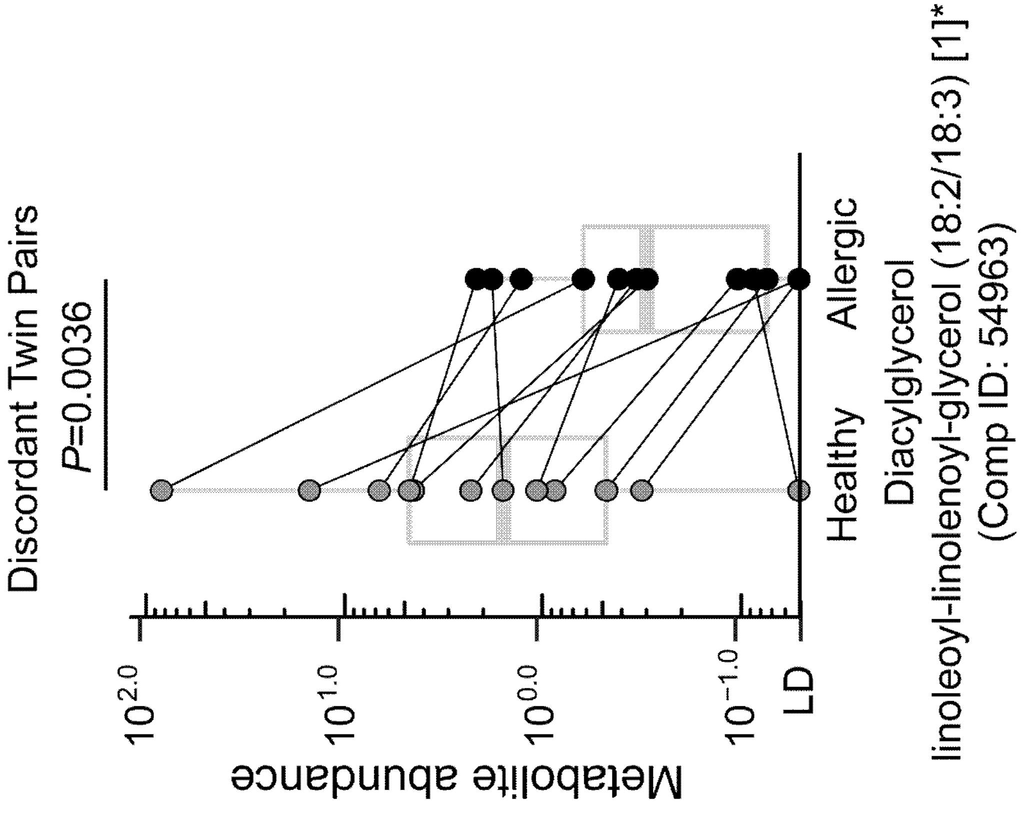
FIGS. 15A and 15B show representative examples of metabolites significantly higher in healthy relative to allergic group (as shown in FIGS. 14B and 14C) in the discordant twin pairs only (FIG. 15A), or vice versa (FIG. 15B) (13 pairs, n=26). Units shown on the y-axis in FIGS. 15A and 15B represent the normalized raw area counts of UPLC MS/MS peaks, rescaled to set the median equal to 1.00 for each biochemical. Each dot denotes one sample. The bounds of the boxes represent the 25th and 75th percentiles, the horizontal center line indicates the median, and the whiskers extend to data points within a maximum of 1.5 times the IQR. Two-sided paired t-test was used to compute the P-values.
Figure 15B:
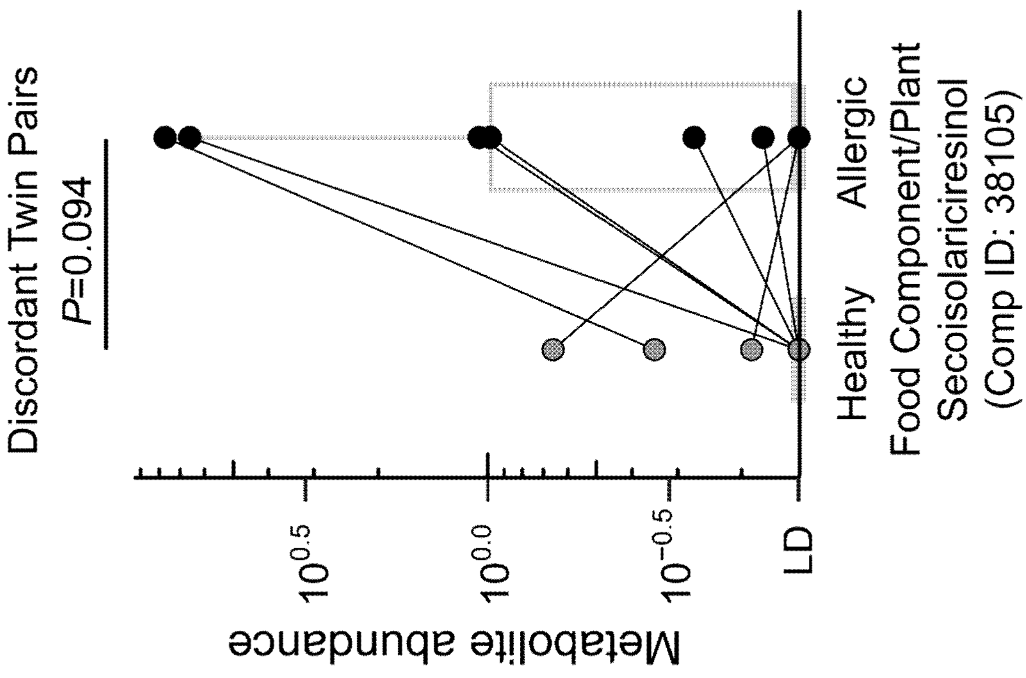
Figure 16A:
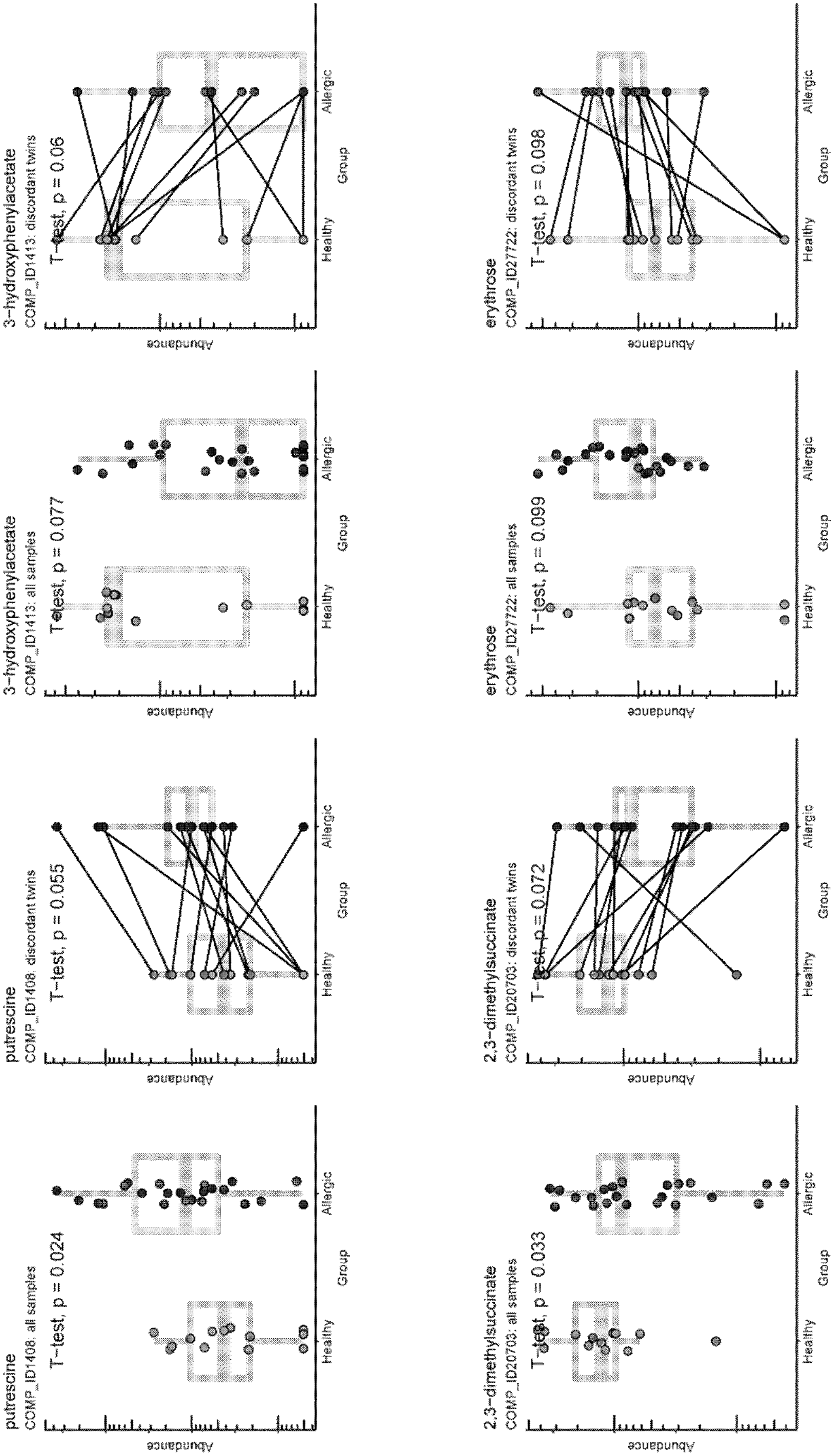
FIGS. 16A-16H show the differential abundance of 32 metabolites between healthy and allergic twin groups total (n=36) or in discordant twin pairs only (n=26 discordant pairs). Shown is a subset of the 97 metabolites differentially abundant between healthy and allergic groups across all 36 samples. The one sample (S5077) and the corresponding twin pair (#13) excluded from 16S analysis due to low sequencing depth was included for metabolite analysis, forming 13 discordant twin pairs. Four metabolites are shown per page. For each metabolite, two panels are shown: comparison between the two groups across all samples (left, n=36), and within discordant twin pairs only (right, 13 pairs, n=26), hence eight panels per page. P-values are shown in each panel. For comparison across all samples, two-sided Welch Two-Sample t-test was used; for comparison within discordant twin pairs only, two-sided paired t-test was used. All measure was normalized and log 10-transformed before statistical tests. The bounds of the boxes represent the 25th and 75th percentiles, the horizontal center line indicates the median, and the whiskers extend to data points within a maximum of 1.5 times the IQR.
Figure 16B:
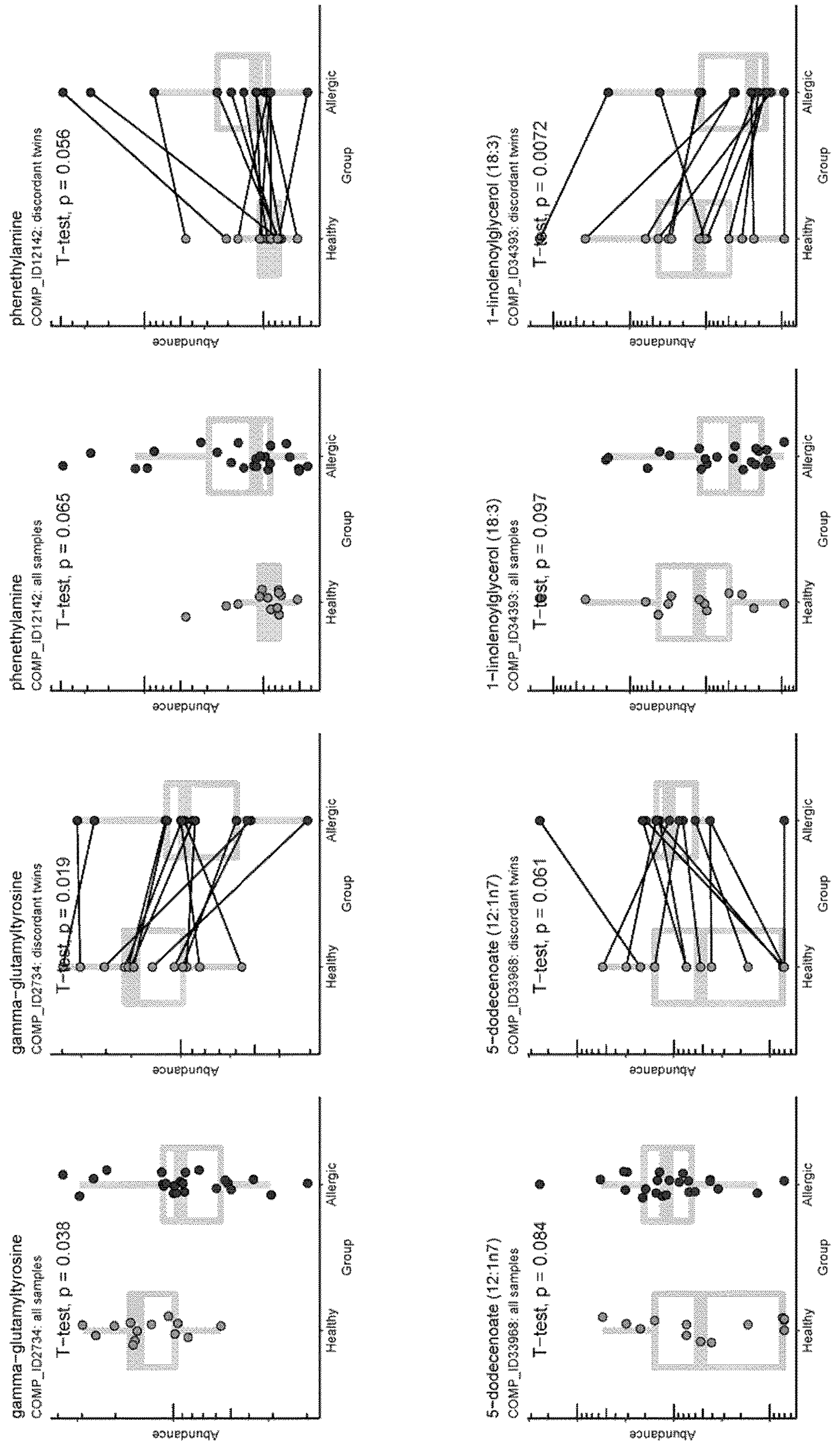
Figure 16C:
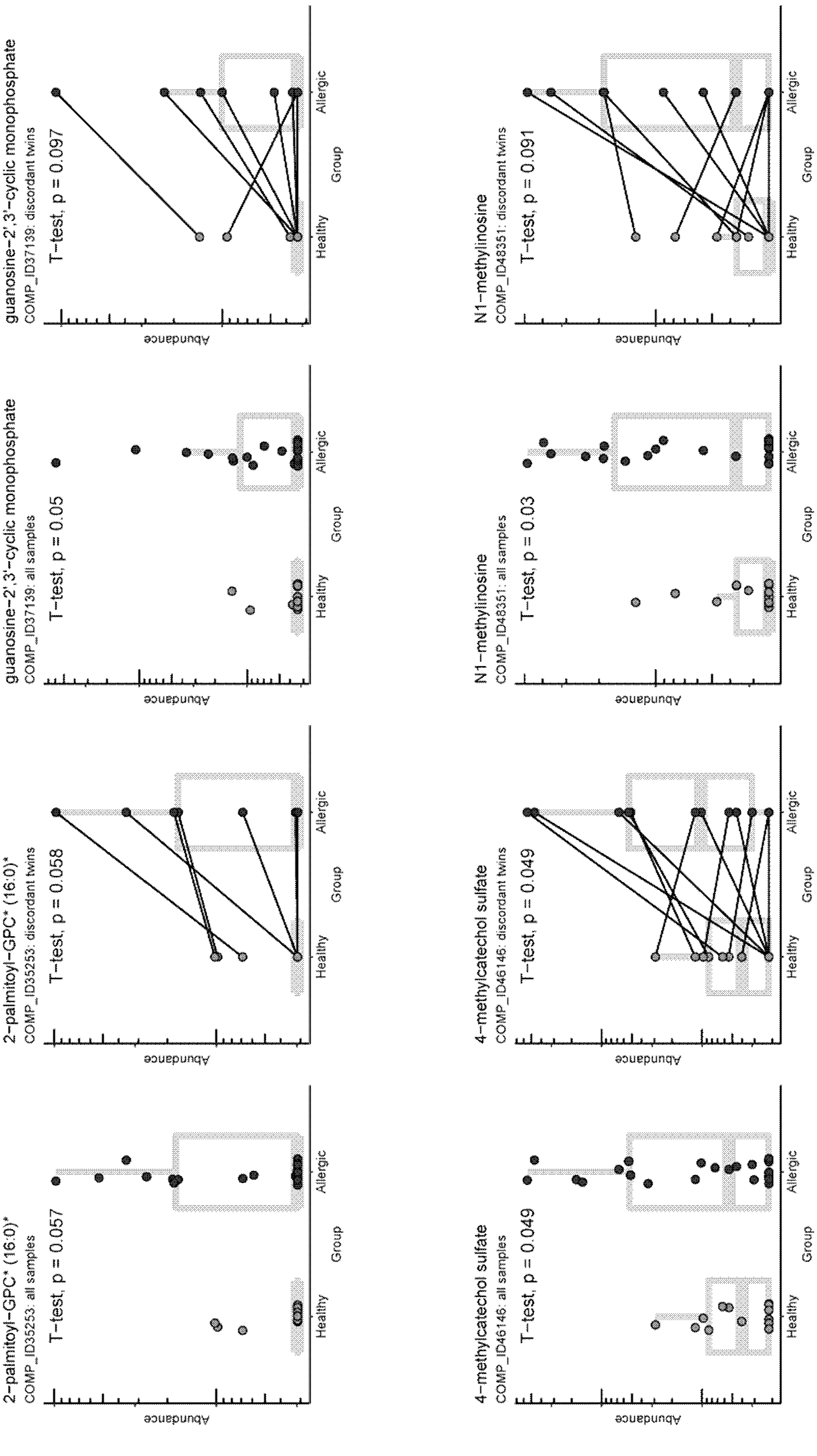
Figure 16D:
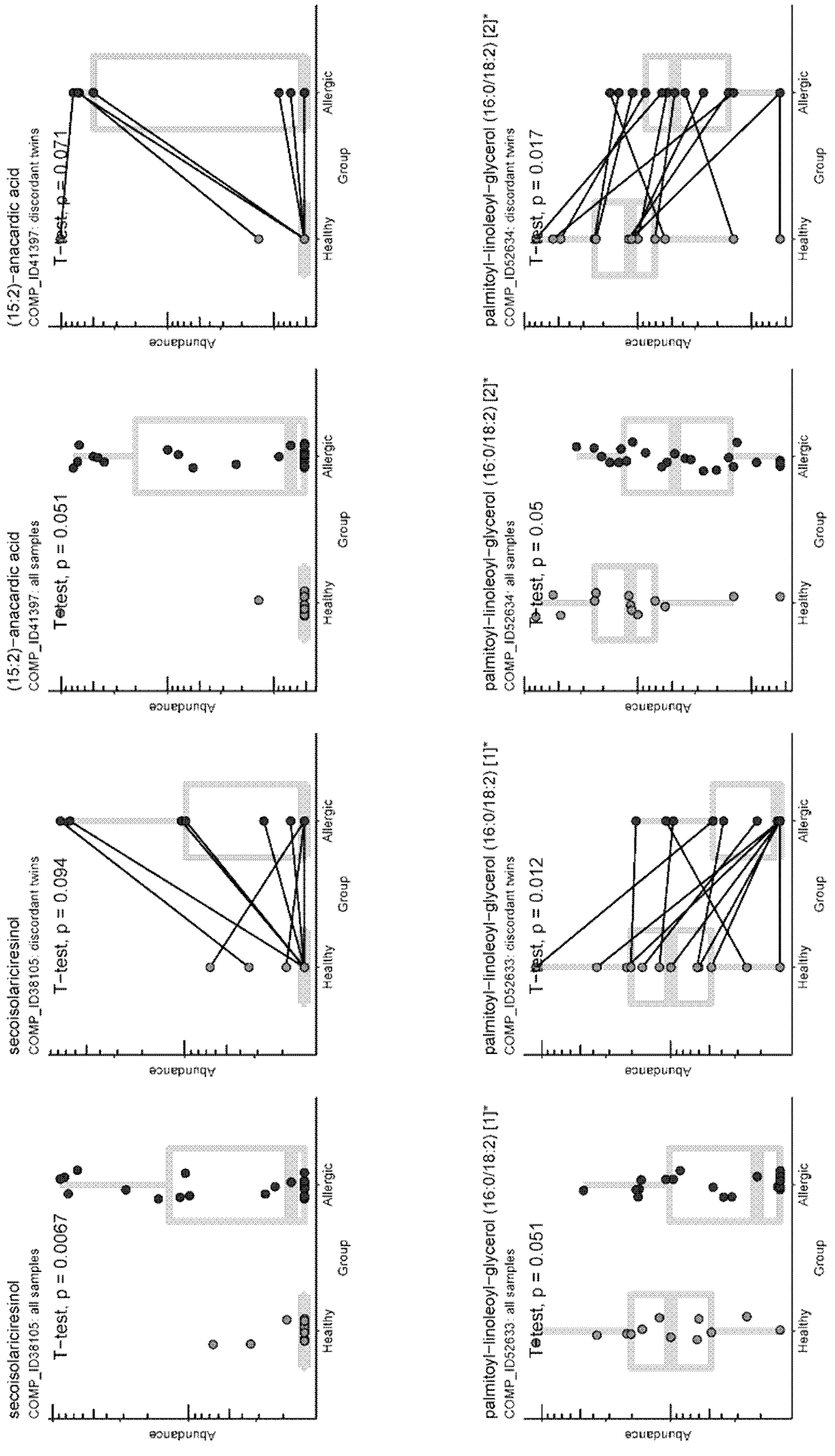
Figure 16E:
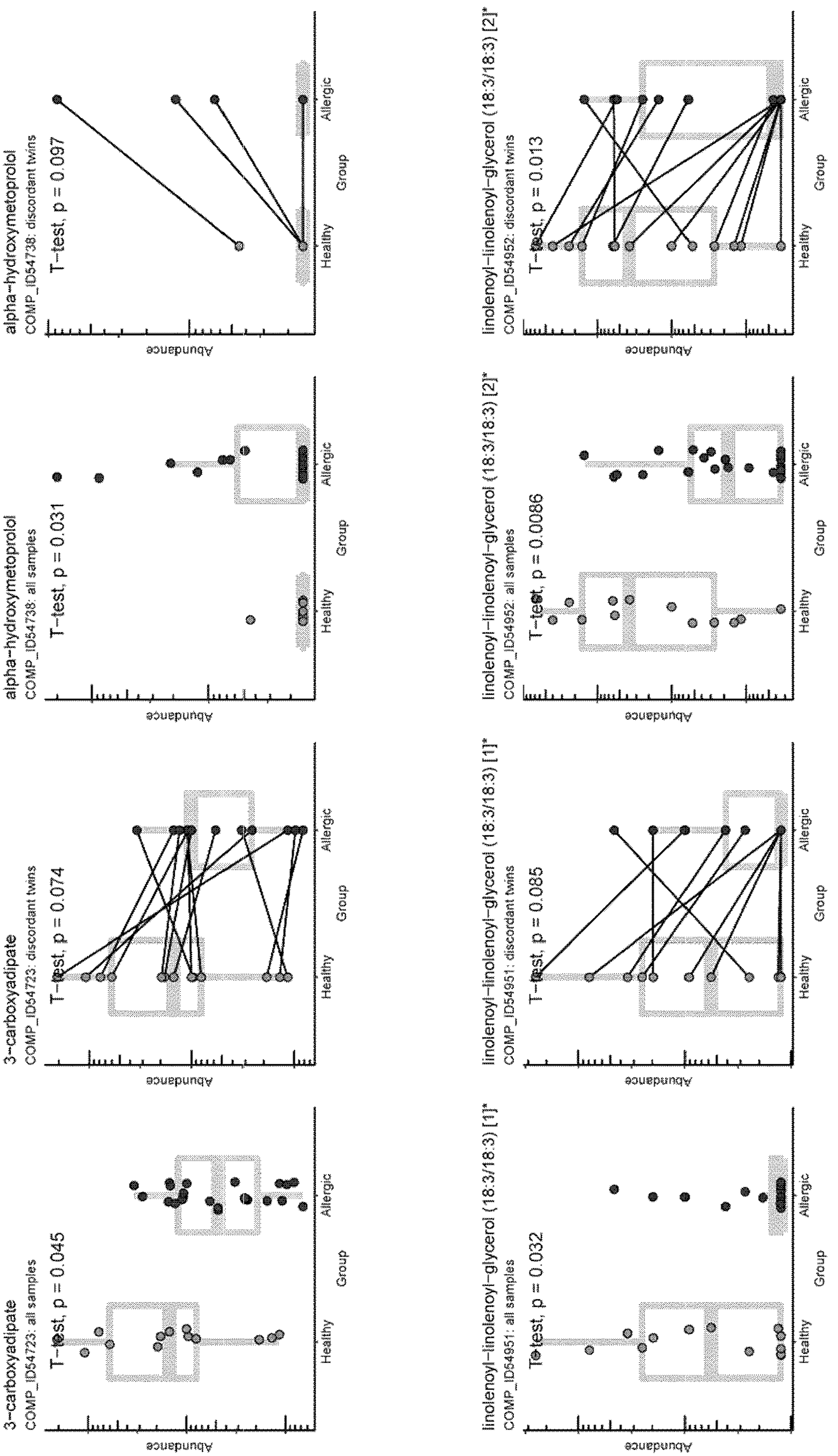
Figure 16F:
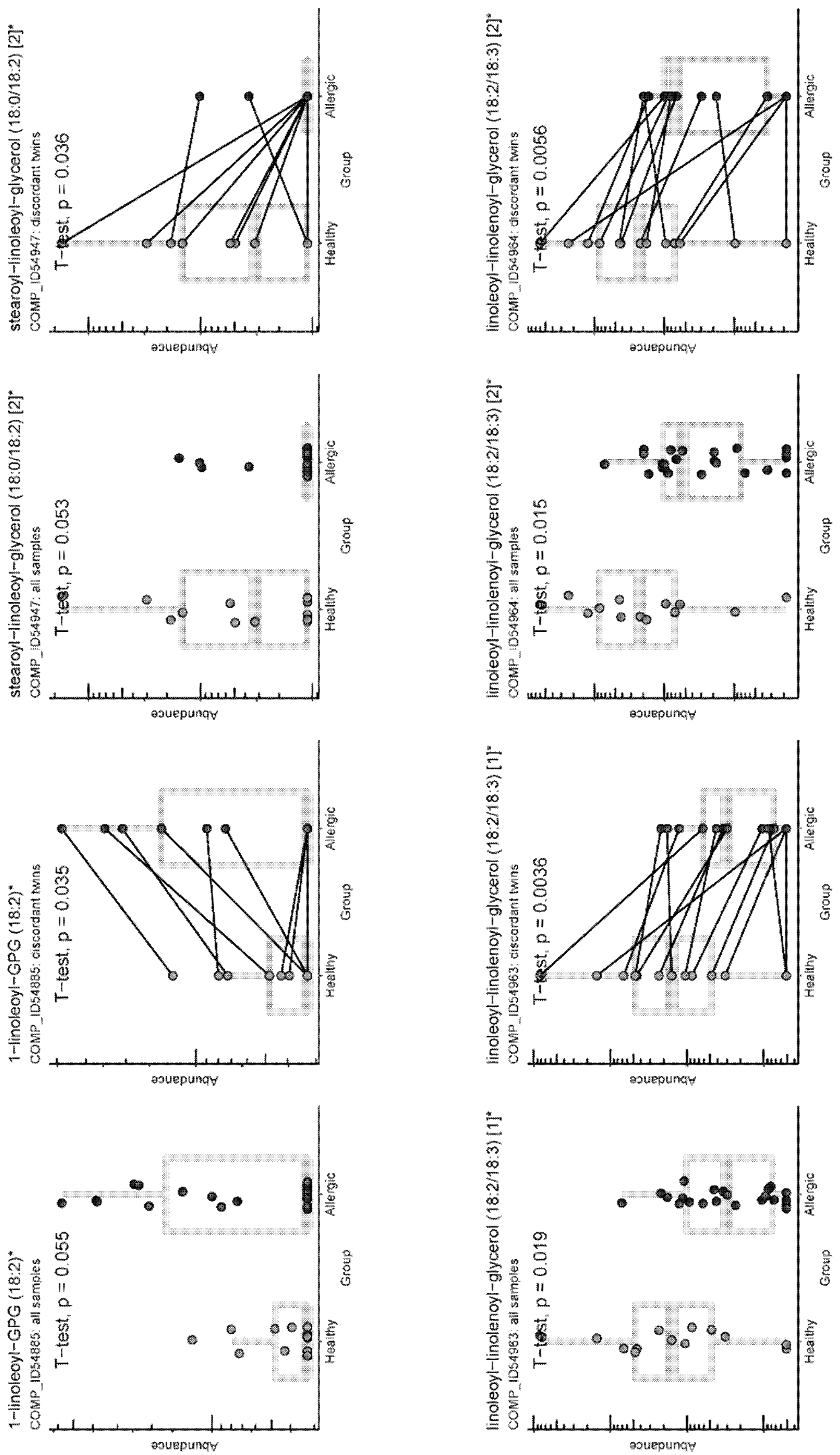
Figure 16G:
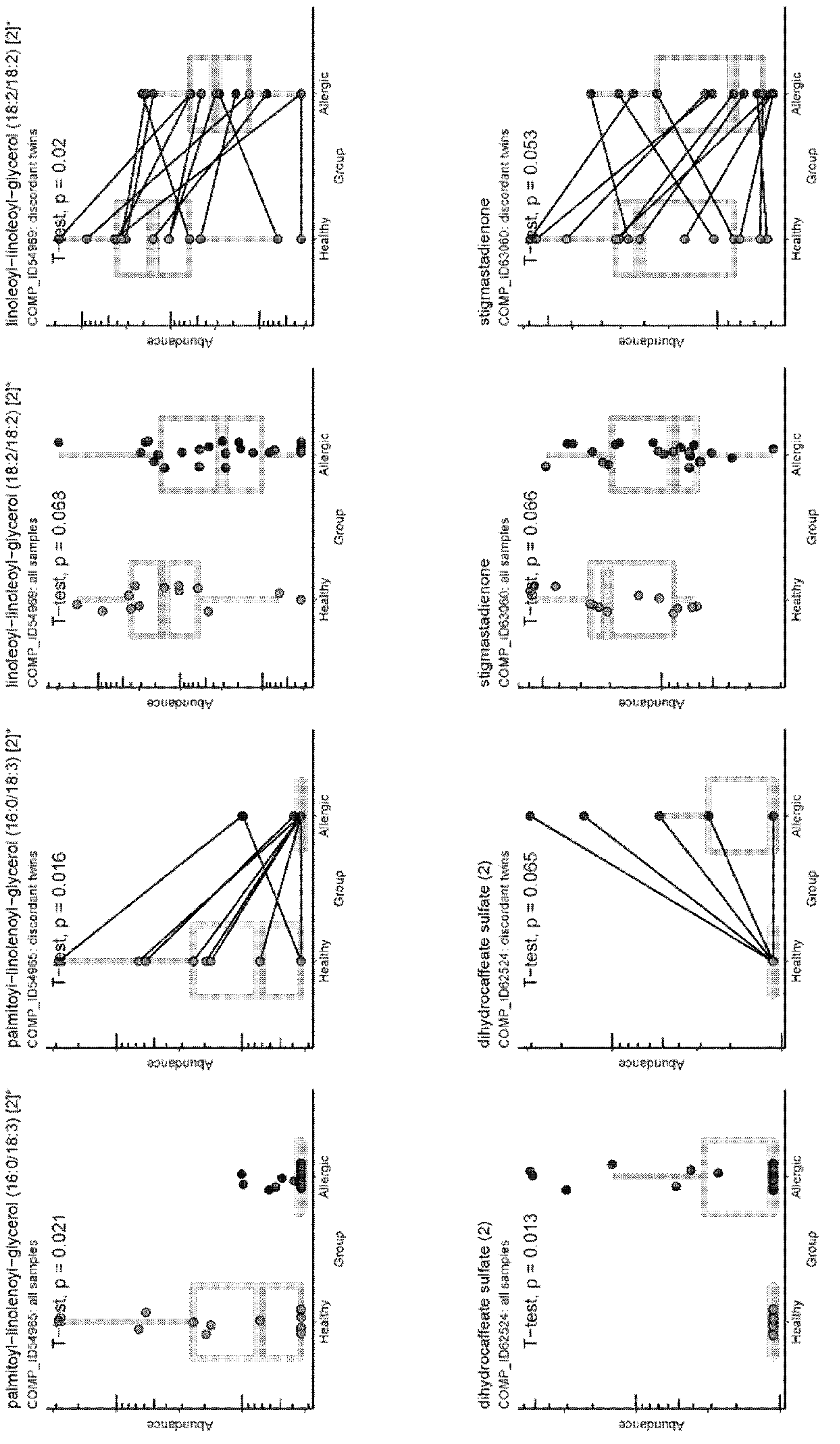
Figure 16H:
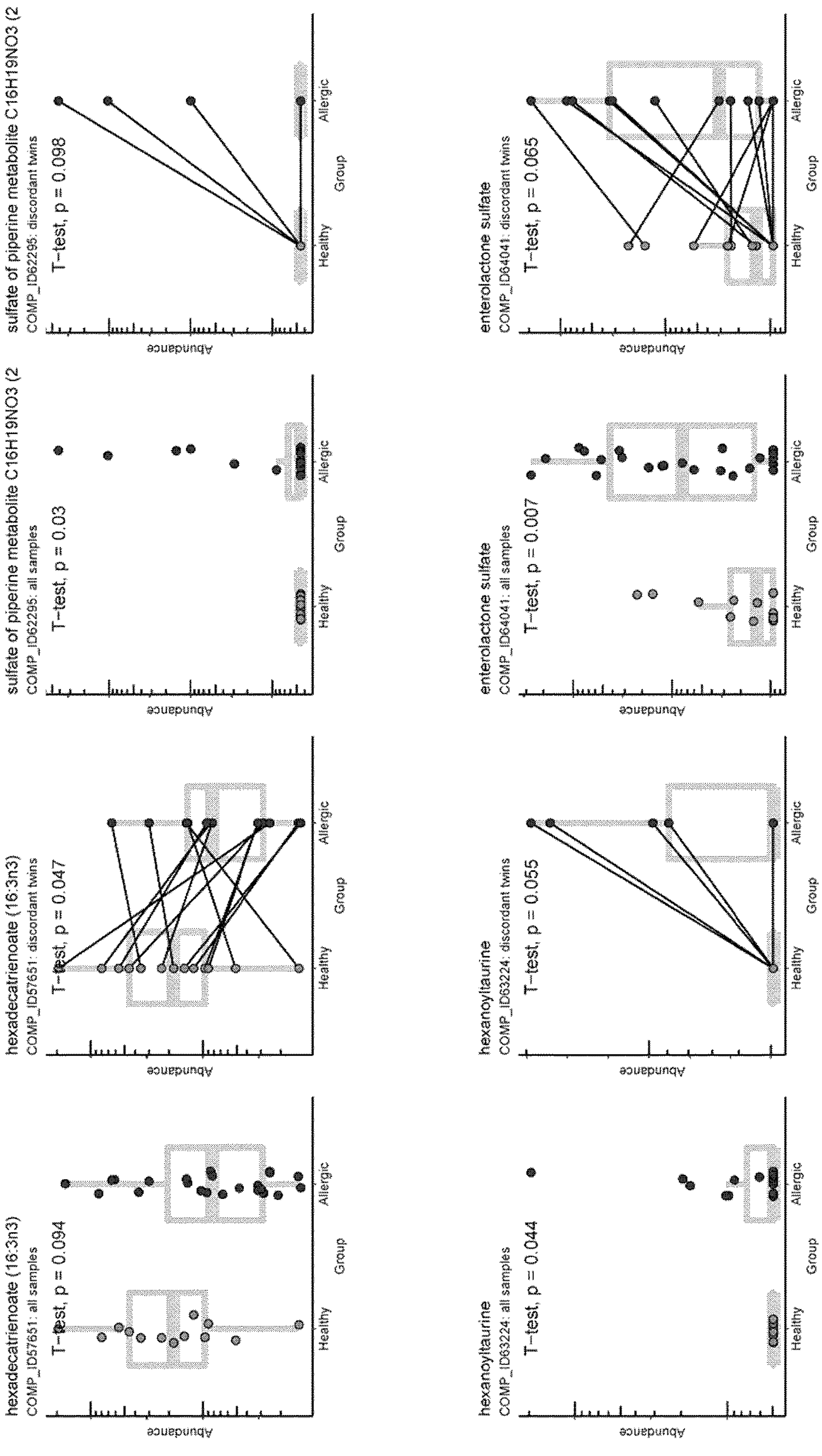

After annotating the 97 metabolites into super-pathways and sub-pathways, healthy twins showed distinct enrichment at the pathway level compared with allergic twins (FIG. 14A). Specifically, as shown in FIG. 14A, among other pathways, the diacylglycerol (DAG) sub-pathway was significantly enriched in the 33 metabolites more abundant in healthy twins (FDR-adjusted P<0.00001), and food component/plant sub-pathway was significantly enriched in the 64 metabolites more abundant in allergic twins (FDR-adjusted P=0.0074). One of the DAG metabolites, Linoleoyl-linolenoyl-glycerol (18:2/18:3) [1]*(Comp ID: 54963), was significantly higher (P=0.0036) in healthy twins compared to allergic twins in discordant pairs (FIG. 15A) and was significant in the twin cohort overall (FIG. 14B, P=0.019). On the other hand, secoisolariciresinol (Comp ID: 38105) (SECO) from the food component/plant pathway was higher in allergic twins compared with healthy twins (P=0.0067) (FIG. 14C) with the same trend observed in discordant twin pairs (P=0.094) (FIG. 15B).

In an attempt to interpret the source of these metabolites, the data was compared with an internal microbial metabolite database under active development from Metabolon Inc. (accessed Oct. 24, 2019). Among the 992 metabolites with annotated pathways that were examined, 129 overlapped with the Metabolon database. Of the 129 overlapping metabolites, 66 were marked with discovery sites such as colon, feces, urine, plasma, tissues, or multiple sites; 38 (58%) of the 66 metabolites were from colon or feces. Also, of the 129 metabolites, 13 were among the 97 compounds significantly differentially abundant between healthy and allergic twins, including 1-methylhistamine, 3-hydroxyphenylacetate, 3,4-dihydroxyphenylacetate, betaine, skatol, ethylmalonate, creatine, creatinine, putrescine, phenylacetylglycine, taurolithocholate 3-sulfate, biotin, and D-urobilin.

Additionally, eight short-chain fatty acids (SCFAs) were profiled using GC-MS technology: 2-methylbutyric acid, acetic acid, butyric acid, hexanoic acid, isobutyric acid, isovaleric acid, propionic acid, and valeric acid. The abundance of these eight SCFAs was then compared between allergic and healthy twins. Within the 13 discordant twin pairs, no SCFA reached P<0.10, potentially due to the single point-in-time analysis (data not shown).

The DAG sub-pathway was the most significantly different between healthy and allergic twins (FDR-adjusted P<0.00001) and was enriched in the 33 metabolites more abundant in healthy twins. In addition to *P. faecium* (cluster 1), metabolites in the DAG sub-pathway were strongly correlated with other bacteria in OTU clusters 1 and 2, many of which are Clostridia. The identification of readily measurable metabolites which distinguish healthy and allergic twins has important implications for the development of microbiome-modulating therapeutics because of their potential as biomarkers, particularly in clinical trials. Laboratory-based assays measuring, in particular, DAG may have great utility as biochemical indicators of therapeutic interventions that shift the microbiota towards health.

The food component/plant pathway was most significantly enriched in allergic twins after FDR correction (FDR-adjusted P=0.0074), particularly the metabolite secoisolariciresinol (SECO). SECO is commonly observed as an intermediate product in the bacteria-mediated breakdown of plant-derived lignans into enterolignans, such as enterodiol and enterolactone, which have numerous benefits for human health (33-35). Several bacterial species and genes are involved in the multi-step process of lignan metabolism (34, 36, 37). Of particular interest, the gene glm codes for an enzyme which methylates SECO into dmSECO, allowing further biotransformation into enterodiol by other bacteria (37) Phylogenetic analysis suggests that glm is expressed by a wide variety of bacteria, the majority of which are Lachnospiraceae (37). The abundance of SECO in feces was negatively correlated with the abundance of several OTUs in healthy individuals (many of which were Lachnospiraceae or Ruminococcaceae). The high abundance of SECO in the feces of allergic twins supports the taxonomic analysis, as the buildup of this intermediate product may be a direct effect of the lower abundance of Clostridia in these individuals.

Example 3—Identifying Bacterial Species with a Protective Role Against Food Allergy The two datasets described in Example 1 (OTUs) and Example 2 (metabolites) were correlated to identify any bacterial species or metabolites that may be mechanistically related to health in the cohort. Overall, the OTUs differentially abundant between healthy and allergic twin groups were correlated with different sets of metabolites and pathways. The abundance of 64 differentially abundant OTUs was correlated with the 97 metabolites (FIG. 17) and 21 healthy-abundant OTUs and one allergic-abundant OTU were identified with consistent correlation across metabolites at per sample level (FIG. 18; Table 5).

TABLE 5

List of 22 OTUs correlated with metabolites

| OTU | Family |
|---|---|
| 186478 | Ruminococcaceae |
| 188079 | Ruminococcaceae |
| 196139 | Ruminococcaceae |
| 198184 | Ruminococcaceae |
| 509709 | Lachnospiraceae |
| 556835 | Veillonellaceae |
| 574038 | Lachnospiraceae |
| 658370 | Lachnospiraceae |
| 823634 | Ruminococcaceae |
| New.CleanUp.ReferenceOTU112566 | Bacteroidaceae |
| New.CleanUp.ReferenceOTU1320 | Ruminococcaceae |
| New.CleanUp.ReferenceOTU135990 | Lachnospiraceae |
| New.CleanUp.ReferenceOTU141755 | Lachnospiraceae |
| New.CleanUp.ReferenceOTU153408 | Bacteroidaceae |
| New.CleanUp.ReferenceOTU153961 | Ruminococcaceae |
| New.CleanUp.ReferenceOTU164203 | Ruminococcaceae |
| New.CleanUp.ReferenceOTU28435 | Lachnospiraceae |
| New.CleanUp.ReferenceOTU57003 | Lachnospiraceae |
| New.CleanUp.ReferenceOTU58395 | Lachnospiraceae |
| New.CleanUp.ReferenceOTU86790 | Lachnospiraceae |
| New.CleanUp.ReferenceOTU92834 | Ruminococcaceae |
| New.ReferenceOTU129 | Bacteroidaceae |

Figure 19:
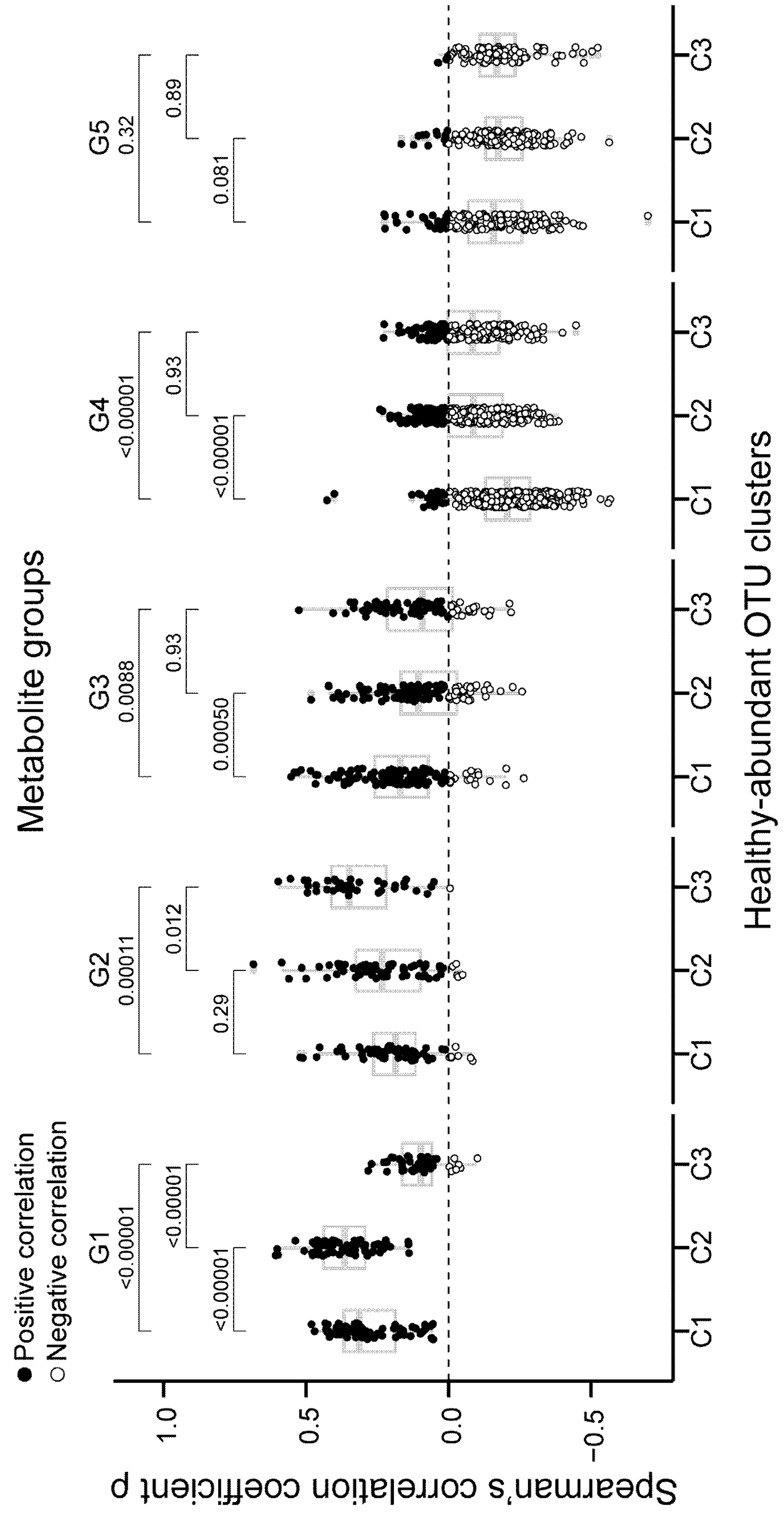
FIG. 19 shows distribution of metabolite Spearman's correlation coefficient between healthy-abundant OTU clusters 1 to 3 for each metabolite group from FIG. 18. Spearman's correlation coefficient ρ from FIG. 18 is shown on the y-axis. Healthy-abundant OTU clusters 1 to 3 from FIG. 18 are shown on the x-axis. Pairwise comparison P-values are computed between C1/C2, C1/C3, and C2/C3 for each metabolite group. Tukey's honestly significant difference (HSD) test was used which controls false discovery rate for multiple comparisons. Each dot denotes one metabolite. The bounds of the boxes represent the 25th and 75th percentiles, the horizontal center line indicates the median, and the whiskers extend to data points within a maximum of 1.5 times the IQR.
Figure 20A:
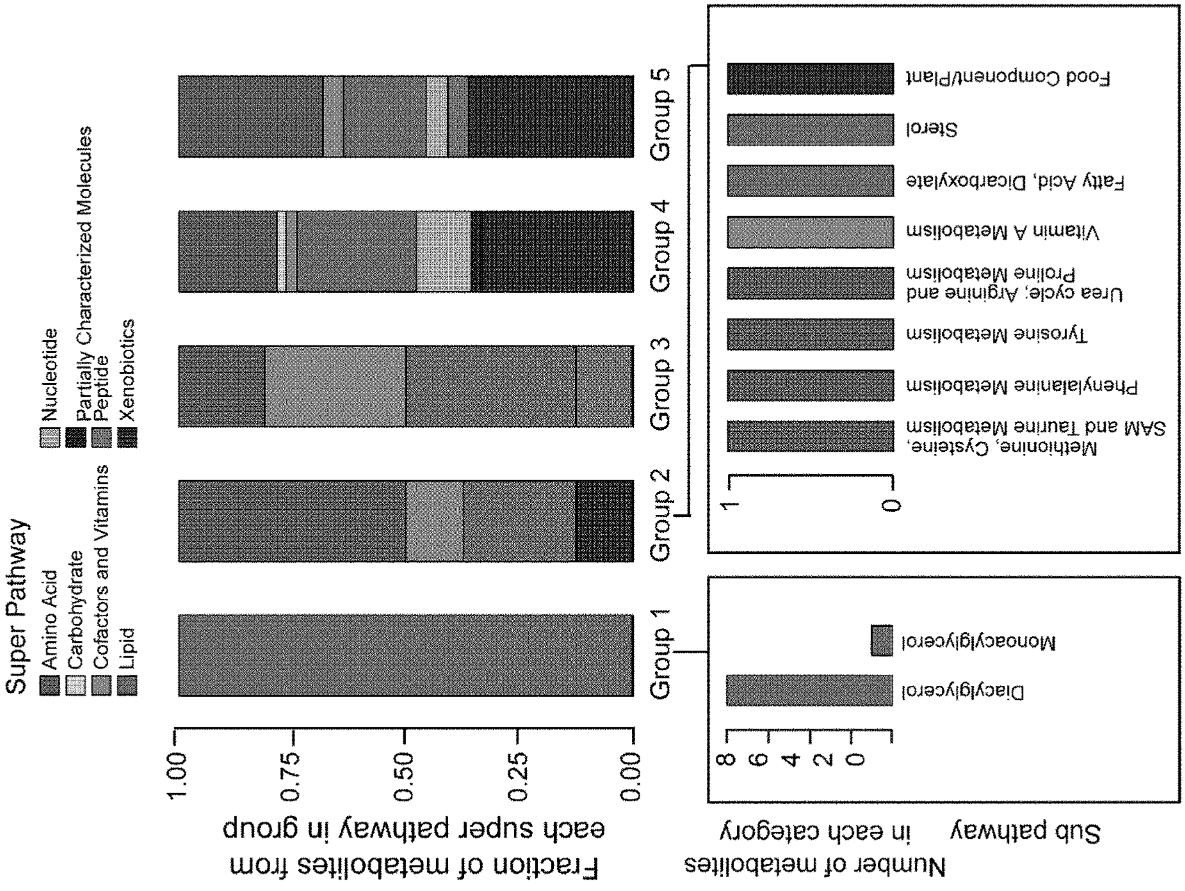
FIGS. 20A-20E show that two bacterial species correlated with metabolic pathways are differentially abundant between healthy and allergic twins.

The metabolites were divided into 5 categories based on their abundance correlation consistency among OTU clusters 1 to 3 (consisting of 21 healthy-abundant OTUs; cluster 4 only contains 1 OTU from an allergic-abundant taxon and was not used for metabolite group annotation). The 5 metabolite groups are (FIG. 18; FIG. 19): (group 1) positively correlated with the 3 OTU clusters, stronger in clusters 1 and 2 relative to cluster 3 (n=9); (group 2) positively correlated with the 3 OTU clusters, stronger in cluster 3 relative to clusters 1 and 2 (n=8); (group 3) correlated with OTU clusters with mixed patterns (n=16); (group 4) negatively correlated with the 3 OTU clusters, stronger in cluster 1 relative to clusters 2 and 3 (n=46); and (group 5) negatively correlated with the 3 OTU clusters with similar distribution (n=22). These 5 metabolite groups showed distinctly different distributions of metabolite super-pathways and sub-pathways (FIG. 20A). In particular, group 1 was dominated by metabolites from lipid super-pathway including diacylglycerol and monoacylglycerol (FIG. 20A), whereas whereas amino acid metabolism, including tyrosine, phenylalanine, arginine, proline, methionine, cysteine, S-adenosylmethionine (SAM), and taurine was enriched in group 2 (FIG. 20A).

Figure 20B:
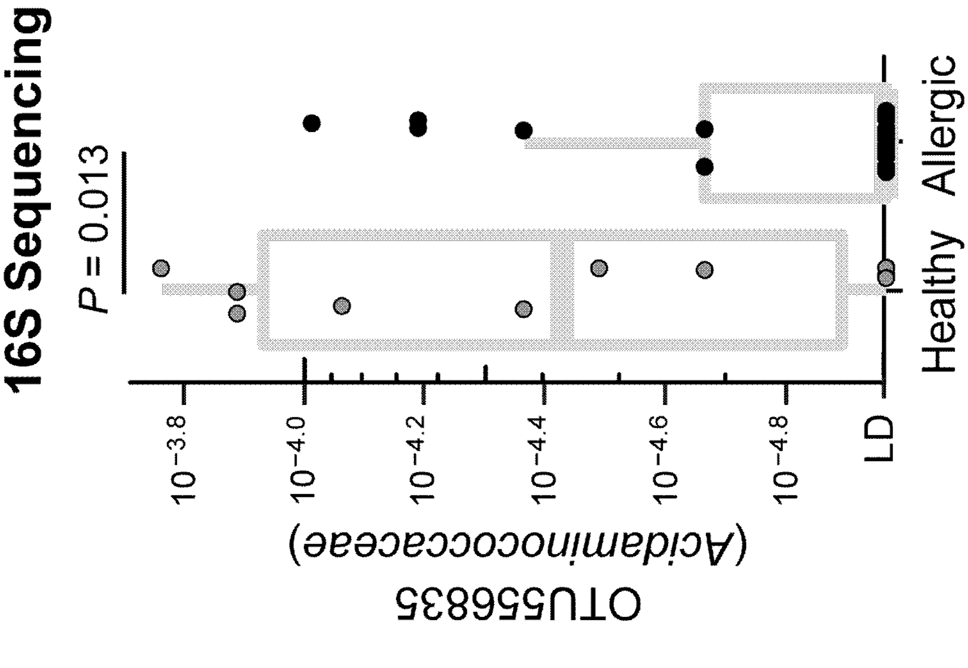
Figure 20C:
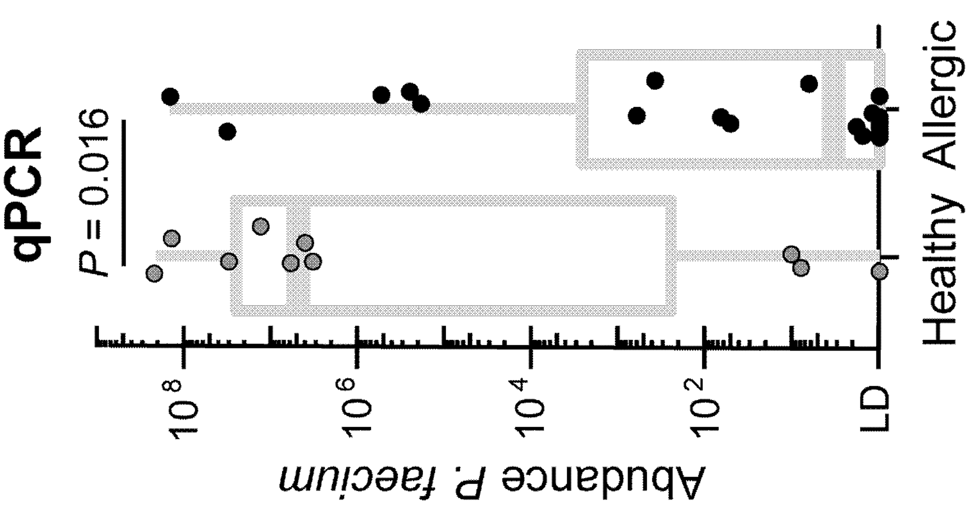
Figure 20E:
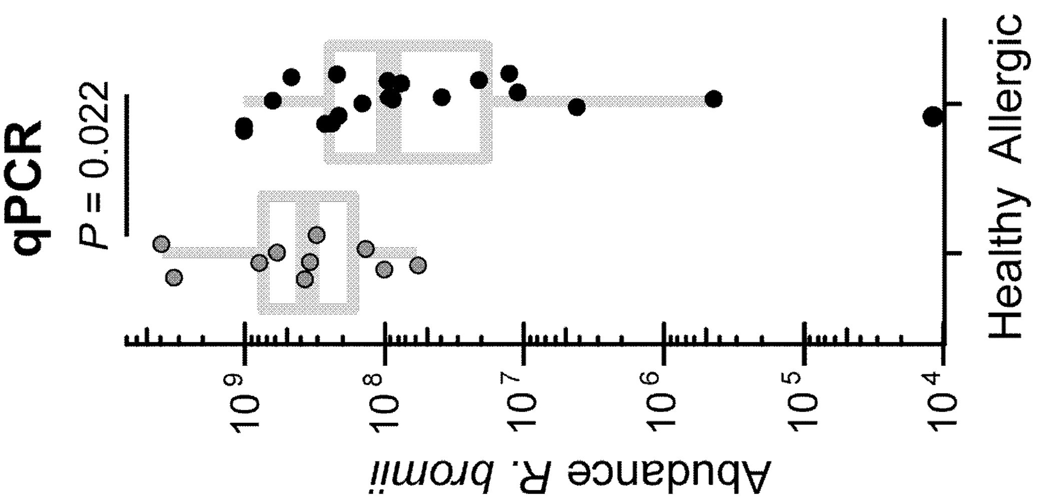
Figure 20D:
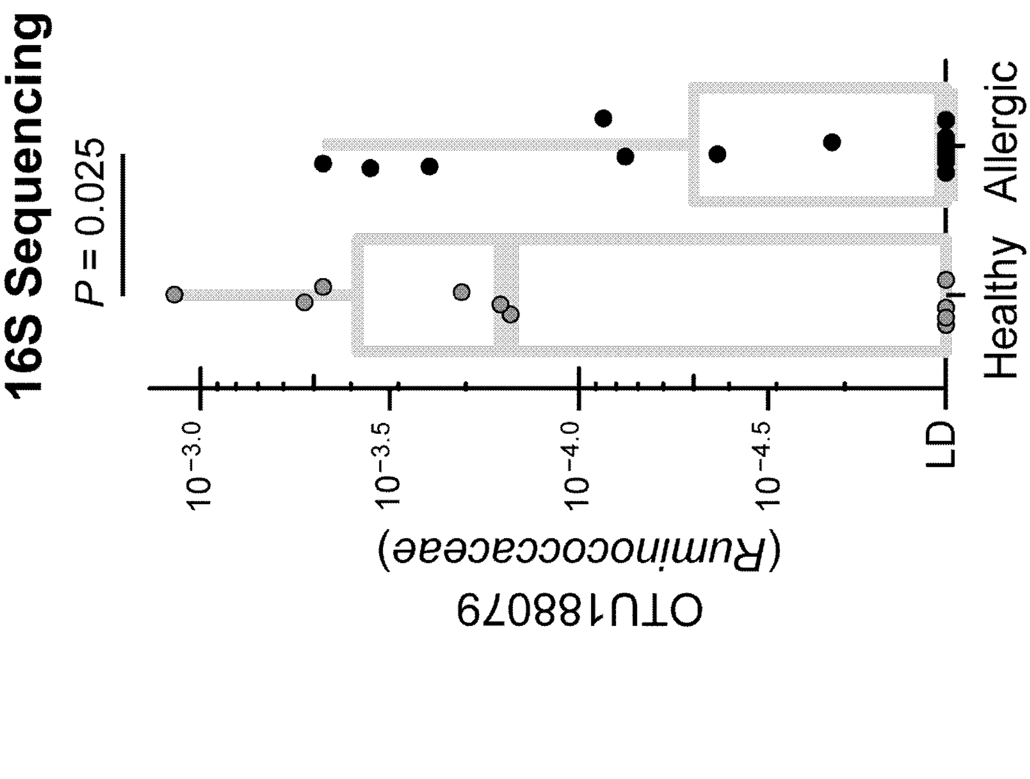
Figure 21B:
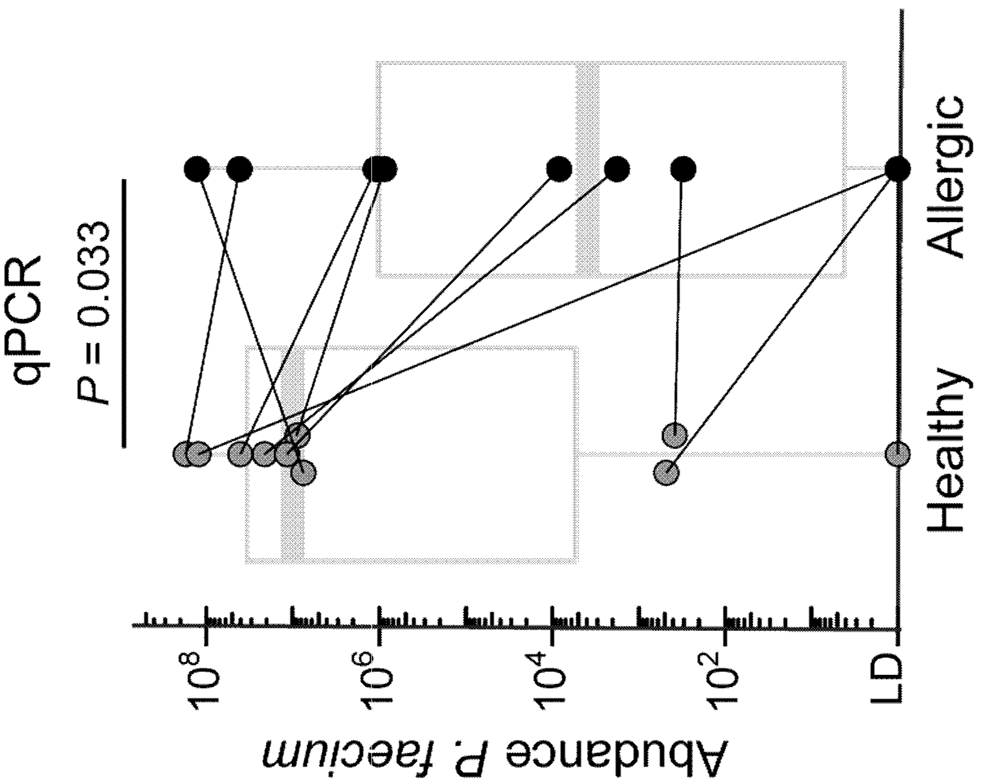
FIGS. 21A and 21B show qPCR validation of *Phascolarctobacterium faecium* discovered by 16S sequencing platform, shown in discordant twin pairs only (10 pairs, n=20). 2 out of 12 discordant pairs did not have DNA material left for qPCR validation and were not included.
Figure 21A:
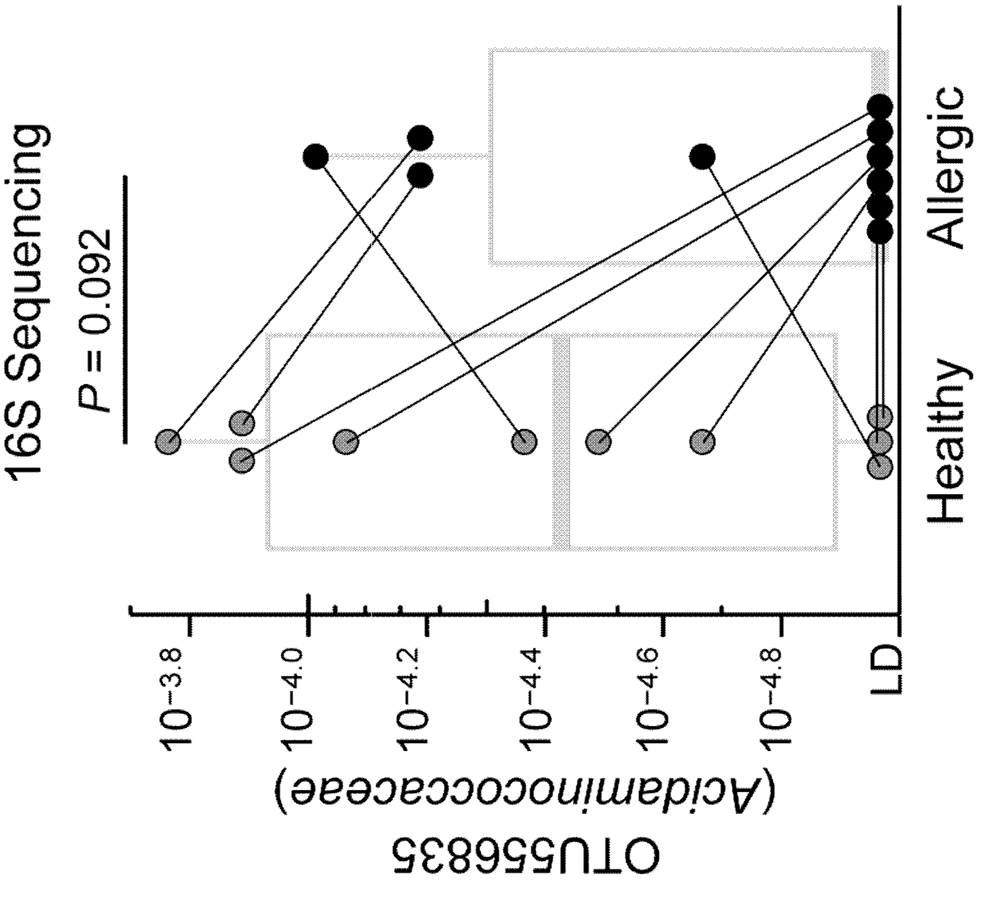
Figure 22A:
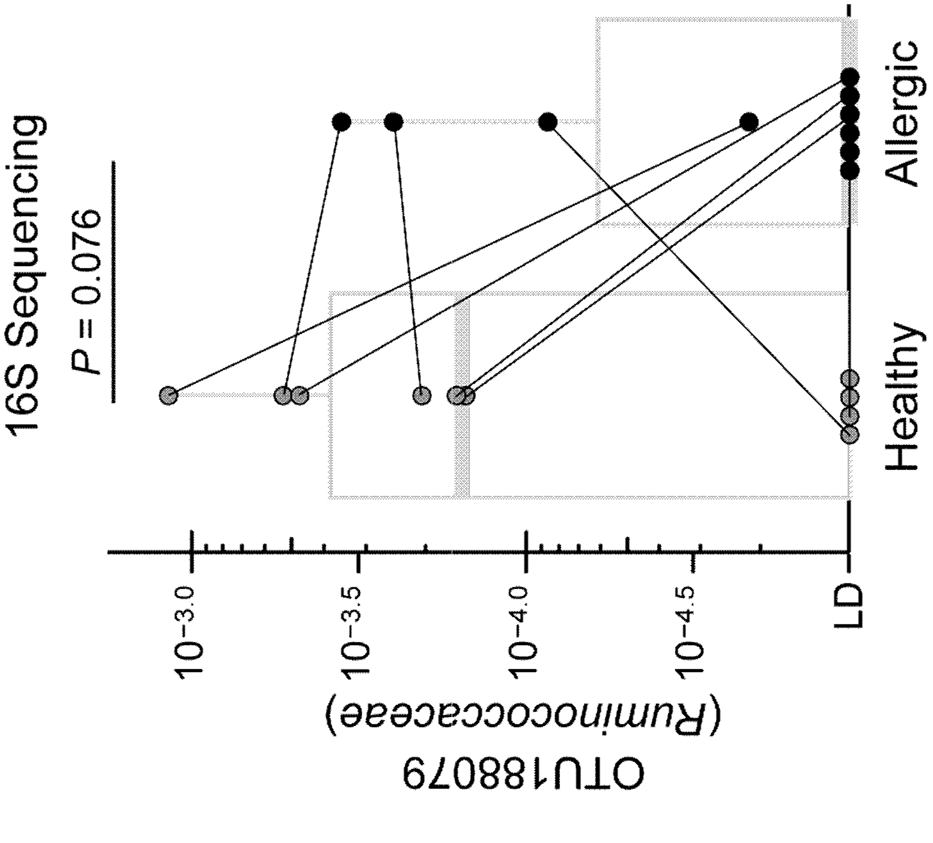
FIGS. 22A and 22B show qPCR validation of *Ruminococcus bromii* discovered by 16S sequencing platform, shown in discordant twin pairs only (10 pairs, n=20). 2 out of 12 discordant pairs did not have DNA material left for qPCR validation and were not included.
Figure 22B:
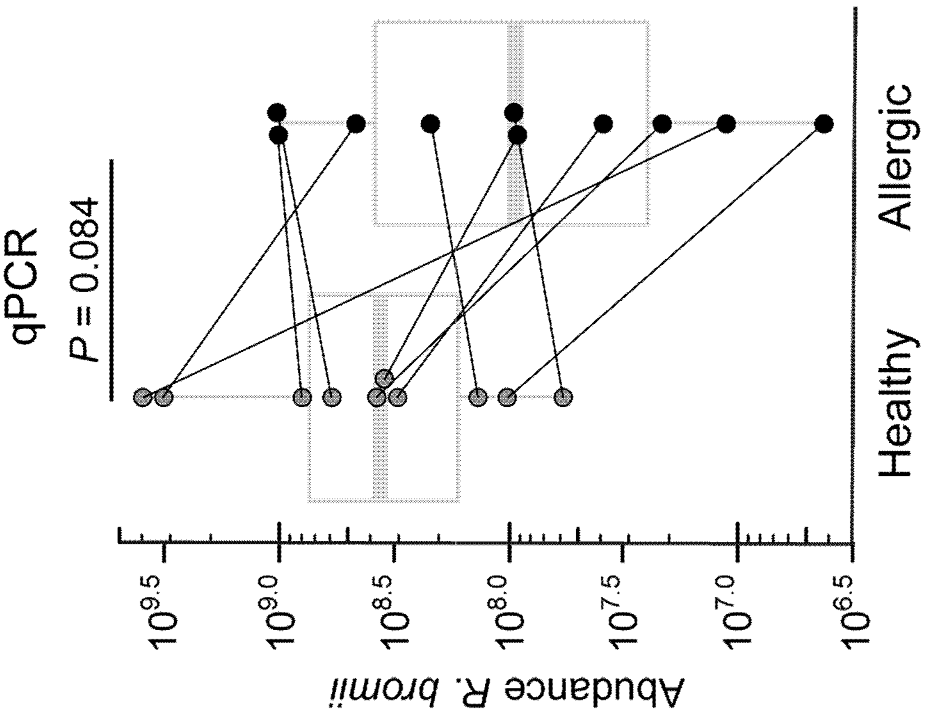

To annotate the 22 OTUs at the species-level resolution, the assembled 16S sequence of each OTU was searched against NCBI's Bacteria/Archaea 16S reference database using BLAST (34). At sequence identity of 99% or higher, OTU556835 was matched to *Phascolarctobacterium faecium* (accession ID NR_026111.1) and both OTU188079 and OTU823634 were matched to *Ruminococcus bromii* (accession ID NR_025930.1). The other OTUs (abundant in either healthy or allergic twins) did not have matches meeting the identity threshold. Quantitative PCR (qPCR) validated the significantly higher abundance of *P. faecium* in healthy twins compared with allergic twins (P=0.016) (FIGS. 20B and 20C; FIG. 21B). *P. faecium* is an obligate anaerobic non-spore-forming bacterium that consumes succinate and produces SCFAs including acetate and propionate (17, 18). *P. faecium* was grouped in cluster 1 and was most highly correlated with a number of DAG metabolites. *P. faecium* was also strongly positively correlated with tocopherol and negatively correlated with a variety of metabolites, including those from the secondary bile acid metabolism pathway. *R. bromii* was also qPCR-validated to be enriched in the healthy compared with the allergic twin group (P=0.022) (FIGS. 20D and 20E; FIG. 22B). *R. bromii* is a strictly anaerobic, spore-forming Clostridia important for the degradation of dietary resistant starch (19). It was associated with group 2 metabolites involved in fatty acid, amino acid, and sterol metabolism.

All of the methods disclosed and claimed herein can be made and executed without undue experimentation in light of the present disclosure. While the compositions and methods of this invention have been described in terms of certain embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Gupta R S, Warren C M, Smith B M, Blumenstock J A, Jiang J, Davis M M, et al. The Public Health Impact of Parent-Reported Childhood Food Allergies in the United States. *Pediatrics.* 2018; 142(6).
2. Gupta R S, Warren C M, Smith B M, Jiang J, Blumenstock J A, Davis M M, et al. Prevalence and Severity of Food Allergies Among U S Adults. *JAMA Netw Open.* 2019; 2(1):e185630.
3. Iweala O I, and Nagler C R. The Microbiome and Food Allergy. *Annu Rev Immunol.* 2019; 37:377-403.

4. Wesemann D R, and Nagler C R. The Microbiome, Timing, and Barrier Function in the Context of Allergic Disease. *Immunity.* 2016; 44(4):728-38.
5. Torow N, and Hornef M W. The Neonatal Window of Opportunity: Setting the Stage for Life-Long Host-Microbial Interaction and Immune Homeostasis. *J Immunol.* 2017; 198(2):557-63.
6. Thompson-Chagoyan O C, Fallani M, Maldonado J, Vieites J M, Khanna S, Edwards C, et al. Faecal microbiota and short-chain fatty acid levels in faeces from infants with cow's milk protein allergy. *Int Arch Allergy Immunol.* 2011; 156(3):325-32.
7. Ling Z, Li Z, Liu X, Cheng Y, Luo Y, Tong X, et al. Altered fecal microbiota composition associated with food allergy in infants. *Appl Environ Microbiol.* 2014; 80(8):2546-54.
8. Azad M B, Konya T, Guttman D S, Field C J, Sears M R, HayGlass K T, et al. Infant gut microbiota and food sensitization: associations in the first year of life. *Clin Exp Allergy.* 2015; 45(3):632-43.
9. Investigators PGoC, Vickery B P, Vereda A, Casale T B, Beyer K, du Toit G, et al. AR101 Oral Immunotherapy for Peanut Allergy. *N Engl J Med.* 2018; 379(21):1991-2001.
10. Chinthrajah R S, Purington N, Andorf S, Long A, O'Laughlin K L, Lyu S C, et al. Sustained outcomes in oral immunotherapy for peanut allergy (POISED study): a large, randomised, double-blind, placebo-controlled, phase 2 study. *Lancet.* 2019; 394(10207):1437-49.
11. Freeland D M H, Manohar M, Andorf S, Hobson B D, Zhang W, and Nadeau K C. Oral immunotherapy for food allergy. *Semin Immunol.* 2017; 30:36-44.
12. Wood R A. Food allergen immunotherapy: Current status and prospects for the future. *J Allergy Clin Immunol.* 2016; 137(4):973-82.
13. Andorf S, Purington N, Block W M, Long A J, Tupa D, Brittain E, et al. Anti-IgE treatment with oral immunotherapy in multifood allergic participants: a double-blind, randomised, controlled trial. *Lancet Gastroenterol Hepatol.* 2018; 3(2):85-94.
14. Jimenez M, Langer R, and Traverso G. Microbial therapeutics: New opportunities for drug delivery. *J Exp Med.* 2019; 216(5):1005-9.
15. Stefka A T, Feehley T, Tripathi P, Qiu J, McCoy K, Mazmanian S K, et al. Commensal bacteria protect against food allergen sensitization. *Proc Natl Acad Sci USA.* 2014; 111(36):13145-50.
16. Bishop W R, and Bell R M. Functions of diacylglycerol in glycerolipid metabolism, signal transduction and cellular transformation. *Oncogene Res.* 1988; 2(3):205-18.
17. Ogata Y, Suda W, Ikeyama N, Hattori M, Ohkuma M, and Sakamoto M. Complete Genome Sequence of *Phascolarctobacterium faecium* JCM 30894, a Succinate-Utilizing Bacterium Isolated from Human Feces. *Microbiol Resour Announc.* 2019; 8(3).
18. Wu F, Guo X, Zhang J, Zhang M, Ou Z, and Peng Y. *Phascolarctobacterium faecium* abundant colonization in human gastrointestinal tract. *Exp Ther Med.* 2017; 14(4): 3122-6.
19. Ze X, Duncan S H, Louis P, and Flint H J. *Ruminococcus bromii* is a keystone species for the degradation of resistant starch in the human colon. *ISME J.* 2012; 6(8):1535-43.
20. Mukhopadhya I, Morais S, Laverde-Gomez J, Sheridan P O, Walker A W, Kelly W, et al. Sporulation capability and amylosome conservation among diverse human colonic and rumen isolates of the keystone starch-degrader *Ruminococcus bromii.* Environmental microbiology. 2018; 20(1):324-36.
21. Sinha R, Chen J, Amir A, Vogtmann E, Shi J, Inman K S, et al. Collecting Fecal Samples for Microbiome Analyses in Epidemiology Studies. *Cancer Epidemiol Biomarkers Prev.* 2016; 25(2):407-16.
22. Caporaso J G, Lauber C L, Walters W A, Berg-Lyons D, Huntley J, Fierer N, et al. Ultra-high-throughput microbial community analysis on the Illumina HiSeq and MiSeq platforms. *ISME J.* 2012; 6(8):1621-4.
23. Caporaso J G, Kuczynski J, Stombaugh J, Bittinger K, Bushman F D, Costello E K, et al. QIIME allows analysis of high-throughput community sequencing data. *Nat Methods.* 2010; 7(5):335-6.
24. Feehley T, Plunkett C H, Bao R, Choi Hong S M, Culleen E, Belda-Ferre P, et al. Healthy infants harbor intestinal bacteria that protect against food allergy. *Nat Med.* 2019; 25(3):448-53.
25. DeSantis T Z, Hugenholtz P, Larsen N, Rojas M, Brodie E L, Keller K, et al. Greengenes, a chimera-checked 16S rRNA gene database and workbench compatible with ARB. *Appl Environ Microbiol.* 2006; 72(7):5069-72.
26. Caporaso J G, Bittinger K, Bushman F D, DeSantis T Z, Andersen G L, and Knight R. PyNAST: a flexible tool for aligning sequences to a template alignment. *Bioinformatics.* 2010; 26(2):266-7.
27. Edgar R C. Search and clustering orders of magnitude faster than BLAST. *Bioinformatics.* 2010; 26(19):2460-1.
28. Haas B J, Gevers D, Earl A M, Feldgarden M, Ward D V, Giannoukos G, et al. Chimeric 16S rRNA sequence formation and detection in Sanger and 454-pyrosequenced PCR amplicons. *Genome Res.* 2011; 21(3):494-504.
29. Oksanen J, Blanchet F G, Friendly M, Kindt R, Legendre P, McGlinn D, et al. vegan: Community Ecology Package. *R package version* 25-2. 2018; available on the web at CRAN.R-project.org/package=vegan.
30. Jiang L, Amir A, Morton J T, Heller R, Arias-Castro E, and Knight R. Discrete False-Discovery Rate Improves Identification of Differentially Abundant Microbes. *mSystems.* 2017; 2(6).
31. Benjamini Y, and Hochberg Y. Controlling the False Discovery Rate—a Practical and Powerful Approach to Multiple Testing. *J Roy Stat Soc B Met.* 1995; 57(1):289-300.
32. Human Microbiome Project C. Structure, function and diversity of the healthy human microbiome. *Nature.* 2012; 486(7402):207-14.
33. Clavel T, Borrmann D, Braune A, Dore J, and Blaut M. Occurrence and activity of human intestinal bacteria involved in the conversion of dietary lignans. Anaerobe. 2006; 12(3):140-7.
34. Clavel T, Henderson G, Engst W, Dore J, and Blaut M. Phylogeny of human intestinal bacteria that activate the dietary lignan secoisolariciresinol diglucoside. FEMS microbiology ecology. 2006; 55(3):471-8.
35. Adlercreutz H. Lignans and human health. Crit Rev Clin Lab Sci. 2007; 44(5-6):483-525.
36. Woting A, Clavel T, Loh G, and Blaut M. Bacterial transformation of dietary lignans in gnotobiotic rats. *FEMS microbiology ecology.* 2010; 72(3):507-14.
37. Bess E N, Bisanz J E, Yarza F, Bustion A, Rich B E, Li X, et al. Genetic basis for the cooperative bioactivation of plant lignans by Eggerthella lenta and other human gut bacteria. *Nat Microbiol.* 2020; 5(1):56-66.

The invention claimed is:

1. A method for treating a food allergy in a subject, the method comprising providing to the subject a food allergy therapy, wherein the food allergy therapy is:

an immunotherapy, a steroid, an antihistamine, a hormone, a microbiome-modulating therapy, or a combination thereof, wherein the subject was determined to have a decreased operational taxonomic units (OTU) abundance score relative to a control or reference sample, and wherein the OTU abundance score was calculated using at least 20 of the OTUs selected from OTU173135, OTU174588, OTU174818, OTU176077, OTU176664, OTU178799, OTU186478, OTU188079, OTU189816, OTU190169, OTU190649, OTU195258, OTU196139, OTU198184, OTU198941, OTU2331530, OTU269611, OTU295804, OTU343313, OTU361702, OTU362342, OTU362765, OTU370099, OTU4402610, OTU509709, OTU556835, OTU574038, OTU658370, OTU823634, New.CleanUp.ReferenceOTU110487, New.CleanUp. ReferenceOTU112566, New.CleanUp.ReferenceOTU122371, New.CleanUp.ReferenceOTU124061, New.CleanUp.ReferenceOTU127991, New.CleanUp.ReferenceOTU1320, New.CleanUp.ReferenceOTU134087, New.CleanUp.ReferenceOTU135990, New.CleanUp.ReferenceOTU141755, New.CleanUp.ReferenceOTU141972, New.CleanUp.ReferenceOTU149108, New.CleanUp.ReferenceOTU152821, New.CleanUp.ReferenceOTU153408, New.CleanUp.ReferenceOTU153961, New.CleanUp.ReferenceOTU156924, New.CleanUp.ReferenceOTU164203, New.CleanUp.ReferenceOTU28435, New.CleanUp.ReferenceOTU37938, New.CleanUp.ReferenceOTU41338, New.CleanUp.ReferenceOTU41725, New.CleanUp.ReferenceOTU47134, New.CleanUp.ReferenceOTU5050, New.CleanUp.ReferenceOTU57003, New.CleanUp.ReferenceOTU58395, New.CleanUp.ReferenceOTU58632, New.CleanUp.ReferenceOTU74051, New.CleanUp.ReferenceOTU79183, New.CleanUp.ReferenceOTU80284, New.CleanUp.ReferenceOTU86790, New.CleanUp.ReferenceOTU86928, New.CleanUp.ReferenceOTU89172, New.CleanUp.ReferenceOTU92834, New.CleanUp.ReferenceOTU97550, New.CleanUp.ReferenceOTU99007, and New.ReferenceOTU129.

2. The method of claim 1, wherein the control or reference sample is a sample from a healthy individual.

3. The method of claim 1, wherein the food allergy therapy is a microbiome-modulating therapy.

4. The method of claim 3, wherein the microbiome-modulating therapy comprises providing to the subject a composition comprising a therapeutically effective amount of (a) *Phascolarctobacterium faecium* and/or (b) *Ruminococcus bromii*.

5. The method of claim 4, wherein the composition comprises *Phascolarctobacterium faecium* and *Ruminococcus bromii*.

6. The method of claim 5, wherein the composition comprises (i) between $1\times10^3$ and $1\times10^{15}$ colony forming units (CFU) of *Phascolarctobacterium faecium* and (ii) between $1\times10^3$ and $1\times10^{15}$ colony forming units (CFU) of *Ruminococcus bromii*.

7. The method of claim 4, wherein the composition is administered with a food of the food allergy.

8. The method of claim 1, wherein the OTU abundance score was calculated using all of the OTUs selected from OTU173135, OTU174588, OTU174818, OTU176077, OTU176664, OTU178799, OTU186478, OTU188079, OTU189816, OTU190169, OTU190649, OTU195258, OTU196139, OTU198184, OTU198941, OTU2331530, OTU269611, OTU295804, OTU343313, OTU361702, OTU362342, OTU362765, OTU370099, OTU4402610, OTU509709, OTU556835, OTU574038, OTU658370, OTU823634, New.CleanUp.ReferenceOTU110487, New.CleanUp.ReferenceOTU112566, New.CleanUp.ReferenceOTU122371, New.CleanUp.ReferenceOTU124061, New.CleanUp.ReferenceOTU127991, New.CleanUp.ReferenceOTU1320, New.CleanUp.ReferenceOTU134087, New.CleanUp.ReferenceOTU135990, New.CleanUp.ReferenceOTU141755, New.CleanUp.ReferenceOTU141972, New.CleanUp.ReferenceOTU149108, New.CleanUp.ReferenceOTU152821, New.CleanUp.ReferenceOTU153408, New.CleanUp.ReferenceOTU153961, New.CleanUp.ReferenceOTU156924, New.CleanUp.ReferenceOTU164203, New.CleanUp.ReferenceOTU28435, New.CleanUp.ReferenceOTU37938, New.CleanUp.ReferenceOTU41338, New.CleanUp.ReferenceOTU41725, New.CleanUp.ReferenceOTU47134, New.CleanUp.ReferenceOTU5050, New.CleanUp.ReferenceOTU57003, New.CleanUp.ReferenceOTU58395, New.CleanUp.ReferenceOTU58632, New.CleanUp.ReferenceOTU74051, New.CleanUp.ReferenceOTU79183, New.CleanUp.ReferenceOTU80284, New.CleanUp.ReferenceOTU86790, New.CleanUp.ReferenceOTU86928, New.CleanUp.ReferenceOTU89172, New.CleanUp.ReferenceOTU92834, New.CleanUp.ReferenceOTU97550, New.CleanUp.ReferenceOTU99007, and New.ReferenceOTU129.

9. The method of claim 1, wherein the food allergy is an allergy to one or more of peanuts, tree nuts, shellfish, soy, egg, fish, mustard, oats, olives, corn, rice, pineapple, wheat, gluten, milk, sesame, garbanzo beans, bananas, kiwi, avocado, mangos, melons, carrots, cucumber, apples, squash, and crab.

10. The method of claim 4, wherein the composition comprises *Phascolarctobacterium faecium*.

11. The method of claim 4, wherein the composition comprises between $1\times10^3$ and $1\times10^{15}$ colony forming units (CFU) of *Phascolarctobacterium faecium*.

12. The method of claim 4, wherein the composition comprises *Ruminococcus bromii*.

13. The method of claim 4, wherein the composition comprises between $1\times10^3$ and $1\times10^{15}$ colony forming units (CFU) of *Ruminococcus bromii*.

14. The method of claim 4, wherein the *Phascolarctobacterium faecium* and/or *Ruminococcus bromii* make up at least 75% of all bacteria in the composition.

15. The method of claim 4, wherein the *Phascolarctobacterium faecium* and/or *Ruminococcus bromii* make up about 100% of all bacteria in the composition.

16. The method of claim 4, wherein the composition further comprises one or more microparticles.

17. The method of claim 16, wherein the *Phascolarctobacterium faecium* and/or *Ruminococcus bromii* are encapsulated within the one or more microparticles.

18. The method of claim 1, wherein the food allergy therapy is administered orally.

* * * * *